United States Patent
Ando et al.

(10) Patent No.: US 9,563,070 B2
(45) Date of Patent: *Feb. 7, 2017

(54) DIFFRACTION-TYPE MULTIFOCAL OPHTHALMIC LENS AND MANUFACTURING METHOD THEREOF

(75) Inventors: Ichiro Ando, Kasugai (JP); Hiroaki Suzuki, Kasugai (JP); Atsushi Kobayashi, Kasugai (JP)

(73) Assignee: MENICON CO., LTD., Nagoya-shi (JP)

( * ) Notice: Subject to any disclaimer, the term of this patent is extended or adjusted under 35 U.S.C. 154(b) by 133 days.

This patent is subject to a terminal disclaimer.

(21) Appl. No.: 14/377,029

(22) PCT Filed: Feb. 9, 2012

(86) PCT No.: PCT/JP2012/000858
§ 371 (c)(1),
(2), (4) Date: Aug. 6, 2014

(87) PCT Pub. No.: WO2013/118176
PCT Pub. Date: Aug. 15, 2013

(65) Prior Publication Data
US 2014/0347624 A1     Nov. 27, 2014

(51) Int. Cl.
*G02C 7/04* (2006.01)
*G02C 7/06* (2006.01)
(Continued)

(52) U.S. Cl.
CPC .............. *G02C 7/06* (2013.01); *A61F 2/1654* (2013.01); *G02B 3/08* (2013.01); *G02B 27/4216* (2013.01);
(Continued)

(58) Field of Classification Search
CPC ........... G02C 7/06; G02C 7/041; G02C 7/044; G02C 7/028; G02C 7/049; G02C 2202/20; A61F 2/1654; A61F 2/1656; A61F 2/1618; G02B 3/08; G02B 27/4216; G02B 5/1876; G02B 5/1814; G02B 5/18; G11B 7/1353
(Continued)

(56) References Cited

U.S. PATENT DOCUMENTS 4,881,805 A    11/1989  Cohen
5,699,142 A    12/1997  Lee et al.
(Continued)

FOREIGN PATENT DOCUMENTS

EP    2 377 493 A1    10/2011
JP    A-2-137814      5/1990
(Continued)

OTHER PUBLICATIONS

International Search Report issued in International Patent Application No. PCT/JP2012/000858 dated Mar. 27, 2012.
(Continued)

*Primary Examiner* — Scott J Sugarman
*Assistant Examiner* — Ibrahima Diedhiou
(74) *Attorney, Agent, or Firm* — Oliff PLC

(57) ABSTRACT

Provided is a diffraction-type multifocal ophthalmic lens for which halos are reduced. Also provided is a diffraction-type multifocal ophthalmic lens having three or more focal points, which is implemented on the basis of the discovery that the diffraction-type multifocal ophthalmic lens has a characteristic whereby multiple focal points can be generated in the intermediate region as well as the near and far regions. Also provided is a method for manufacturing a diffraction-type multifocal ophthalmic lens which provides a simple design and manufacturing method by means of a simple diffraction structure and by replacing a cumbersome computer simulation with a simple method. This diffraction- (Continued)

type multifocal ophthalmic lens has a diffraction structure (20) where a plurality of diffraction zones are formed concentrically on the lens (10), and an equal-pitch region is provided where pitches of at least two zones among the diffraction zones are made equal.

20 Claims, 33 Drawing Sheets

(51) Int. Cl.
*A61F 2/16* (2006.01)
*G02B 3/08* (2006.01)
*G02B 27/42* (2006.01)

(52) U.S. Cl.
CPC ............... *G02C 7/041* (2013.01); *G02C 7/044* (2013.01); *G02C 2202/20* (2013.01)

(58) Field of Classification Search
USPC ............ 351/159.44, 159.73, 159.11, 159.01, 351/159.02, 159.05, 159.1, 159.12, 351/159.13, 159.14, 159.15, 159.35, 351/159.41, 159.42, 159.43; 369/112.03; 359/319, 574, 558, 159.05, 159.15, 359/159.74, 565, 571, 566, 569, 570, 576, 359/721, 741, 742, 743; 623/6.3, 6.31
See application file for complete search history.

(56) References Cited

U.S. PATENT DOCUMENTS

| | | | |
|---|---|---|---|
| 6,158,862 A | 12/2000 | Patel et al. | |
| 7,845,796 B2 | 12/2010 | Suzuki | |
| 8,500,805 B2 | 8/2013 | Kobayashi et al. | |
| 8,556,416 B2 | 10/2013 | Lawu | |
| 2006/0050234 A1 | 3/2006 | Morris et al. | |
| 2007/0182924 A1 | 8/2007 | Hong et al. | |
| 2008/0087848 A1 | 4/2008 | Lin et al. | |
| 2008/0269890 A1 | 10/2008 | Simpson et al. | |
| 2009/0046349 A1 | 2/2009 | Haddock et al. | |
| 2010/0322059 A1 | 12/2010 | Yasui | |
| 2011/0234974 A1* | 9/2011 | Lawu | G02B 5/1895 351/159.11 |

FOREIGN PATENT DOCUMENTS

| | | |
|---|---|---|
| JP | A-2000-511299 | 8/2000 |
| JP | A-2001-516462 | 9/2001 |
| JP | A-2007-181726 | 7/2007 |
| JP | A-2008-97013 | 4/2008 |
| JP | A-2008-511019 | 4/2008 |
| JP | A-2009-525840 | 7/2009 |
| JP | A-2010-125292 | 6/2010 |
| JP | A-2010-134282 | 6/2010 |
| JP | A-2010-158315 | 7/2010 |
| JP | A-2010-525884 | 7/2010 |
| JP | A-2010-532496 | 10/2010 |
| WO | WO 2008/090743 A1 | 7/2008 |
| WO | 2012/078763 A1 | 6/2012 |

OTHER PUBLICATIONS

Jun. 8, 2015 Extended Search Report issued in European Patent Application No. 12867865.3.

* cited by examiner

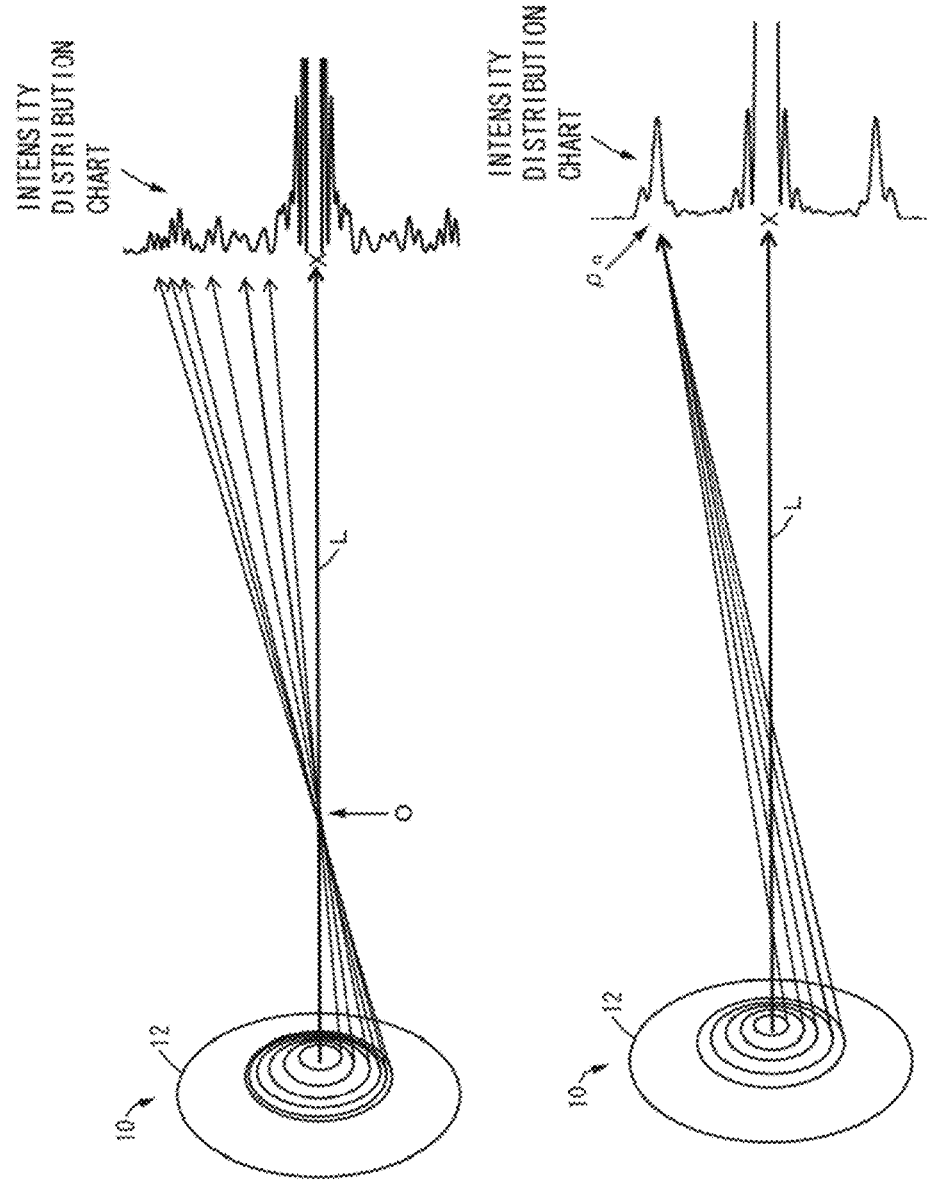

Δr=0.3mm

Δr=0.2mm

Δr=0.4mm

Δr=0.3mm

Δr=0.2mm

Δr=0.4mm

DIFFRACTION-TYPE MULTIFOCAL OPHTHALMIC LENS AND MANUFACTURING METHOD THEREOF

TECHNICAL FIELD

This invention relates to ophthalmic lenses such as a contact lens used for the human eye that exerts correction effect in the human optical system and an intraocular lens, especially to a multifocal ophthalmic lens with a novel diffraction structure, as well as a manufacturing method thereof.

BACKGROUND ART

Conventionally, ophthalmic lenses have been used as optical elements for correction in the human optical system and as alternative optical elements after crystalline lens extraction. Among them, contact lenses applied to the eye and intraocular lenses inserting therein have been used extensively because they provide a wide vision by being directly used for the human eye while reducing the uncomfortable feeling in seeing objects.

Meanwhile, there are increasing number of people in recent years who reached the presbyopic age and continue to wear contact lenses. Since such seniors who suffer from presbyopia have their focal functions deteriorated, they develop a symptom of hardly being able to focus on objects nearby. Therefore, presbyopia patients will need multifocal contact lenses that allow them to focus on nearby objects, too. Also, since patients who underwent a cataract surgery have their crystalline lens removed that used to adjust the vision, they still have symptoms resulting in difficulties in seeing nearby objects even if intraocular lenses are inserted in their eyes. It is becoming necessary for such intraocular lenses to have a multifocal function realized by multiple focal points. Thus, needs for multifocal lenses are increasingly growing in recent years reflecting our aging society.

As methods of producing such multifocal ophthalmic lenses, there have been known a refraction-type multifocal lens that forms multiple focal points based on the refraction principle and a diffraction-type multifocal lens that forms multiple focal points based on the diffraction principle. In the latter mentioned diffraction-type multifocal lens, the optical part of the lens is provided with a plurality of diffraction structures formed concentrically, and multiple focal points are formed by the effect of mutual interference between light waves that pass through said multiple diffraction structures (zones). Therefore, such lenses have an advantage of being able to set a lager lens power while minimizing the lens thickness as compared to refraction-type lenses that generate focal points by the refraction effect of light waves at the refraction interface, which is a boundary of different refractive indices.

Generally speaking, the diffraction-type multifocal lens has a diffraction structure where the pitch of diffraction zones gradually gets smaller as it moves from the center toward the periphery according to a certain rule called 'Fresnel pitch,' and the 0th order diffracted light and first-order diffracted light generated from said structure are used to produce multiple focal points. Usually, the 0th order diffracted light focuses for far vision while the first-order diffracted light focuses for near vision. By providing such a distribution of diffracted light, a bifocal lens can be produced having focal points for far and near visions.

In recent years, needs for a trifocal lens have been pointed out that can provide a focal point not only on the near side but also at an intermediate position between far and near ranges to be used for patients of advanced presbyopia or cataract patient who had the crystalline lens extracted and an intraocular lens inserted. Examples of such a diffraction-type multifocal lens that can generate three focal points include those disclosed in Japanese Unexamined Patent Publication No. JP-A-2010-134282 (Patent Document 1) and Japanese Unexamined Patent Publication No. JP-A-2010-158315 (Patent Document 2) and so forth. Both of these examples are based on the Fresnel pitch rule but their relief configurations in the diffraction zone are varied.

However, the diffraction-type ophthalmic lens has a problem of easily generating multiple concentric circles of light around the light source when the light source is viewed by an eye in the distance at night no matter whether a bifocal lens or a trifocal lens is used. This circle of light usually called 'halo' tends to appear around a point light source such as a street light in the distance or a motor vehicle headlight or the like, which causes a problem of deteriorated visibility at night using the ophthalmic lens. The halo is one of the phenomena reflecting the imaging characteristics of multifocal lenses, especially those called the simultaneous perception-type, and the cause of the halo formation can be explained as follows:

In case of an ideal monofocal lens with no aberration, light from far distance passes through the lens and focuses an image at a given focal point position so as to intensify the amplitude of light waves each other to the maximum extent (FIG. 48A). In that process, the intensity distribution at the image plane shows a simple pattern of a main peak at the center thereof with only very small side lobes defined by the Airy radius existing around it (FIGS. 48B, 48C). FIG. 48C is a magnified view of FIG. 48B. Therefore, when a light source is viewed from far away, an image is formed with no halo that reflects such intensity distribution (FIG. 48D).

Meanwhile, a diffraction-type multifocal lens having two focal points for far and near visions is designed in such a way that the light from far distance produces an image at the far focal point position so as to maximize the amplitude of light waves each other, while intensifying the amplitude of each other at the near focal point position, too. Light from far distance forms the main peak centered around the image plane at the far focal point, whereas light waves intensified each other at the near focal point position diverge thereafter to reach the image plane at the far focal point (FIG. 49A). At a first glance as shown in FIG. 49B, there seems to be only one main peak on the image plane at the far focal point, but as shown in the magnified view of FIG. 49C, a group of small peaks can be observed. As mentioned above, these peaks were formed by the light components focusing at the near focal point to be mixed in the far focal point image plane as a kind of stray light. Thus the intensity of the group of small peaks is very small compared to that of the main peak, but even light with the smallest intensity can be conspicuous in the night environment with dark background, and further, the image can be better detected by the retina with high visual sensitivity to have it perceived as a halo (FIG. 49D). The group of small peaks will hereinafter be referred to as 'side-bands (peaks).'

Other background arts propose a solution to the halo problem addressed regarding the diffraction-type multifocal ophthalmic lens. Japanese Domestic Publication of International Patent Application No. JP-A-2000-511299 (Patent Document 3), for example, discloses a method of smoothly reducing the height of the diffraction zone in the periphery in a diffraction structure composed of one form of diffraction zone called 'echelette' in order to reduce the halo as well as a function that determines the change in height. Said method tries to reduce the amount of energy distributed to the near focal point as it moves toward the periphery and reduce the halo as a result. However, in the background art mentioned above, the amount of energy distributed to the near side needs to be much lowered in order to reduce the halo to an imperceptible level, in which case there is a problem that the visibility of near objects is significantly deteriorated.

Also, Japanese Unexamined Patent Publication No. JP-A-2007-181726 (Patent Document 4) discloses a multifocal ophthalmic lens that blocks or reduces the transmission of blue light and/or near UV light in order to eliminate glare and halo. In such background art, scattering of light is considered to be the cause of the halo and glare, and it is assumed that the halo and glare can be reduced by preventing the transmission of short-wave light that is subject to scattering. However, the halo is attributed more to the intrinsic behavior of light in generating a near focal point rather than the scattering of light, and therefore, the background art does not bring a basic solution to the problem although some ancillary effects can be expected. Also, since the imaging mechanism of the trifocal diffraction-type ophthalmic lens described in the above background art is no different from that of the bifocal lens and it is inevitable to have the light form an image at multiple focal points mixed in the far focal plane as stray light, the problem of halo described above inherently exists. For that reason, there does not yet exist a diffraction-type multifocal lens such as a bifocal or trifocal lens with the halo reduced to a reasonable level.

BACKGROUND ART DOCUMENTS

Patent Documents

Patent Document 1: JP-A-2010-134282
Patent Document 2: JP-A-2010-158315
Patent Document 3: JP-A-2000-511299
Patent Document 4: JP-A-2007-181726

SUMMARY OF THE INVENTION

Problem the Invention Attempts to Solve

This invention offers a diffraction-type multifocal ophthalmic lens with reduced halos, which was found by the studies on the mechanism of halo in an attempt to reduce it and from a solution based on the study results. In addition, this invention offers a diffraction-type multifocal ophthalmic lens having three or more focal points that can be achieved by finding, in the course of identifying the solution, that said diffraction-type multifocal ophthalmic lens has characteristics that can generate multiple focal points not only on the near and far regions but also in the intermediate range.

In addition, the diffraction-type multifocal lens described above provides for easy manufacturing by having a simple diffraction structure as compared to the diffraction structure of the conventional trifocal lenses, and further aims at a manufacturing method of said diffraction-type multifocal ophthalmic lens that allows easier design and manufacturing methods wherein the imaging characteristics can be envisioned in a simple way as opposed to the usual method of using labor-intensive, time-consuming and cumbersome computer simulation.

Means for Solving the Problem

Aspects of the present invention designed to solve the above problems will be described below. The components adopted in each aspect described below are also adoptable in as many combinations as possible.

That is, a first aspect of the present invention provides a diffraction-type multifocal ophthalmic lens having a diffraction structure where a plurality of diffraction zones are formed concentrically on the lens, characterized in that at least one equal-pitch region is provided where pitches of at least two zones among the diffraction zones are made equal.

In the ophthalmic lens with the structure according to the present aspect, pitches of at least two zones among the diffraction zones are made equal. This allows the group of side-band peaks that had been considered the cause of the halo problem to show the regular distribution, which enables to control the form of the halo to the extent not to interfere with visibility at night unlike the conventional diffraction lens with a random distribution of side-band peaks. Although it was hard to formulate the group of side-band peaks for the conventional Fresnel diffraction lens, it is now possible to properly set the position and intensity of the peaks by equalizing the pitches, thus making it possible to implement the design for halo reduction more quickly.

A second aspect of the present invention provides the diffraction-type multifocal ophthalmic lens according to the first aspect, wherein the equal-pitch region is configured by the diffraction zones which are adjacent to each other.

In the ophthalmic lens with the structure according to the present aspect, an equal-pitch region configured by the diffraction zones adjacent to each other is provided. This makes it possible to simplify the formula for specifying and designing the position and intensity of the group of side-band peaks that cause the halo, thus making it possible to specify and design the position and intensity thereof in an easy manner. As a result, a diffraction-type multifocal ophthalmic lens with reduced halos is obtained.

A third aspect of the present invention provides the diffraction-type multifocal ophthalmic lens according to the first or second aspect, wherein the equal-pitch region is configured by the diffraction zones which are not adjacent to each other.

In the ophthalmic lens with the structure according to the present aspect, the equal-pitch region is configured by the diffraction zones which are not adjacent to each other. This makes it possible to simplify the formula for specifying and designing the position and intensity of the group of side-band peaks that cause the halo, thus making it possible to specify and design the position and intensity thereof in an easy manner. As a result, a diffraction-type multifocal ophthalmic lens with reduced halos can be obtained according to the present aspect, too.

A fourth aspect of the present invention provides the diffraction-type multifocal ophthalmic lens according to any one of the first to third aspects, wherein the at least one equal-pitch region comprises a plurality of equal-pitch regions in which the pitches of the diffraction zones are made different among the equal-pitch regions.

According to the present aspect, a plurality of equal-pitch regions are provided with different pitches from each other. This allows to ensure the realization of multiple focal points to be formed by the first-order diffracted light in the diffraction structure together with the reduction of halos. Also, by means of providing the equal-pitch regions with multiple pitches different from each other, the degree of design freedom is enhanced.

A fifth aspect of the present invention provides the diffraction-type multifocal ophthalmic lens according to the fourth aspect, wherein at least two equal-pitch regions are adjacent to each other in the diffraction structure where the equal-pitch regions are provided in which the pitches of the diffraction zones are made different among the equal-pitch regions.

In the ophthalmic lens with the structure according to the present aspect, at least two equal-pitch regions are adjacent to each other. This makes it possible to simplify the formula for specifying and designing the position and intensity of the group of side-band peaks that cause the halo, thus making it possible to specify and design the position and intensity thereof in an easy manner. As a result, a diffraction-type multifocal ophthalmic lens with reduced halos is obtained.

A sixth aspect of the present invention provides the diffraction-type multifocal ophthalmic lens according to the fourth or fifth aspect, wherein at least two equal-pitch regions are provided without being adjacent to each other in the diffraction structure where the equal-pitch regions are provided in which the pitches of the diffraction zones are made different among the equal-pitch regions.

In the ophthalmic lens with the structure according to the present aspect, at least two equal-pitch regions are provided without being adjacent to each other. This enhances the degree of design freedom. Also, a diffraction-type multifocal ophthalmic lens with reduced halos can be obtained in the present aspect.

A seventh aspect of the present invention provides the diffraction-type multifocal ophthalmic lens according to any one of the first to sixth aspects, wherein the diffraction structure has a Fresnel region composed of a periodic structure with a Fresnel pitch and the equal-pitch region.

According to the present aspect, the diffraction structure has a Fresnel region composed of a periodic structure with Fresnel pitches and the equal-pitch region. This allows to ensure the realization of multiple focal points to be formed by the first-order diffracted light in the diffraction structure together with the reduction of halo.

An eighth aspect of the present invention provides the diffraction-type multifocal ophthalmic lens according to the seventh aspect, wherein the Fresnel region is arranged in an inner peripheral portion of the diffraction structure and the equal-pitch region is arranged in an outer peripheral portion thereof.

According to the present aspect, the Fresnel region is arranged in the inner peripheral portion of the diffraction structure and the equal-pitch region is arranged in the outer peripheral portion thereof. This makes it possible to formulate, that is, to design the position and intensity of the group of side-band peaks that are considered to cause the halo while maintaining the focal point position of the important near vision and the light intensity, thus making it possible to reduce the halo.

A ninth aspect of the present invention provides the diffraction-type multifocal ophthalmic lens according to the seventh aspect, wherein the Fresnel region is arranged in an outer peripheral portion of the diffraction structure and the equal-pitch region is arranged in an inner peripheral portion thereof.

According to the present aspect, the Fresnel region is arranged in the outer peripheral portion of the diffraction structure and the equal-pitch region is arranged in the inner peripheral portion thereof. This allows to ensure the realization of multiple focal points to be formed by the first-order diffracted light in the diffraction structure under the environment of brightness ranging from photopic to mesopic vision, making it possible to formulate, that is, to design the position and intensity of the group of side-band peaks that are considered to cause the halo, thus making it possible to reduce the halo.

A tenth aspect of the present invention provides the diffraction-type multifocal ophthalmic lens according to any one of the seventh to ninth aspects, wherein the pitch of the Fresnel region is determined by the following equation:

$$r_n = \sqrt{\frac{\{2(n-1)+g\} \times \lambda}{P_{add}}} \quad \text{[Equation 1]}$$

$n$: Diffraction zone number of the Fresnel region $$g = \frac{P_{add} \times r_1^2}{\lambda}$$

$\lambda$: Wave length $P_{add}$: Addition power in setting a focal point of a first-order diffracted light in the Fresnel region using a focal point position of a 0th order diffracted light as a reference $r_n$: Outer radius of an $n^{th}$ diffraction zone of the Fresnel region $r_1$: Outer radius of a $1^{st}$ diffraction zone of the Fresnel region.

According to the present aspect, assuming that the first-order diffracted light from the Fresnel region focuses for near vision, the focal point position can freely be set for any $r_1$ for such near vision.

An eleventh aspect of the present invention provides the diffraction-type multifocal ophthalmic lens according to any one of the first to tenth aspects, wherein the diffraction structure is composed of diffraction zones expressed by a phase function that determines light phases.

According to the present aspect, since the diffraction zone is expressed by the phase function that determines light phases, it is now possible to simplify the formula for specifying and designing the position and intensity of the group of side-band peaks that cause the halo without reducing the amount of transmitted light as compared to the amplitude modulation-type diffraction structure combining light transmission zones and non-transmission zones, thus enabling simplification and time saving of the computer simulation.

A twelfth aspect of the present invention provides the diffraction-type multifocal ophthalmic lens according to the eleventh aspect, wherein the phase function of the diffraction zone is composed of a blaze-like function.

According to the present aspect, by means of making the phase function of the diffraction zone a blaze-like function, further simplification of the formula is possible for specifying and designing the position and intensity of the group of side-band peaks that cause the halo, thus enabling simplification and time saving of the computer simulation. It also enables more precise manufacturing and more accurate design. In other words, it is made possible to reduce the halo.

A thirteenth aspect of the present invention provides the diffraction-type multifocal ophthalmic lens according to the twelfth aspect, wherein the blaze-like phase function of the diffraction zone is expressed by the following equation:

$$\phi_n(r) = \left(\frac{\phi_n - \phi_{n-1}}{r_n - r_{n-1}}\right) \times r + \left(\frac{\phi_{n-1} \times r_n - \phi_n \times r_{n-1}}{r_n - r_{n-1}}\right) \quad \text{[Equation 2]}$$

$\phi_n(r)$: Phase function $\phi_n$: Phase at a position of an outer radius of the diffraction zone $\phi_{n-1}$: Phase at a position of an inner radius of the diffraction zone $r_n$: Outer radius of the diffraction zone $r_{n-1}$: Inner radius of the diffraction zone.

According to the present aspect, further simplification of the formula is possible for specifying and designing the position and intensity of the group of side-band peaks that cause the halo by means of making the phase function of the diffraction zone a function expressed by Equation 2 above, thus enabling simplification and time saving of the computer simulation. It also enables more precise manufacturing and more accurate design. In other words, it is made possible to reduce the halo.

A fourteenth aspect of the present invention provides the diffraction-type multifocal ophthalmic lens according to any one of the first to thirteenth aspects, wherein, in the equal-pitch region provided with the diffraction zones adjacent to each other, the pitch Δr of the diffraction zones of the equal-pitch region is determined to fall within a range of $\rho_q$ (mm)<|0.006×f (mm)×q| corresponding to a position $\rho_q$ of a q-th order diffracted light (q is an integer except zero) on the focal point image plane of the 0th order diffracted light in the diffraction structure determined by the following equation:

$$\rho_q = \frac{2qf\pi}{k\Delta r} \quad \text{[Equation 3]}$$

Δr: Pitch of the diffraction zones in the equal-pitch region $\rho_q$: Position of the q-th order side-band peak in a radial direction from a center of the focal point image plane of the 0th order diffracted light q: Integer except zero f: Focal length of the 0th order diffracted light k: Wavenumber, $k = 2\pi/\lambda$ (wavelength of light).

According to the present aspect, in the diffraction structure provided with diffraction zones within the equal-pitch region, design of the diffraction structure to reduce the halo can be done more specifically and in more detail by means of setting the position $\rho_q$ on the image plane directly affecting the halo generation within such range, thus making it possible to obtain a diffraction-type multifocal ophthalmic lens with reduced halos as a result.

A fifteenth aspect of the present invention provides the diffraction-type multifocal ophthalmic lens according to any one of the first to fourteenth aspects, wherein the pitch of the diffraction zones of the equal-pitch region is from 0.1 mm to 0.5 mm.

According to the present aspect, by setting the pitch of the diffraction zones within the equal-pitch region from 0.1 mm to 0.5 mm, the first-order diffracted light within said equal-pitch region will not focus at a position significantly away from or close to the 0th order focal point position, thus making it possible to form a focal point at a right position.

A sixteenth aspect of the present invention provides the diffraction-type multifocal ophthalmic lens according to any one of the first to fifteenth aspects, wherein a first-order diffracted light of the equal-pitch region forms multiple focal points.

According to the present aspect, multiple focal points by the first-order diffracted light in the diffraction structure are set in addition to a single focal point by the 0th order diffracted light. This makes it possible, for example, to set the 0th order diffracted light with the diffraction structure of the lens to form a focal point for far vision, while setting one of the multiple focal points of the first-order diffracted light for near vision and one of the remaining focal points for intermediate vision. This enables to obtain good diffraction intensity not only for far and near visions but also for intermediate vision in between, thus making it possible to provide an ophthalmic lens that can provide better intermediate vision.

A seventeenth aspect of the present invention provides the diffraction-type multifocal ophthalmic lens according to the sixteenth aspect, wherein the multiple focal points by the first-order diffracted light in the diffraction structure of the equal-pitch region are generated in response to enlargement of an aperture diameter that determines a range of substantial incidence or emission of light in the lens having the diffraction structure.

According to the present aspect, the multiple focal points by the first-order diffracted light in the diffraction structure of the equal-pitch region are generated in response to enlargement of the aperture diameter that determines the range of substantial incidence or emission of light in the lens having the diffraction structure. Due to such characteristics of the present aspect, it is now possible to set a focal point for intermediate vision using one of the multiple focal points by the first-order diffracted light formed in response to the aperture enlargement. These characteristics are ideal in terms of the relation between the aperture diameter that determines the range of substantial incidence or emission of light and the depth of focus. In other words, when a pupil of the human eye is small, its depth of focus is large enough to substantially cover the intermediate region even in the lens designed to have only two focal points at far and near distances, and it is a highly illuminated outdoor environment under clear sky that causes small pupils and it is so rare to work under such environment using vision to look at a distance equivalent to the intermediate region that there is no need to consider a focal point to be formed in the intermediate region. However, under an environment of standard illuminance such as the case where the working place has been moved to the interior of the office, the pupil radius gets larger and the depth of focus gets deeper, but in the lens of the present invention, the focal point in the intermediate region starts to form in the best timing in response to such transition of conditions.

An eighteenth aspect of the present invention provides the diffraction-type multifocal ophthalmic lens according to the seventeenth aspect, wherein the multiple focal points by the first-order diffracted light in the diffraction structure of the equal-pitch region are generated when the aperture diameter that determines the range of substantial incidence or emission of light in the lens having the diffraction structure is enlarged to 1.5 mm or more.

According to the present aspect, the multiple focal points are formed by the first-order diffracted light in the diffraction structure within the equal-pitch region when the aperture diameter that determines the range of substantial incidence or emission of light in the lens having the diffraction structure is enlarged to 1.5 mm or more. Due to such characteristics of the present aspect, it is now possible to set a focal point for intermediate vision not especially needed in a very bright outdoor environment under clear sky using one of the multiple focal points by the first-order diffracted light formed subsequent to the aperture enlargement to the diameter of 1.5 mm or more, thereby providing better vision not only at far and near distances but also at intermediate distance under a working environment with the standard office illuminance.

A nineteenth aspect of the present invention provides the diffraction-type multifocal ophthalmic lens according to any one of the first to eighteenth aspects, wherein a focal length of the first-order diffracted light in the diffraction structure is set smaller than that of the 0th order diffracted light in the diffraction structure.

According to the present aspect, the focal length of the first-order diffracted light is set smaller than that of the 0th order diffracted light. This allows the focal point of the 0th order diffracted light in the diffraction structure to be set for far vision and the focal point of the first-order diffracted light in the diffraction structure to be set for near vision, for example. Also, in the present aspect, it is possible to make best use of multiple focal points obtained by the first-order diffracted light in the diffraction structure, and for example, one of the multiple focal points by the first-order diffracted light can be set as the focal point for near vision. This allows one of the remaining focal points to be set as a focal point for intermediate vision. Therefore, better diffraction intensity can be obtained not only for far and near visions but also for intermediate vision in between, thus making it possible to offer an ophthalmic lens that can provide better vision in the intermediate distance, too.

A twentieth aspect of the present invention provides the diffraction-type multifocal ophthalmic lens according to any one of the first to nineteenth aspects, wherein the diffraction structure has a Fresnel region composed of a periodic structure with a Fresnel pitch and the equal-pitch region, while at least one of multiple focal lengths by the first-order diffracted light of the equal-pitch region is made larger than a focal length by the first-order diffracted light of the Fresnel region.

According to the present aspect, the diffraction structure has a Fresnel region composed of a periodic structure arranged in plurality with the Fresnel pitch and equal-pitch regions described above. This allows to ensure the realization of multiple focal points formed by the first-order diffracted light in the diffraction structure.

Also according to the present aspect, the focal length of at least one of the multiple focal points formed by the first-order diffracted light in the equal-pitch region is made larger than that of the first-order diffracted light within the Fresnel region. It is now possible, for example, to set the 0th order diffracted light with the diffraction structure of the lens to form a focal point for far vision and to set the first-order diffracted light with the diffraction structure in the Fresnel region to form a focal point for near vision, and further to set one of the multiple focal points formed by the first-order diffracted light with the diffraction structure within the equal-pitch region to form a focal point for intermediate vision. This enables to produce three focal points including the one for intermediate vision while keeping the amount of light for far and near visions that are expected to be used more frequently.

A twenty-first aspect of the present invention provides the diffraction-type multifocal ophthalmic lens according to the twentieth aspect, wherein a focal point of the first-order diffracted light of the equal-pitch region which forms a focal length larger than that of the first-order diffracted light of the Fresnel region is generated when the aperture diameter that determines the range of substantial incidence or emission of light in the lens having the diffraction structure is enlarged to 1.5 mm or more.

According to the present aspect, multiple focal points formed by the first-order diffracted light in the diffraction structure that form larger focal lengths than those of the first-order diffracted light within the Fresnel region are generated when the aperture diameter that determines the range of substantial incidence or emission of light in the lens having the diffraction structure is enlarged to 1.5 mm or more. Due to such characteristics of the present aspect, it is now possible to provide good vision for far and near regions but also for intermediate region under a working environment with the standard office illuminance by means of setting a focal point for intermediate vision not especially needed in a very bright outdoor environment under clear sky using one of the multiple focal points by the first-order diffracted light when the aperture diameter is enlarged to 1.5 mm or more.

Also, in order to carry out the present aspect, two or more diffraction zones constituting the equal-pitch region are preferably provided outside a region of 0.75 mm radius from the central optical axis in the optical part of the lens. Meanwhile, two or more diffraction zones constituting the Fresnel region is to be provided within a region of 0.75 mm radius from the central optical axis in the optical part of the lens and can also be provided beyond a region of 0.75 mm radius.

A twenty-second aspect of the present invention provides a manufacturing method of a diffraction-type multifocal ophthalmic lens having a diffraction structure where a plurality of diffraction zones are formed concentrically on the lens, characterized by forming the diffraction structure composed of an equal-pitch region where pitches of at least two zones among the diffraction zones are made equal.

In the present aspect, by having pitches of at least two zones among the diffraction zones equal to each other, it is now possible to formulate the positions of the group of side-band peaks, which used to be very difficult to design by specifying the position and intensity thereof in the conventional Fresnel diffraction lens, although those peaks were considered to cause generation of the publicly known halos in the diffraction-type lens. Also, as described later, it is now possible to formulate the intensity of the group of side-band peaks, as is the case for the position thereof. In other words, the position and intensity of the group of side-band peaks that cause the halo, a significant problem with the diffraction-type lens, can be designed and produced without conducting any simulation or experiment that is highly labor-intensive and time-consuming.

Effect of the Invention

According to the diffraction-type multifocal ophthalmic lens of the present invention, the inclusion in the diffraction structure of the equal-pitch region where pitches of diffraction zones are equal to each other enables to control the form of the halo to the extent not to interfere with visibility at night and makes it possible to formulate the group of side-band peaks considered to cause the halo, which used to be very difficult to design by specifying the position and intensity of the peaks in the conventional Fresnel diffraction lens, thus making it possible to easily design the peaks by specifying the position and intensity thereof. As a result, a diffraction-type multifocal ophthalmic lens with reduced halos is obtained. Also, by setting multiple focal points formed by the diffracted light in the diffraction structure, it is now possible to provide good vision for far and near distances but also for intermediate distance in between.

BRIEF DESCRIPTION OF THE DRAWINGS

FIGS. 12A and 12B are illustrative diagrams for comparison between optical characteristics of the diffraction structure with equal pitches according to the present invention and the optical characteristics of the diffraction structure with Fresnel pitches.

EMBODIMENTS FOR CARRYING OUT THE INVENTION

For the present invention, the mechanism of the halo phenomenon will first be described for the purpose of reducing it and then some methods of halo reduction will be described based on such mechanism. Subsequently, new imaging characteristics found through such methods will be described and the applicability of those characteristics to multifocal lenses such as a trifocal lens that is increasingly in high demand in recent years will be described. Then, those methods and characteristics will be described in reference to specific embodiments. Prior to the detailed descriptions, the technical terms used in the present invention are defined as follows:

'Amplitude function (distribution)' means a function (distribution) that mathematically describes the characteristics of light as waves, which is specifically expressed by the following Equation 4:

Amplitude function=$\alpha e^{i(\beta x+\gamma)}$ or

Amplitude function=$\alpha \cos(\beta x+\gamma)$ [Equation 4]

x: Variable

α, β, γ: Constant

'Phase' expressed by (βx+γ) in Equation 4 above advances or delays the travel of light. In the present invention, phase is denoted by φ in the unit of radian. For example, one wavelength of light is expressed as 2π radian and a half wavelength as π radian.

'Phase modulation' collectively means a structure or a method provided in a lens that causes a change in the phase of the light incident thereon.

Figure 50:
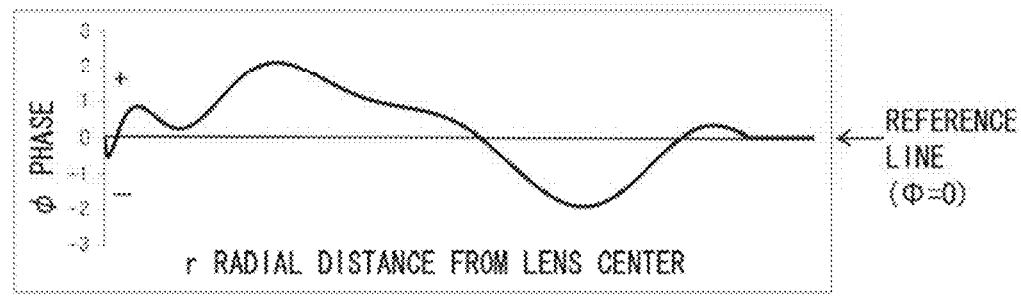
FIG. 50 is a conceptual diagram suitable for explaining the phase profile.

'Phase function' is a more general expression of 'phase' in the exponential or cosine function portion of Equation 4. In the present invention, the term is used to express the lens's phase φ relative to the position r measured from the center of the lens in the radial direction and represented more specifically on the r-φ coordinate plane as shown in FIG. 50. Also, distribution of the phase within the entire frame of the phase modulation structure on said coordinate plane is called the phase profile. The light incident on the lens at φ=0 relative to the datum line of the r-axis when φ=0 means it emits from the lens without changing the phase. If φ takes a positive value relative to the datum line, the travel of light is delayed as much as the phase difference, whereas if φ takes a negative value, the travel of light is advanced as much. In an actual ophthalmic lens, the datum line (plane) is the refracting interface provided with no diffraction structure.

'Optical axis' means a rotationally symmetrical axis of a lens, and refers in this case to an axis that penetrates through the center of the lens extending toward the object space and image space.

'Image plane' means a plane perpendicular to the optical axis at a certain position in the image space where the light incident to a lens emits therefrom.

'0th order focal point' means a focal point position of 0th order diffracted light. In the following paragraphs, the focal point positions of the first and subsequent order diffracted light will be referred to as first-order focal point . . . and so forth.

'0th order focal point image plane' means an image plane at the focal point position of 0th order diffracted light.

The term 'orbicular zone' is used herein as a minimum unit in the diffraction structure. For example, a region where one blaze is formed is called an orbicular zone. It is also called a 'zone.'

Figure 51A:
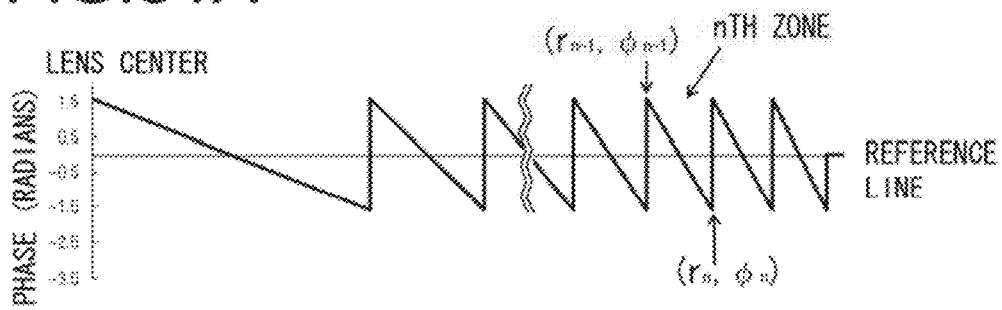
FIGS. 51A-51C are diagrams suitable for explaining the blaze-type phase profile.
Figure 51B:
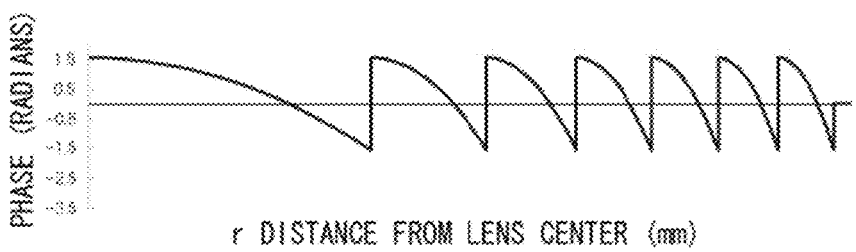
Figure 51C:
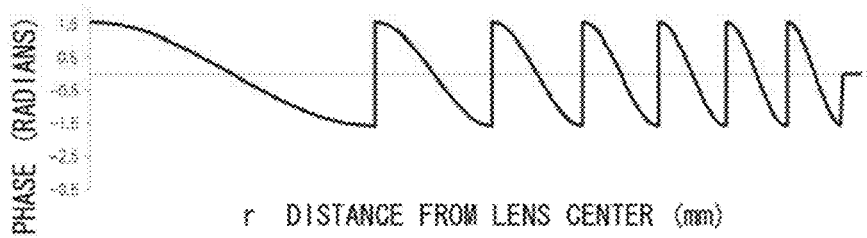
Figure 52:
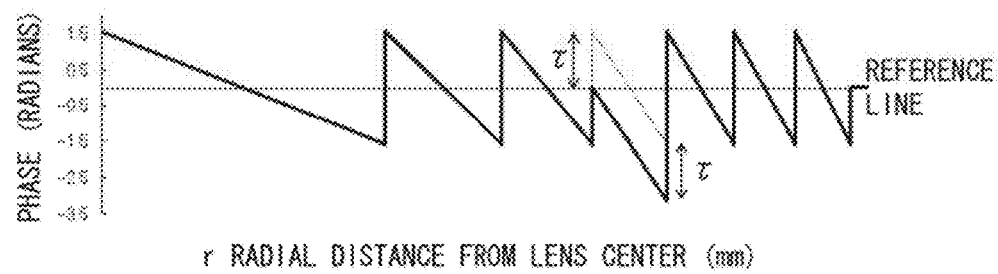
FIG. 52 is a diagram suitable for explaining the phase profile when a phase shift is given to the phase function.

'Blaze' refers to one form of phase function with the phase changing in a roof configuration. In the present invention, the basic blaze is the one shown in FIG. 51A wherein each peak and valley of the graph change linearly in each orbicular zone. The concept of blaze in the present invention also includes the one shown in FIG. 51B wherein the peaks and valleys are connected to change in a parabolic line. It also includes the one shown in FIG. 51C wherein the peaks and valleys are connected to change in a sine curve as well as the ones wherein each peak and valley are connected to change within an interval with no extrema. In the present invention, the blaze of the $n^{th}$ zone is basically set as shown in FIG. 51A, unless otherwise specified, in such a way that the phase $\phi_n$ of the zone's outer radius $r_n$ and the phase $\phi_{n-1}$ of the inner radius $r_{n-1}$ become equal in the absolute values across the datum plane (line), that is, $|\phi_n|=|\phi_{n-1}|$. As shown in FIG. 52, the peaks and valleys of the blaze can be configured by phases $\phi'_{n-1}$ and $\phi'_n$ newly set by means of shifting the phases $\phi_{n-1}$ and $\phi_n$ in the direction of φ-axis at respective positions by the value of the phase shift τ shown in Equation 5 below in reference to the datum line.

$\phi'_n = \phi_n + \tau$ $\phi'_{n-1} = \phi_{n-1} + \tau$ [Equation 5]

τ: Value of phase shift (radian)

'Phase constant' means the constant h defined by Equation 6 below.

$$h = \frac{|\phi_n - \phi_{n-1}|}{2\pi}$$ [Equation 6]

$|\phi_n - \phi_{n-1}|$: Phase difference between the phases of the inner radius and outer radius of the $n^{th}$ diffraction zone.

'Relief' collectively means a microstructure of uneven surface formed on the surface of the lens obtained through a conversion of the phase profile specifically into the lens contours. The specific method of converting the phase profile into the relief configuration is described as follows:

When light enters into a medium with a certain refractive index, its speed is reduced according to the refractive index. The light wavelength changes as much as the change in speed resulting in a phase change. Since a positive phase in the phase profile means reduced speed of light, incident light into a region of high refractive index is equivalent to bringing it to a positive phase. The terms positive and negative phases are relative expressions, and comparing the phases of −2π and −π for example, the latter lags behind the former even with the same sign, thus setting a region of higher refractive index than the former.

If the lens has a blaze-like phase function for example, the actual form of the blazed step is expressed by Equation 7 below. Such a relief configuration can be added to a lens by machining it with a precision lathe or by a molding method.

Blazed step height=$h \times \lambda/(n_s-n_m)$      [Equation 7]

$h$: Phase constant described above
$\lambda$: Wavelength
$n_s$: Refractive index of the lens's base material
$n_m$: Refractive index of the medium facing the lens The intensity distribution is a series of plotted values of the intensity of light that has passed through a lens, which is expressed as conjugate absolute values of the above-mentioned amplitude function. In this case, it is divided into two main categories, 'intensity distribution on the optical axis' and 'image plane intensity distribution.' The former refers to the position of lens as a base point to plot the distribution of intensity of light on the optical axis on the image side, which is used for examining where the focal point is formed on the optical axis and what the intensity of light is. On the other hand, the image plane intensity distribution shows the distribution of light intensity on a certain image plane, which is expressed in the present invention by plotting the values of intensity at the position π in the direction of zero deviation angle of radius vector seen from the center of the image plane. In the human eye, what is perceived on the retina is the intensity distribution on the image plane.

'Fresnel pitch' means one form of pitch of zones determined in accordance with certain rules. In this context, it indicates the pitch determined by Equation 1 assuming that the outer radius of the $n^{th}$ zone is $r_n$.

Generally speaking, the addition power $P_{add}$ (which gives an indication as to where the focal point position for near vision should be set when the 0th order and first-order light are assigned to far and near visions, respectively) corresponding to the focal point of the first order-diffracted light can be set by means of setting the pitch as determined by Equation 1. The diffraction-type lens used in the present invention with Fresnel pitches is different from the Fresnel lens using the refraction principle and refers to a lens using the diffraction principle with the pitches in accordance with the equation above.

Next, the method, conditions and output data of the computer simulation used in the present invention will be described as follows:

As computing software, simulation software was used to be able to calculate intensity distribution and the like based on an integral equation for diffraction. A far point light source was set up as the light source for the calculation assuming that parallel light beams in the same phase enter into the lens. Also, in the calculation, it was assumed that the media both on the object and image sides are vacuum and the lens is an ideal lens having no aberration (light beams passing through the lens form an image at the same focal point regardless of the emitting position of the light). Also, the calculation was performed based on the assumption that the wavelength equals 546 nm and the refractive power of the lens for the 0th order diffracted light (basic refractive power) equals 7D (Diopter).

The intensity distribution on the optical axis was based on plotting of values corresponding to the distance along the optical axis taking the lens as a datum point. Also the image plane intensity distribution was obtained by plotting the intensity values corresponding to the distance in the zero vector direction on the image plane measured from its center. Unless otherwise specified, the vertical scale of the distribution of intensity values on the image plane was considered to be constant. In addition, the real part of the amplitude function was used as the amplitude function in the present invention. Also, the amplitude is shown by plotting the values corresponding to the distance from the center of the image plane in the radial direction as has been done for the image plane intensity distribution.

In the computer simulation of the present invention, the focal point position of 0th order diffracted light is set at 7D (Diopter) (equivalent to the focal length of 142.8 mm). Since the values on the horizontal axis of the image plane coordinate are limited to those of the particular focal point position, a new position of the image plane with a different focal length can be calculated by the conversion using the following Equation 8:

$$\rho' = \frac{f'}{f}\rho \qquad \text{[Equation 8]}$$

$f$: Focal length of 0th order diffracted light used for calculations in the embodiments of the present invention $\rho$: Position in the radial direction measured from the center of the focal image plane of the 0th order diffracted light when focal length = $f$ $f'$: Another focal length $\rho'$: Position in the radial direction measured from the center of the focal image plane of the 0th order diffracted light when focal length = $f'$ The position $\rho'$ of the image plane when the focal length is 16.6 mm (assuming an ideal lens in the ophthalmic optics) can be calculated by the following conversion equation:

$\rho'=(16.6/142.8) \times \rho = 0.1167 \times \rho$ assuming that the position of the image plane in the present embodiment is $\rho$.

Figure 1A:
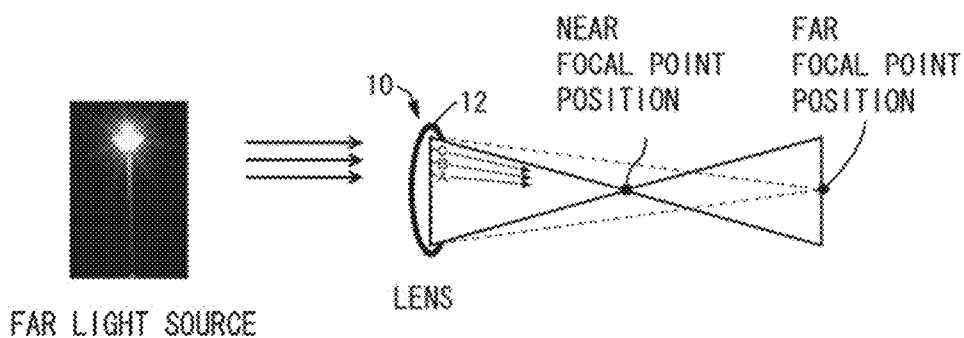
FIGS. 1A-1D are illustrative diagram and graphs showing halo-forming models of a diffraction-type lens.
Figure 1B:
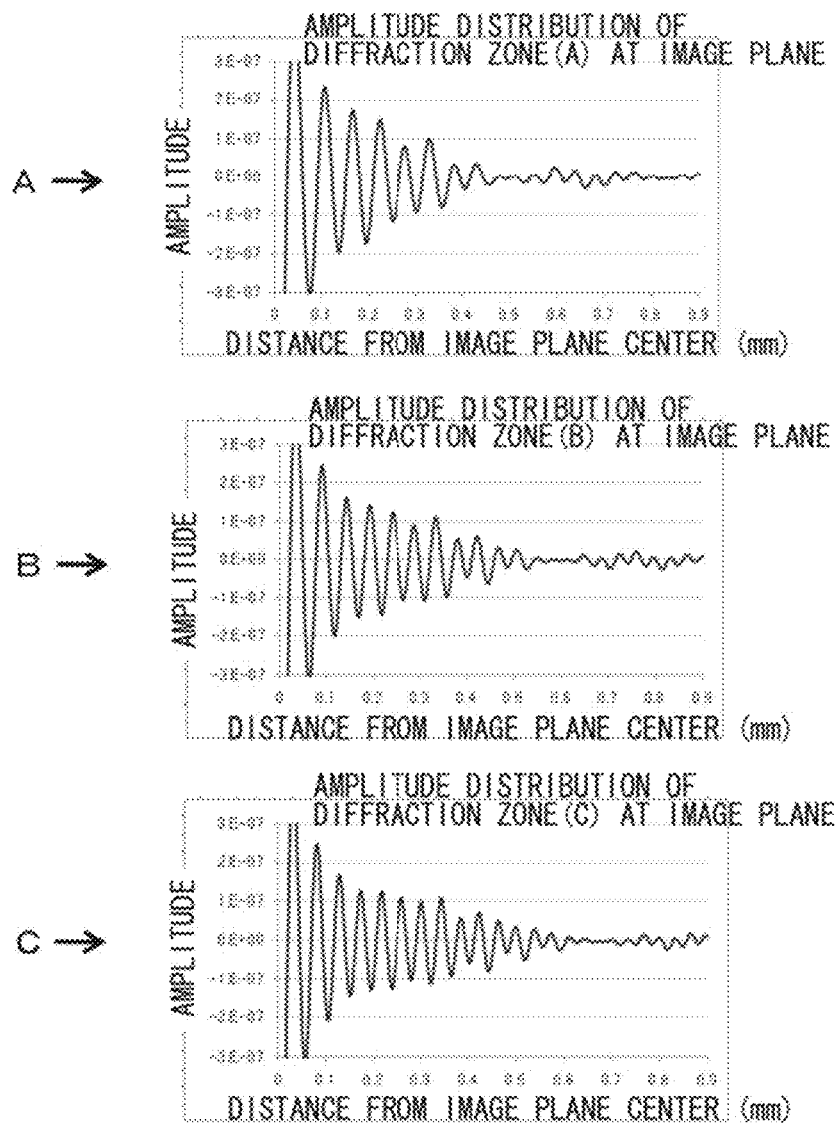
Figure 1C:
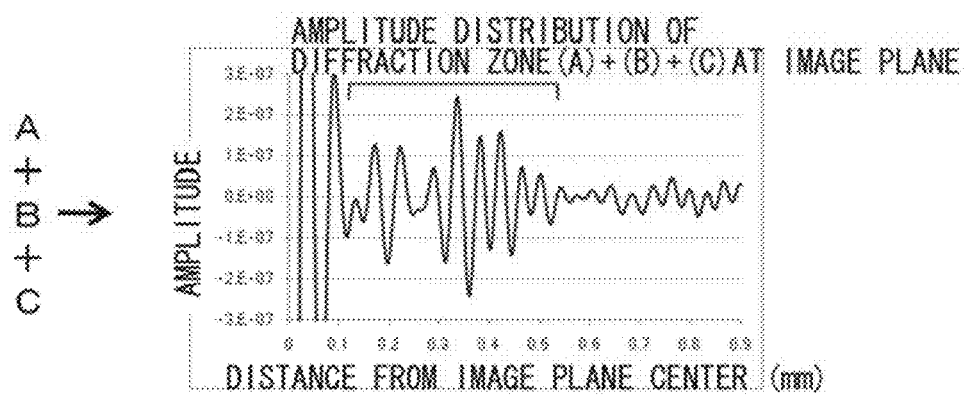
Figure 1D:
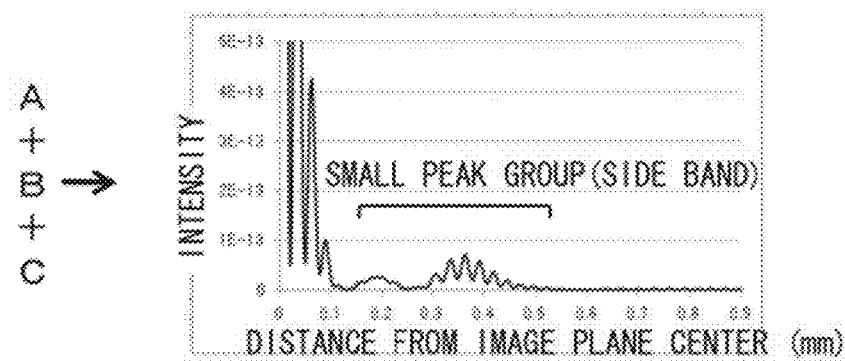

Based on the above definitions, the mechanism of halo formation and the characteristics of lenses with limited extent of halo will be described in the following paragraphs:

As described above, the formation of side-bands on the image plane that causes the halo occurs as a phenomenon of light waves, and as shown in FIG. 1A, the light passing through each diffraction zone exhibits an amplitude distribution reflecting the characteristics of each zone on the image plane of the far focal point. For example, the light passing through each of the zones A, B and C in FIG. 1A forms an amplitude distribution as shown in FIG. 1B. Then, a composite of amplitudes of the light beams from each zone determines the overall amplitude distribution at the image plane of the far focal point (FIG. 1C). The conjugate absolute values of these amplitudes become the intensity of light (FIG. 1D) to be perceived by the eyes as the side-bands described above. Therefore, in order to reduce the halo, it is necessary to capture the information on such amplitude distribution and control those amplitudes.

In designing a diffraction-type lens, multiple focal points are to be made as described above using the diffraction interference effect by giving variations to the amplitude and phase of light created by means of providing concentric zones called 'diffraction zones' to the lens. Especially in designing a diffraction-type multifocal ophthalmic lens, components that can change the light phase are often used. Such a change in phase is determined by the phase function described above. Assuming that the 0th order diffracted light through said diffraction-type lens is used to form a far vision focal point thereof and the phase function of the zone is $\phi_n(r)$, the amplitude function $E_n(\rho)$ of the light reaching the 0th order focal point image plane from the zone having said phase function is expressed by Equation 9 below.

$$E_n(\rho) = E_0 \exp\left[i\left(kf + \frac{k\rho^2}{2f}\right)\right] \times$$

$$\int_0^{2\pi}\int_{r_{n-i}}^{r_n} r \times \exp[i\phi_n(r)] \times \exp\left[-i\frac{k\rho\cos\theta}{f} \times r\right] dr d\theta$$

[Equation 9]

$r$: Position measured from the center of
    lens in the radial direction $\theta$: Angle representing the radius vector on the lens surface $r_{n-1}$: Inner radius of the $n^{th}$ diffraction zone $r_n$: Outer radius of the $n^{th}$ diffraction zone $\phi_n(r)$: Phase function of the $n^{th}$ diffraction zone $\rho$: Position in the radial direction
    measured from the center of the focal
        image plane of the 0th order diffracted light $E_n(\rho)$: Amplitude function from the $n^{th}$ diffraction zone on
    the focal image plane of the 0th order diffracted light $\lambda$: Wavelength
    (herein referring mainly to the design wavelength
        used for designing the diffraction structure)

$k$: Wavenumber. Defined as $k = 2\pi/\lambda$ $f$: Focal length of the 0th order diffracted light $E_0$: Intrinsic amplitude value Since the phase function generally deals with symmetrical components about the lens center, it is good enough to discuss the amplitude function from the line segment region in the radius vector direction of $\theta=0$ in order to obtain information on amplitude function on the image plane. Therefore, the amplitude behavior can be examined using Equation 10 below that determines amplitude of light from the line segment region in the radius vector direction of $\theta=0$ in Equation 9.

$$E_n(\rho) = E_0 \exp\left[i\left(kf + \frac{k\rho^2}{2f}\right)\right] \times$$

[Equation 10]

-continued $$\int_{r_{n-1}}^{r_n} \exp[i\phi_n(r)] \times \exp\left[-i\frac{k\rho}{f} \times r\right] dr$$

$r$: Position measured from the center of
    lens in the radial direction $r_{n-1}$: Inner radius of the $n^{th}$ diffraction zone $r_n$: Outer radius of the $n^{th}$ diffraction zone $\phi_n(r)$: Phase function of the $n^{th}$ diffraction zone $\rho$: Position in the radial direction
    measured from the center of the focal
        image plane of the 0th order diffracted light $E_n(\rho)$: Amplitude function from the $n^{th}$
    diffraction zone on the focal image
        plane of the 0th order diffracted light $\lambda$: Wavelength
    (herein referring mainly to the design wavelength
        used for designing the diffraction structure)

$k$: Wavenumber. Defined as $k = 2\pi/\lambda$ $f$: Focal length of the 0th order diffracted light $E_0$: Intrinsic amplitude value Also, dealing with the blaze-like phase function as indicated in the present invention, such a form of phase function can be expressed by a linear first-order equation such as Equation 2. In this case, Equation 10 becomes integrable and expressed by the formula of Equation 11. Only the real part of the amplitude function is denoted herein.

$$E_n(\rho) = E_0 \cos\left\{\frac{k\rho^2 - k(r_n + r_{n-1})\rho}{2f} + \frac{\phi_n + \phi_{n-1}}{2} + kf\right\} \times$$

$$\operatorname{Sinc}\left\{\frac{\phi_n - \phi_{n-1}}{2} - \frac{k(r_n - r_{n-1})\rho}{2f}\right\} \times (r_n - r_{n-1})$$

[Equation 11]

$r$: Position measured from the center of
    lens in the radial direction $r_{n-1}$: Inner radius of the $n^{th}$ diffraction zone $r_n$: Outer radius of the $n^{th}$ diffraction zone $\phi_n(r)$: Phase function of the $n^{th}$ diffraction zone $\rho$: Position in the radial direction
    measured from the center of the focal
        image plane of the 0th order diffracted light $E_n(\rho)$: Amplitude function from the $n^{th}$
    diffraction zone on the focal image
        plane of the 0th order diffracted light $\lambda$: Wavelength
    (herein referring mainly to the design wavelength
        used for designing the diffraction structure)

Figure 2A:
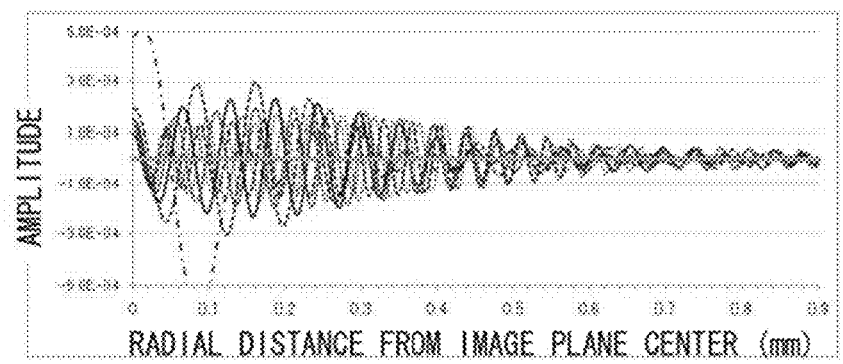
FIGS. 2A-2C are graphs of the amplitude function of light reaching the 0th order focal point image plane from each Fresnel zone, and the intensity distribution chart thereof.
Figure 2B:
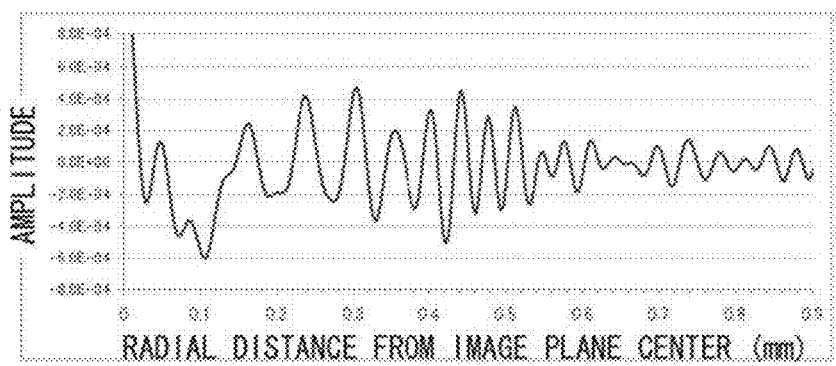
Figure 2C:
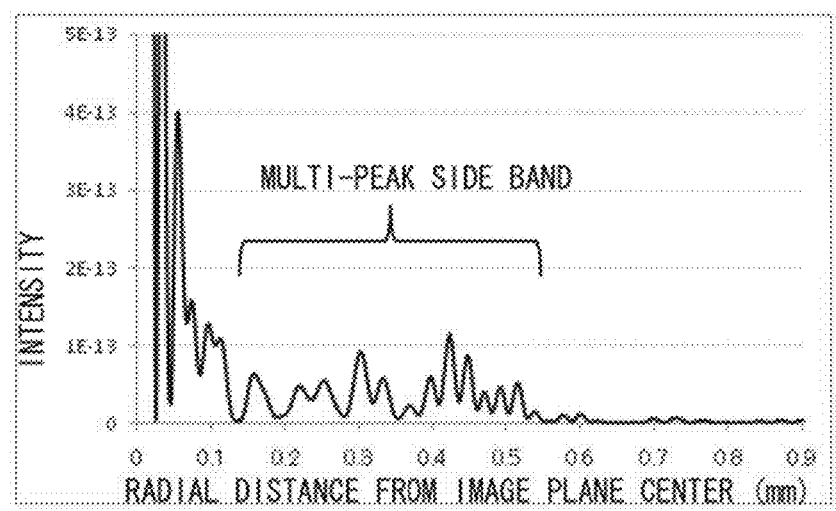

$k$: Wavenumber. Defined as $k = 2\pi/\lambda$ $f$: Focal length of the 0th order diffracted light $E_0$: Intrinsic amplitude value Equation 11 is used as a base formula for the amplitude function corresponding to the blaze-like phase function, and a method of designing the diffraction structure with reduced halos will be described in reference to such equation. First of all, in order to describe the characteristics of the present invention, the characteristics of the halo of the diffraction-type lens having Fresnel pitches that has been used as a common method for designing the diffraction-type multifocal lens will be described in reference to Comparative Example 1 of the first embodiment. Comparative Example 1, as shown in Table 2 and FIG. 8 to be described later, has seven diffraction zones composed of Fresnel pitches, and the phase constant h of each zone is set constantly at h=0.5. As shown in FIG. 2A, the amplitude function of the light reaching the 0th order focal point image plane from each Fresnel pitch zone exhibits amplitudes and periods that are anharmonic between each amplitude function. A composite of these amplitudes show a random distribution as shown in FIG. 2B, and as a result, tends to expand over a wide range toward the periphery from the center of the image plane, which is likely to become a collective group of peaks that are multi-peak and continuous (FIG. 2C). This is because no harmonic amplitude or period is formed between the amplitude functions of the light from each zone with Fresnel pitches focusing on the 0th order focal point image plane.

Figure 10A:
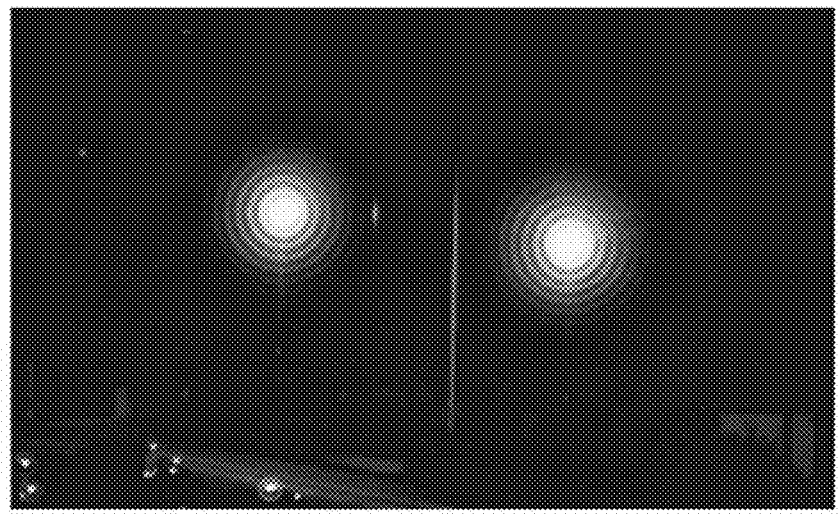
FIGS. 10A and 10B are actual photos of halos of the present embodiment to compare with those of Comparative Example 1.
Figure 10B:
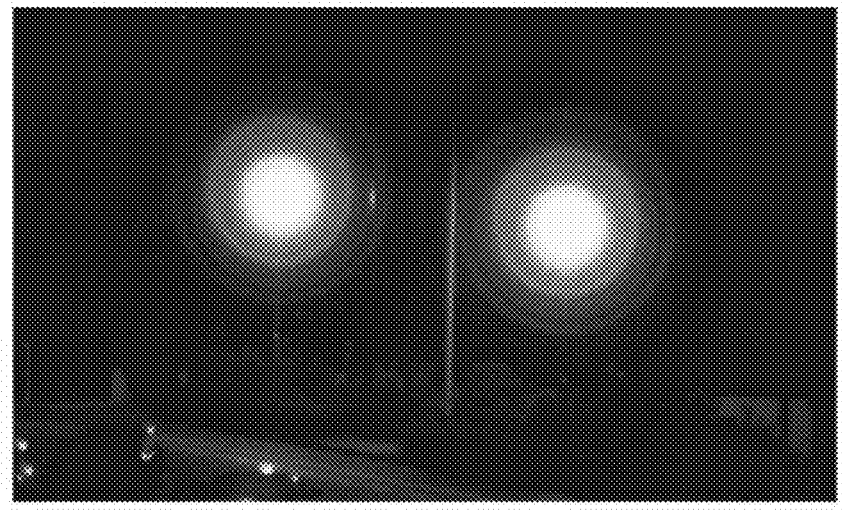

When the diffraction-type multifocal lens with such intensity distribution is used as an ophthalmic lens such as contact lens or intraocular lens, a plurality of broad and planar halos are formed around the headlights of an oncoming vehicle at night for example, posing a risk of not being able to visually recognize the pedestrians and bikers hidden behind them (FIG. 10B described later). As apparent from the above description, the conventional Fresnel pitch lens is considered to have a problem of generating extensively planar halos by making the amplitude distribution that causes the halo a random distribution so that designing the diffraction structure avoiding such multi-peak distribution is deemed effective in reducing the halo.

Let's take a look at any two of the zones in the diffraction-type lens having the blaze-like phase function. Now if the $j^{th}$ and $m^{th}$ zones have equal pitches with the same phase constant for both of them at h, the sine function in Equation 11 for both zones turn out to be the same. Therefore, the behavior of the composite amplitude in each zone can be expressed as a sum of cos function of each amplitude function. Judging from the composite amplitude of the two amplitude functions, it turns out that the amplitudes strengthen each other at the position $\rho_q$ of the image plane expressed in Equation 12 below.

$$\rho_q = \frac{4qf\pi}{kR} \quad [\text{Equation 12}]$$

$$R = (r_m + r_{m-1}) - (r_j + r_{j-1})$$

$\rho_q$: Position of $q$-$th$ order side-band peak in the radial direction measured from the center of focal image plane of 0th order diffracted light $q$: Integer except zero $f$: Focal length of 0th order diffracted light $k$: Wavenumber, $k = 2\pi/\lambda$ (wavelength of light)

$r_{j-1}$: Inner radius of $j$-$th$ diffraction zone

-continued $r_j$: Outer radius of $j$-$th$ diffraction zone $r_{m-1}$: Inner radis of $m$-$th$ diffraction zone $r_m$: Outer radius of $m$-$th$ diffraction zone Assuming that equal pitch zones with the pitch Δr exist continuously to make one region, the relation in Equation 13, below always holds between adjacent zones in such a region, and therefore, it turns out that the amplitudes strengthen each other at the position $\rho_q$ of the image plane expressed in Equation 3 in the region where a plurality of equal-pitch zones exist continuously.

$$R = (r_m + r_{m-1}) - (r_j + r_{j-1}) = 2\Delta r \quad [\text{Equation 13}]$$

Figure 3A:
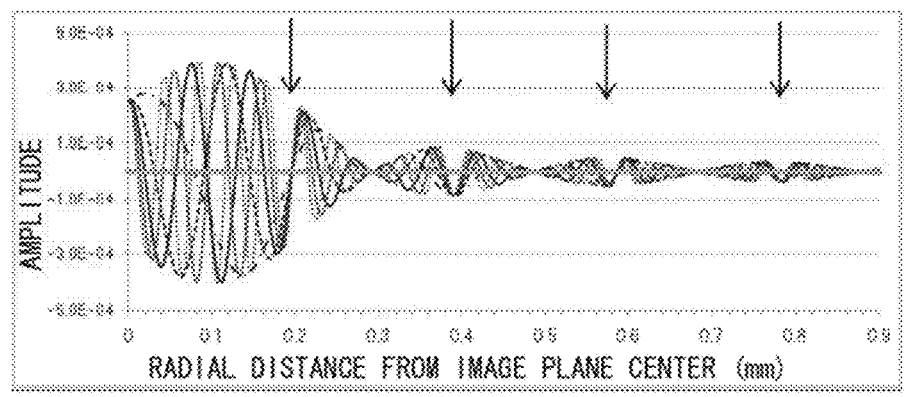
FIGS. 3A-3C are graphs of the amplitude function of light reaching the 0th order focal point image plane from each equal pitch zone, and the intensity distribution chart thereof.
Figure 3B:
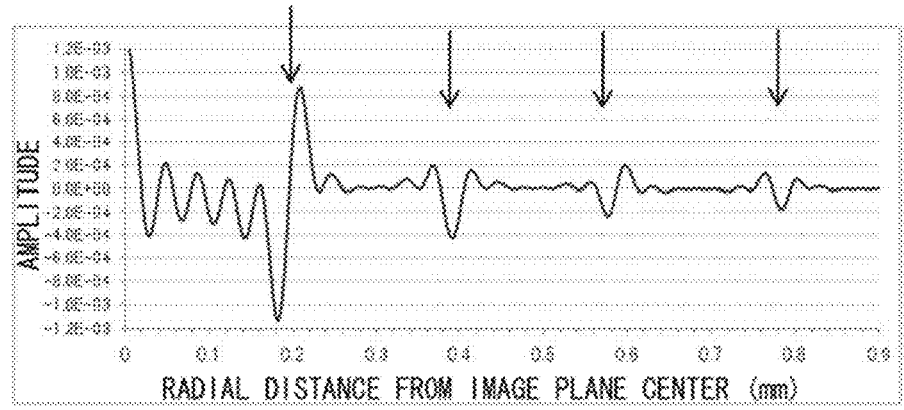
Figure 3C:
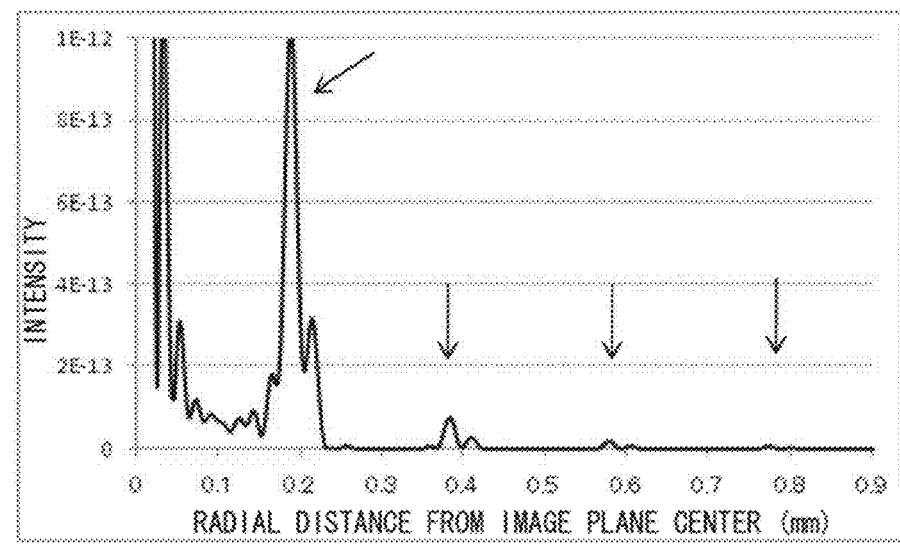

$r_{j-1}$: Inner radius of j-th diffraction zone $r_j$: Outer radius of j-th diffraction zone $r_{m-1}$: Inner radius of m-th diffraction zone $r_m$: Outer radius of m-th diffraction zone Δr: Pitch of diffraction zones in the equal-pitch region FIGS. 3A and 3B show examples of the amplitude function in the region of equal-pitch zones and the composite amplitude function. As shown in Table 1 and FIG. 7 described later regarding an example of diffraction structure having an equal-pitch region, each pitch Δr of five diffraction zones is made equal at 0.4 mm in the diffraction structure where the phase constant is fixed at h=0.5. As evident from FIGS. 3A and 3B, the distribution of amplitudes composed of equal-pitch zones exhibits specific mutual wave interference wherein the amplitudes strengthen each other at each point (marked by arrows) in FIG. 3 while the amplitudes cancel each other to make the curve flatter in the other regions. Also, the intensity distribution reflects the amplitude distribution wherein sharp peaks appear at the points of mutual strengthening of amplitudes gradually attenuating as they move away from the center of the image plane, which shows an intensity distribution quite different from the case of Fresnel pitch where no noise is made in regions other than the peak positions (FIG. 3C).

Since the Fresnel pitch type lens exhibits a side-band distribution with a series of peaks while the equal-pitch type shows local peaks away from each other, the latter forms bright and dark halo rings, not the extensively planar halos like those of the former. In such a case of halo rings, an object within the halo can be visually perceived from between the rings so that the problem of planar halos that hide the entire area can be alleviated, thus resulting in the prevention of the problem of the former with deteriorated visibility at night.

In order to further discuss the specifics of the present invention, embodiments thereof will be described below in reference to the drawings.

Figure 4:
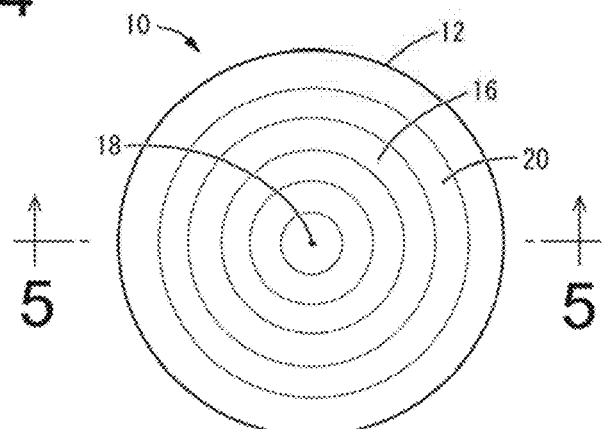
FIG. 4 is a rear specific view of a contact lens as a first embodiment of the present invention.
Figure 5:
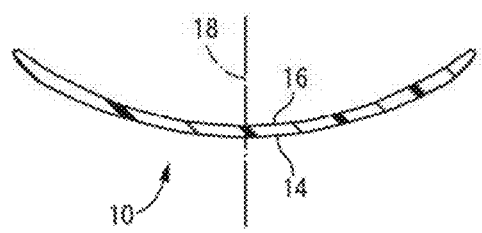
FIG. 5 is a cross sectional specific view of the contact lens of FIG. 4 taken along line 5-5 of FIG. 4.

First, FIG. 4 shows a schematic rear view of an optical part 12 of an ophthalmic lens 10, which is a contact lens as a first embodiment relating to the diffraction-type multifocal ophthalmic lens of the present invention, and FIG. 5 shows a schematic cross section of the optical part 12 of the same ophthalmic lens 10.

The ophthalmic lens 10 has a broad region at its center as the optical part 12, and the publicly known peripheral and edge portions are formed outside thereof. Also, the optical part 12 is formed as a whole with an optical part front surface 14 having a convex face in an approximate shape of a crown and an optical part back surface 16 having a concave face in approximately the same shape. And the optical part 12 of the ophthalmic lens 10 is made as a whole in an approximate form of a bowl with its center slightly thinned if it is to be used for correcting myopia or slightly swollen if it is to be used for correcting hyperopia, both being made into a solid of revolution about a lens central axis 18 as a geometric axis. Such ophthalmic lens 10 is directly worn on the cornea of the eye. Therefore, the diameter of the optical part 12 of the ophthalmic lens 10 is preferably set to about 4 to 10 mm.

The optical part 12 of the ophthalmic lens 10 uses the optical part front surface 14 and the optical part back surface 16 as refracting interfaces. And a given focal length is set for the refracting light (0th order diffracted light) through the optical part front surface 14 and the optical part back surface 16, with a far focal point provided in the present embodiment.

As materials to form the ophthalmic lens 10, publicly known resin materials composed of various polymerizable monomers with optical properties such as light transmissivity or gel-like synthetic polymer composites (hydrogel) are preferably used, and more specifically, polymethylmethacrylate (PMMA), polyhydroxyethylmethacrylate (Poly-HEMA) etc. can be quoted as examples.

Then, especially in the optical part back surface 16 of the present embodiment, a diffraction structure 20 is formed in equal pitches. The diffraction structure 20 is formed concentrically in plurality around the lens central axis 18 and comprises a blaze-like relief 21, which are contours in the radial direction extending continuously in an annular form in the circumferential direction of the lens. In the present embodiment, a focal point with a shorter focal length than the far focal length is given by the first-order diffracted light in the diffraction structure 20. As described above, the individual diffraction structure 20 is called a zone (diffraction zone) or an orbicular zone.

Figure 6A:
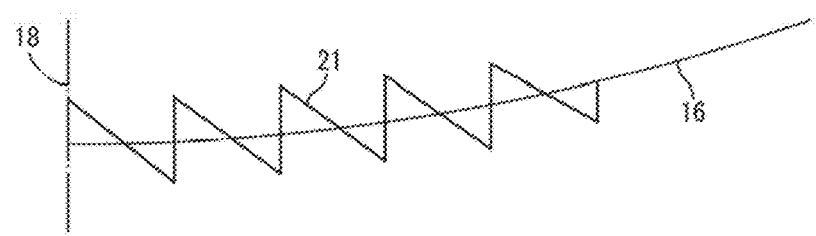
FIGS. 6A and 6B are cross sectional specific views suitable for explaining the relief configuration formed on the back surface of the contact lens shown in FIG. 4.

FIG. 6A shows a magnified cross section of the relief 21 on the optical part back surface 16. The size of the relief 21 is exaggerated for better understanding in FIGS. 6A and 6B. As shown in FIG. 6A, the relief 21 is shaped like stairs going up to the right reflecting the original configuration of the optical part back surface 16 of the ophthalmic lens 10. When the front and back surfaces of the optical part of the ophthalmic lens are made to have a single refractive power, there should be no problem to understand that the optical part back surface 16 is the datum line for the r–φ coordinate plane (FIG. 50) defined above. Also in FIG. 6A, the region below the boundary of the relief 21 is made of a contact lens base material and the upper region is made of an external medium. For better understanding, the shape of the relief 21 will be examined hereinafter without considering the original configuration on the optical part back surface 16 of the ophthalmic lens 10, that is, using the optical part back surface 16 as a linear x-coordinate in the radial direction as shown in FIG. 6B.

Figure 6B:
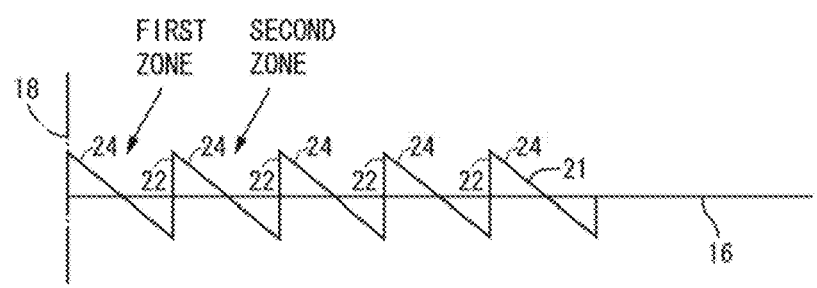

As shown in FIG. 6B, the relief 21 extends concentrically around the lens central axis 18, while being made with contours having ridge lines 22 protruding outward of the ophthalmic lens 10 (upward in FIGS. 5 and 6A, 6B) and valley lines 24 protruding inward of the same (downward in FIGS. 5 and 6A, 6B).

In the descriptions below, 'grating pitch' means a dimension between the ridge line 22 and the valley line 24 in the radial direction. 'Orbicular zone' or 'zone' means the area between the ridge line 22 and the valley line 24 and each zone is assigned a zone number starting from 1 for the central zone followed by 2, 3, and so forth. Also, 'zone radius' means an outer radius of each zone, that is, a radius of the ridge line 22 or the valley line 24 in each zone located outside the concentric center (lens central axis 18 in the present embodiment) measured from said concentric center. Therefore, 'grating pitch' means a width of each zone in the radial direction, and a grating pitch of a particular zone refers to a difference in radius between the zone and another zone with one less number. The diffraction structure composed of blaze-type relief configuration was described above together with specific examples of a contact lens, but in the descriptions below, the phase function or phase profile on which the design of the relief is based on will be used to explain the diffraction structure. Therefore, unless otherwise noted, the phase profile as a diffraction structure will hereinafter be displayed on the r–φ coordinate plane shown in FIG. 50.

Figure 7:
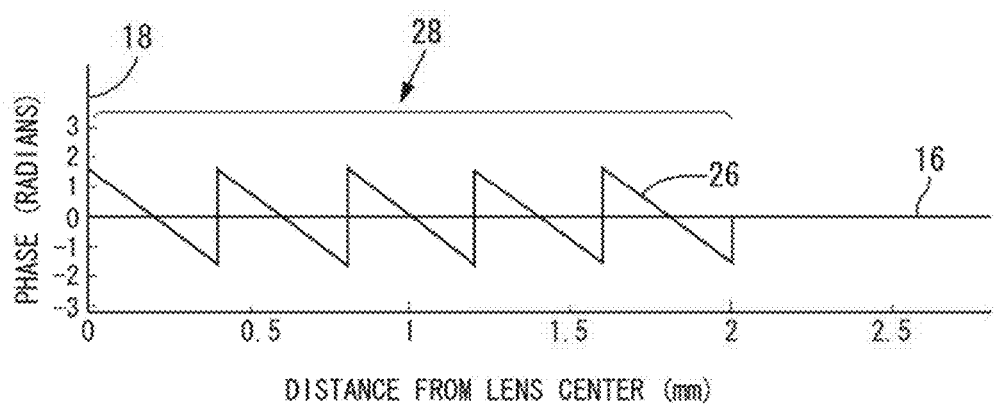
FIG. 7 is a phase profile of the first embodiment of the present invention.
Figure 8:
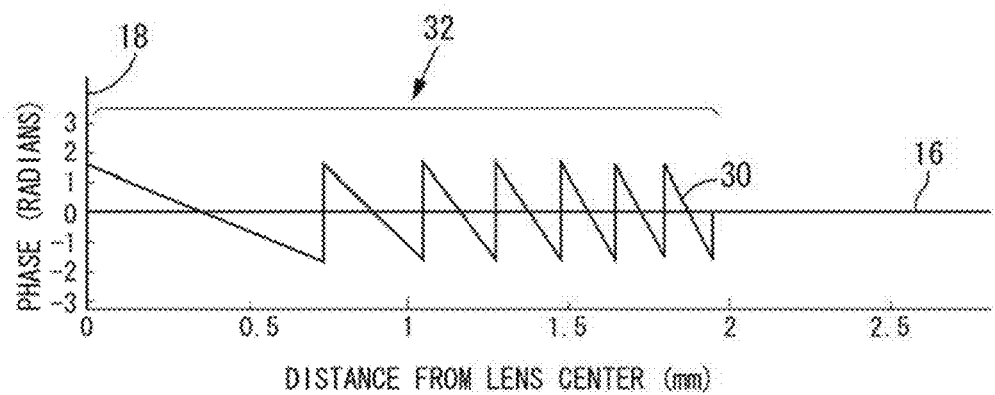
FIG. 8 is a phase profile of Comparative Example 1.

FIG. 7 shows a phase profile 26 with each zone composed of the blaze-like phase function as a first embodiment of the present invention. FIG. 8 shows a magnified cross section of the configuration of a Fresnel zone plate (a phase profile 30) as Comparative Example 1. The phase profile 26 in the present embodiment is provided only on the optical part back surface 16 of the ophthalmic lens 10 and is composed of an equal-pitch region 28 made of a periodic structure with equal pitches where the grating pitches of the diffraction structure 20 arranged in plurality are formed in equal widths. Also, in the phase profile 30 of Comparative Example 1, all the grating pitches of the diffraction structure arranged in plurality are formed in Fresnel pitches, which constitutes a Fresnel region 32 composed of a periodic structure of Fresnel pitches, that is, a Fresnel zone plate. As described above, the present embodiment is set up in such a way that all pitches of five diffraction zones are equalized at $\Delta r=0.4$ mm and the phase constant is fixed at $h=0.5$. Also, Comparative Example 1 is composed of Fresnel pitches wherein seven diffraction zones are given addition power at $P_{add}=2$ (Diopter) and the phase constant of each zone is fixed at $h=0.5$. Table 1 shows the detail of the phase profile 26 of the present embodiment, and Table 2 shows the detail of the phase profile 30 of the comparative example.

TABLE 1

| Zone No. | Zone radius | | Phase | | | |
| | $r_n$ (mm) | $r_{n-1}$ (mm) | $\phi_n$ (radian) | $\phi_{n-1}$ (radian) | Phase constant h | Pitch |
| --- | --- | --- | --- | --- | --- | --- |
| 1st zone | 0.4 | 0 | −1.5708 | 1.5708 | 0.5 | $\Delta r =$ |
| 2nd zone | 0.8 | 0.4 | −1.5708 | 1.5708 | 0.5 | 0.4 mm |
| 3rd zone | 1.2 | 0.8 | −1.5708 | 1.5708 | 0.5 | |
| 4th zone | 1.6 | 1.2 | −1.5708 | 1.5708 | 0.5 | |
| 5th zone | 2.0 | 1.6 | −1.5708 | 1.5708 | 0.5 | |

TABLE 2

| Zone No. | Zone radius | | Phase | | | |
| | $r_n$ (mm) | $r_{n-1}$ (mm) | $\phi_n$ (radian) | $\phi_{n-1}$ (radian) | Phase constant h | Pitch |
| --- | --- | --- | --- | --- | --- | --- |
| 1st zone | 0.738918 | 0 | −1.5708 | 1.5708 | 0.5 | Fresnel pitch |
| 2nd zone | 1.044988 | 0.738918 | −1.5708 | 1.5708 | 0.5 | |
| 3rd zone | 1.279844 | 1.044988 | −1.5708 | 1.5708 | 0.5 | |
| 4th zone | 1.477836 | 1.279844 | −1.5708 | 1.5708 | 0.5 | |
| 5th zone | 1.652271 | 1.477836 | −1.5708 | 1.5708 | 0.5 | |
| 6th zone | 1.809972 | 1.652271 | −1.5708 | 1.5708 | 0.5 | |
| 7th zone | 1.954994 | 1.809972 | −1.5708 | 1.5708 | 0.5 | |

Figure 9A:
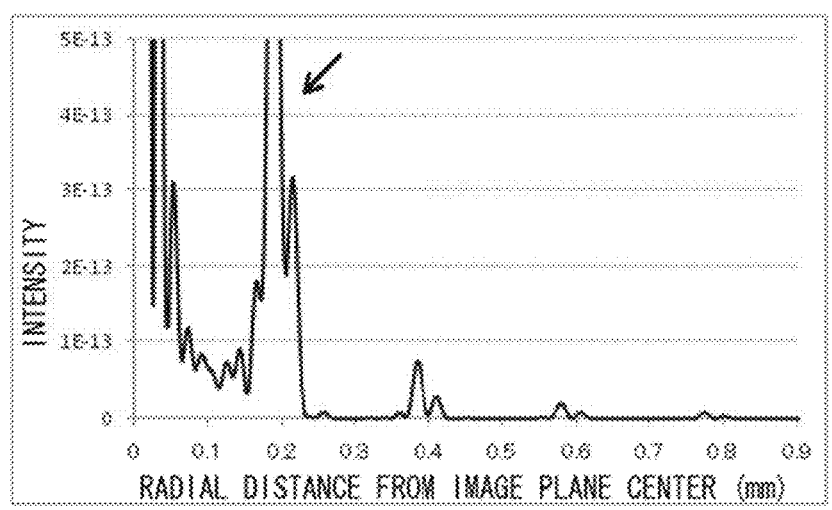
FIGS. 9A and 9B are graphs for comparing a result of simulation of intensity distribution with that of Comparative Example 1 on the image plane at the focal point position of 0th order diffracted light of the present embodiment.
Figure 9B:
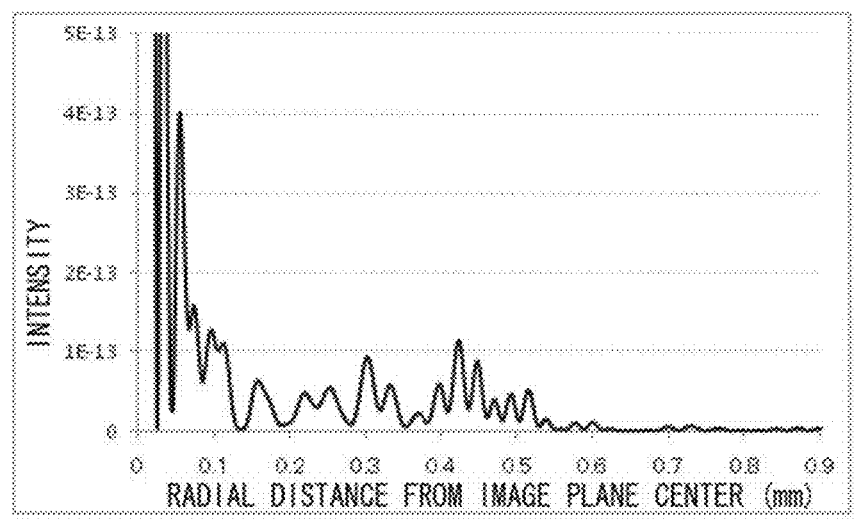

FIGS. 9A and 9B show results of computer simulation of the image plane intensity distribution at the focal point position of 0th order diffracted light of the present embodiment as compared to Comparative Example 1. These results are those of the calculation of the entire area where each diffraction zone shown in the above tables exists. The same will apply to the calculations of the image plane intensity distribution under other embodiments described later.

FIGS. 10A and 10B shows actual photos of light sources at far distance used for contact lenses actually provided with the diffraction structure of the phase profile under the present embodiment as compared to Comparative Example 1. The contact lenses manufactured as a prototype this time are hydrogel soft contact lenses with the water content of 37.5% mainly composed of 2-hydroxyethyl methacrylate with the lens diameter of 14 mm, the optical part diameter 8 mm, and the base curve at 8.5 mm on the optical part back surface 16. To take actual photos of halos at night, the prototype contact lenses were soaked in physiological saline filled in a glass cell, which were placed in front of the camera lens to take night photos of the light source at far distance. The photos were taken under the condition of open aperture of the camera lens assuming the situation where the pupil diameter is increased during night hours. Since the conditions of the prototype contact lenses to be taken in photos and the image shooting conditions are the same as those of this time, they are omitted hereinafter.

The image plane intensity distribution under the first embodiment of the present invention shows small peaks appearing at constant intervals, but only one of them is conspicuous at $\rho=0.195$ mm near the center of the image plane (an arrow in FIG. 9A) and other peaks rapidly reduce their intensity across the periphery of the image plane, while intensity distribution, making almost no noise is displayed in other regions. The positions where those peaks appear coincide well with the positions $\rho_1=0.195$ mm, $\rho_2=0.39$ mm and $\rho_3=0.585$ mm . . . that can be obtained by assigning a value of $\Delta r=0.4$ mm in Equation 3, which are found to agree well with the positions actually calculated from the intensity distribution. Meanwhile, the image plane intensity distribution of the comparative example (FIG. 9B) is found to be formed with the side-band peaks in a multi-peak form in a wide range around the image plane. Comparing such theoretical calculation results (FIGS. 9A and 9B) and the actual photos of halos at night (FIGS. 10A and 10B), for both the present embodiment (FIGS. 9A and 10A) and Comparative Example 1 (FIGS. 9B and 10B), the actually observed configurations of halos match well with the image plane intensity distribution, and in the present embodiment, some halo rings reflecting the image plane intensity distribution are observed at constant intervals. Meanwhile, extensively planar halos were observed in Comparative Example 1 as if they reflect the multi-peak intensity distribution. Since the halos are extensively planar in Comparative Example 1, any object existing near the light source is hidden behind the halo posing a risk of not being able to visually recognize the object. Since the halo is not bright enough as a whole and does not take a planar shape or an extended form in the first embodiment, it is found possible to prevent deterioration of visibility as shown in Comparative Example 1.

Thus, the important thing in the present invention, that is, the diffraction structure 20 containing a diffraction zone with equal pitches, is to generate an intensity distribution with side-band peaks locally appearing in a regular manner and almost no amount of light in other regions. In other words, as shown in FIGS. 9A and 10A, the halo is structured with string-like rings leaving other regions with images with no halo, and as shown in FIGS. 9B and 10B, the halo does not appear extensively planar. Due to these superior characteristics of the diffraction-type lens having an equal-pitch region, problems of the diffraction structure 20 composed of diffraction zones with Fresnel pitches, that is, the problem of not being able to visually recognize the pedestrians and bikers hidden behind the broad and planar halos formed around the headlights of an oncoming vehicle during night driving, or deteriorated visibility of traffic lights due to excessive blurring around the light source can be solved.

The diffraction-type lens containing an equal-pitch region has the side-band peaks on the focal point image plane of the 0th order diffracted light localized in certain areas and have different characteristics from the Fresnel pitch type lens which has rapidly decreasing intensity of the peaks across the periphery of the image plane, but it also has design advantages such that the position of such side-band peaks and their intensity can easily be estimated. Since the expanse and brightness of the halo are considered to be proportionate to the distribution and intensity of the side-band peaks, understanding the configuration of the halo quantitatively in the design stage brings great convenience in designing diffraction-type lenses.

First of all, the position where the side-band peaks appear, which is correlated to the expanse of halos, can be controlled by the pitch $\Delta r$ of diffraction zones in the equal-pitch region according to Equation 3. For example, the appearance positions of the side-band peaks when the pitch $\Delta r$ of diffraction zones in the equal-pitch region is set at 0.2 mm and 0.4 mm are as shown in Table 3 below. Table 3 indicates that the appearance interval is larger when $\Delta r=0.2$ mm, and the peaks of the former case appear at twice the frequency as those of the latter. In other words, the smaller $\Delta r$ is, the more extended the peak positions are toward the periphery on the image plane. From this point of view, keeping the pitches large enough is advantageous in restricting the halo expansion, but since the halo can affect the visibility not only by its expanse but also by its brightness, information on the halo brightness is essential in addition to information on the position of the peaks. Since the halo brightness is considered to be proportionate to the side-band intensity, it is important to understand the relation among a group of parameters that give impact on the side-band intensity.

TABLE 3

| Position of side-band peaks | q | $\Delta r = 0.2$ mm | $\Delta r = 0.4$ mm |
|---|---|---|---|
| $\rho_1$ | 1 | 0.39 mm | 0.195 mm |
| $\rho_2$ | 2 | 0.78 mm | 0.39 mm |
| $\rho_3$ | 3 | 1.17 mm | 0.585 mm |
| $\rho_4$ | 4 | 1.56 mm | 0.78 mm |
| $\rho_5$ | 5 | 1.95 mm | 0.975 mm |
| $\rho_6$ | 6 | 2.34 mm | 1.17 mm |

In the diffraction-type lens containing an equal-pitch region, the pitch $\Delta r$ of diffraction zones and the number of constituent zones and the intensity of side-band peaks can be expressed by a simple equation. Now, if the phase constant h of the blaze in the equal-pitch region is fixed, the side-band peak intensity corresponding to a certain order q is expressed by Equation 14 below. By using such an equation, relative changes of intensity between different $\Delta r$ can easily be found.

$$I_s = a \times \{n-(m-1)\} \times \{n^2-(m-1)^2\} \times (\Delta r)^4 \qquad \text{[Equation 14]}$$

$I_s$: Intensity of side-band peak
a: Proportionality constant
n: The last diffraction zone number forming the equal-pitch zone m: The first diffraction zone number forming the equal-pitch zone Δr: Pitch of diffraction zones in the equal-pitch region Table 4 shows, as an example, results of intensity calculations using Equation 14 when Δr 0.2 mm and Δr=0.4 mm are applied, as shown in Table 3 above, to the entire diffraction zone.

TABLE 4

| Range of region (radius mm) | Δr = 0.2 mm | | Δr = 0.4 mm | |
|---|---|---|---|---|
| | Number of constituent zones | Intensity Equation (13) | Number of constituent zones | Intensity Equation (13) |
| 0-1.2 | 6 | 0.3456a | 3 | 0.6912a |
| 0-2 | 10 | 1.6a | 5 | 3.2a |
| 0-2.4 | 12 | 2.7648a | 6 | 5.5296a |

Assuming that a certain region in an ophthalmic lens, for example a range of region of the diffraction structure, is given as radius=0-2 mm, the side-band peak intensity when the region is constituted by the equal-pitch structure of Δr=0.2 mm turns out to be 1.6a. Meanwhile, if Δr=0.4 mm, it turns out to be 3.2a and the peak intensity of the former is estimated to be about half the value of the latter.

However, since such comparison is limited to side-band peaks of equal orders as described above, when brightness is to be compared among similar expanses of halo, it is realistic to compare side-band peaks at positions as close to each other as possible. Since different values of Δr result in different positions of the side-band peak, peaks at almost the same position can be under different orders. For example, a peak of Δr=0.2 mm and order q=1 appears at the same position as a peak of Δr=0.4 mm and order q=2, and in such a case, a separate equation has to be introduced that can be used to compare intensity between different orders. In making such comparisons of intensity among different orders and phase constants, the following Equation 15 is to be used:

$$I_q \propto \text{Sinc}^2\{(q-h)\pi\} \quad \text{[Equation 15]}$$

$I_q$: Intensity of a side-band peak of a particular order q: Order number that determines the side band h: Phase constant Making a rough estimate of intensity at positions of Δr=0.2 mm and order q=1 and r=0.4 mm and order q=2, the values are obtained from the following Equations 16 and 17:

$$\Delta r=0.2 \text{ mm}: I_{q=1}=1.6a \times \text{Sinc}^2\{(1-0.5)\pi\}=1.6a \times 0.405=0.648a \quad \text{[Equation 16]}$$

$$\Delta r=0.4 \text{ mm}: I_{q=2}=3.2a \times \text{Sinc}^2\{(2-0.5)\pi\}=3.2a \times 0.045=0.144a \quad \text{[Equation 17]}$$

From the results of the above equations, the intensity at Δr=0.4 mm is about 20% of that at Δr=0.2 mm, which indicates that the intensity at the same position is rather lower in case of Δr=0.4 mm. Therefore, it can be foreseen that, if the pitch of the equal-pitch region is set at Δr=0.4 mm, a halo ring will be formed with high brightness equivalent to q=1 near the center of the light source, but the brightness of the ring around the halo will be smaller than when the region is composed of Δr=0.2 mm.

Since appearing positions of such side-band peaks and their halos are correlated, the appearing position $\rho_q$ of the side-band peak on the image plane at the focal point position of 0th order diffracted light is preferably restricted in the range of $\rho_q$ (mm)<|0.006×f (mm)×q| taking into account the expanse of halos. If the value of $\rho_q$ is larger than the upper limit, visibility can be lowered due to enlarged expanse of the halo even if the diffraction-type multifocal ophthalmic lens having an equal-pitch region produces an independent halo ring that are not planar. Therefore, it is desirable to set the pitch Δr of the diffraction zones in the equal-pitch region using Equation 3 not to have $\rho_q$ exceed the upper limit. For that reason, in the diffraction structure 20 according to the present invention, the pitch Δr of the diffraction zones is preferably 0.09 mm or more. Also, as exemplified above, the grating pitch (Δr) at equal widths is more preferably within the range of 0.2 mm to 0.4 mm.

Figure 11A:
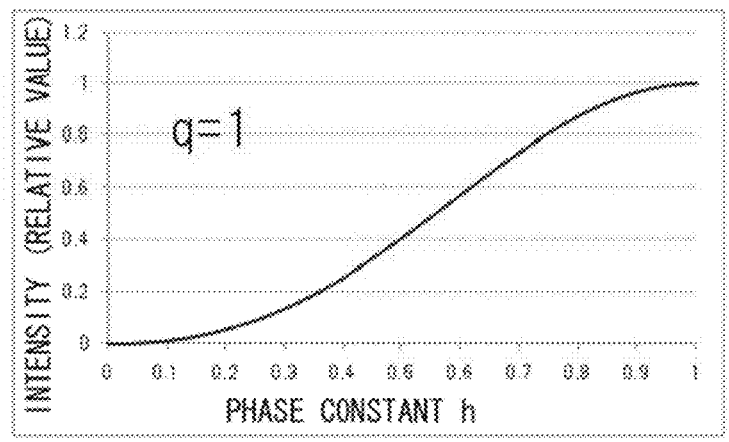
FIGS. 11A-11C are graphs showing the correlation between the intensity of side-band peaks at the order (q) of 1, 2 and 3 on the image plane at the focal point position of 0th order diffracted light and the phase constant h.
Figure 11B:
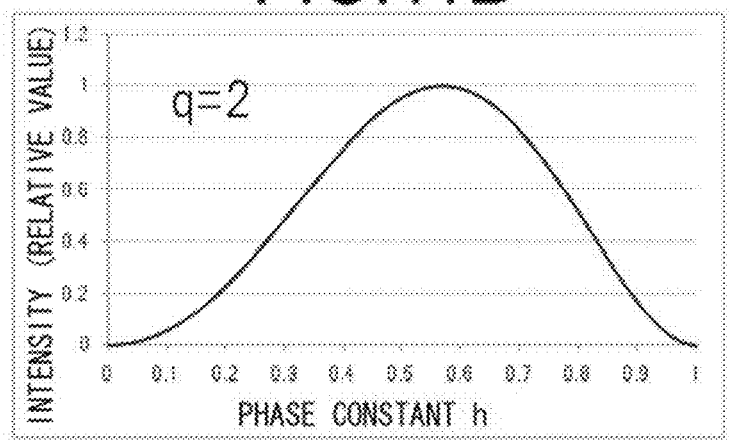
Figure 11C:
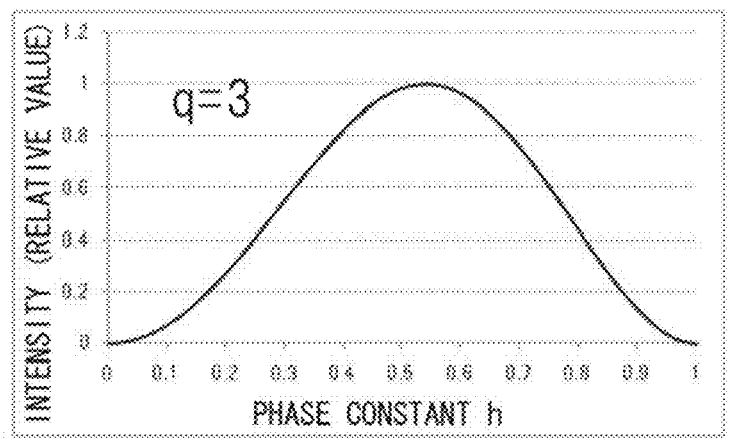

Also, in order to compare intensity between peaks with different phase constants h, an approximate comparison can be made using Equation 15. The way the intensity changes relative to the phase constant h differs depending on the order. Within the range of 0≤h≤1, the intensity of the side-band at order q=1 increases proportionately as the phase constant h increases as shown in FIG. 11A. Meanwhile, the intensity of side-bands other than those at q=1 is characterized by reaching the maximum when h is from 0.5 to 0.56 followed by falling down before and after that (FIGS. 11B, 11C). Therefore, key issues in designing the lens are addressed such that h should be set rather low when the side-band at q=1 is regarded as important and its intensity needs to be restricted, but setting the value of h around 0.5 should be avoided when side-bands other than those at q=1 are given more importance.

The diffraction-type lens containing an equal-pitch region is found to be useful as a diffraction-type lens potentially with reduced halos because it can restrict the generation of planar halos by localization of the peaks in the image plane intensity distribution resulting from equal pitches and the high degree of design freedom in controlling the position and brightness of the peaks.

The diffraction-type lens containing an equal-pitch region not only has the effect of reducing the expanse of halos by localizing the side-band peaks described above but also has specific imaging characteristics of forming intensity distribution where a focal point can be placed not only in the far or near distance but also somewhere in between. These characteristics allow the lens to form a focal point in each of the far, near and intermediate regions, which leads to a possibility of designing multifocal lenses such as a trifocal lens that is gaining more significance in recent years. The imaging characteristics on the optical axis of such diffraction-type lens containing equal pitches will be described below in comparison with the one with Fresnel pitches.

The pitch of the Fresnel pitch lens, which is one form of diffraction-type lens, can be defined as a prerequisite for forming a focal point by having the amplitudes of first-order diffracted light enhance each other at a particular position on the optical axis. Therefore, in case of a Fresnel-pitch lens, light from each zone travels to focus at a particular point on the optical axis (point O marked by an arrow) as shown in FIG. 12A, naturally resulting in generating a single peak of first-order diffracted light on the optical axis. Due to these characteristics of light traveling to focus at a particular point on the optical axis, the intensity distribution on the 0th order focal point image plane turns out to be random. This is the qualitative reason why the intensity distribution of the Fresnel pitch lens on the image plane exhibits random multi-peak side-bands.

Meanwhile, in case of a diffraction-type lens containing equal pitches, such diffracted light coming out of the equal-pitch region travels in such a way that the amplitudes enhance each other not on the optical axis but at a particular position on the 0th order focal point image plane (point $\rho_q$ shown by an arrow in FIG. 12B). More specifically, since diffracted light from each zone travels to have the amplitudes enhance each other at a particular position on the 0th order focal point image plane determined by Equation 3 above, it is quite understandable from FIG. 12B that the position where the light beam crosses the optical axis differs depending on the position of aperture where the light comes from. Light beams coming from small diameter apertures cross the optical axis at points closer to the lens and those from large diameter apertures cross at points farther therefrom. Thus, due to the overall mutual interference caused by light beams coming from different diameter apertures and crossing the optical axis at different positions, an extended intensity distribution is exhibited on the optical axis, resulting in the formation of focal points in the near to intermediate regions.

Such focusing on a point in the intermediate region between far and near distances is important in terms of ensuring the vision at certain distances necessary in everyday life such as watching the monitor display, looking for a book on the bookshelves, looking at self in the mirror, reading a transcript on the podium and so forth. Therefore, the present invention offers an ophthalmic lens suitable for a situation where such intermediate distance vision is necessary. In order to further understand the details of focusing characteristics on the optical axis of the diffraction-type lens containing equal-pitch zones as described above, the relation between the aperture diameter and $\Delta r$ will be described below.

Figure 13:
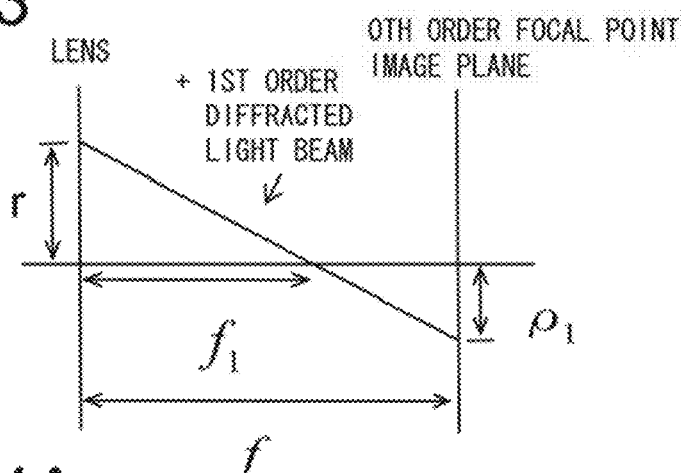
FIG. 13 is a diagram suitable for explaining the positional relation between the focal point position and the image plane of the first-order diffracted light.
Figure 14A:
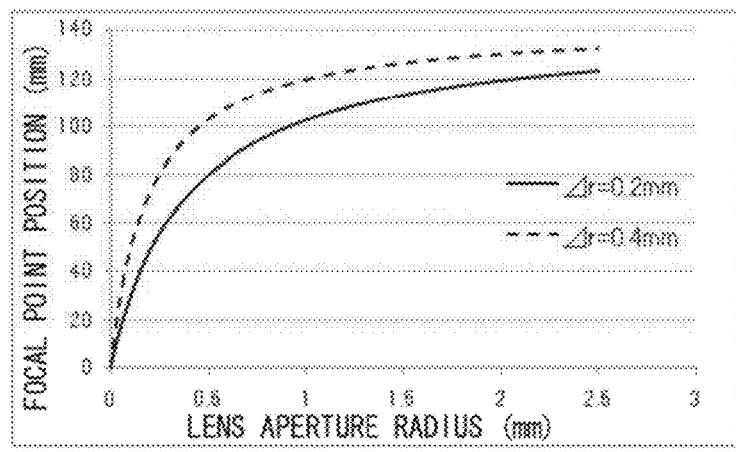
FIGS. 14A and 14B are graphs showing the correlation between the aperture position measured by radius of the lens with pitches Δr of diffraction zones varied among the equal-pitch regions and the focal point position as measured therefrom and the addition power of the first-order diffracted light.
Figure 14B:
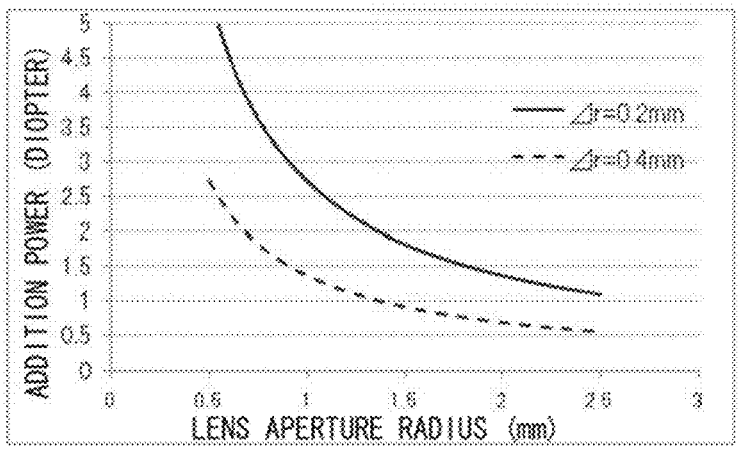

Assuming that a point where light emitted from a position of a lens containing equal-pitch zones at aperture radius r crosses the optical axis when reaching $\rho_1$ on the 0th order focal point image plane is the focal point position of the first-order diffracted light and its focal length is $f_1$. Then, assuming that the focal length of the 0th order diffracted light is f, the relation of Equation 18 is considered to hold geometrically between those variables (FIG. 13). Substituting Equation 3 using $\rho_1$ for Equation 18 below, Equation 19 is obtained. This is an equation representing how the first order focal length varies when the aperture radius varies relative to different values of $\Delta r$. Also, replacing the focal length of the first diffracted light with the addition power $P_{add}$ corresponding to the focal length, the relation between such addition power and $\Delta r$ is given by Equation 20. FIGS. 14A and 14B show how the focal length and addition power change based on these equations.

$$\frac{\rho_1}{f - f_1} = \frac{r}{f_1} \quad \text{[Equation 18]}$$

$$f_1 = \frac{r}{\frac{2f\pi}{k\Delta r} + r} \times f \quad \text{[Equation 19]}$$

$$P_{add} = \frac{2\pi}{rk\Delta r} \quad \text{[Equation 20]}$$

The following observations are made from FIGS. 14A and 14B: First of all, the larger the aperture diameter of the lens is (that is, if the number of constituent zones is increased), the first order diffracted light from the equal-pitch region moves toward the 0th order focal point regardless of the value of $\Delta r$. This allows the intensity distribution on the optical axis to spread out from the near-distance region to the intermediate-distance region. This is the end result of the fact that all the first-order diffracted light beams from each zone travel to enhance each other at $\rho_1$ on the image plane. These characteristics that allow the intensity distribution to spread out as the aperture diameter of the lens increases are ideal from the viewpoint of relation between the aperture diameter and depth of focus of the lens. In other words, under these conditions, there is no need to consider focusing in the intermediate region because the depth of focus is large enough in the small-diameter pupil of human eyes, and the intermediate region can be covered by the large depth of focus even in a lens with only two focal points set up for far and near visions. However, as the pupil enlarges in diameter, the depth of focus gets smaller to deteriorate the vision in the intermediate region, but the lens of the present invention starts to form a focal point in the intermediate region in a good timing in response to such conditions. Under these circumstances, the aperture diameter of the lens that determines the range of substantial incidence or emission of light when the focal point is starting to be generated in the intermediate region is preferably 1.5 mm or more in relation to the pupil diameter and depth of focus mentioned above.

Secondly, the smaller the value of $\Delta r$ is, the farther away is the focal point position of the first diffracted light from the equal-pitch region from the 0th order focal point. On the contrary, the larger the value of $\Delta r$ is, the closer the focal point position of the first-order diffracted light from the equal-pitch region to the 0th order focal point. In other words, the smaller the value of $\Delta r$ is, the larger the given addition power and vice versa. This is easily seen from the fact that the position $\rho_1$ of a side-band peak on the image plane at q=1 gets larger (smaller) as the value of $\Delta r$ gets smaller (larger) (from Equation 3), and the position where the light beam connecting the point of aperture and the position $\rho_1$ crosses the optical axis gets farther away from (closer to) the 0th order focal point position.

When the lens aperture gets large enough, the position where the first-order diffracted light crosses the optical axis, that is the focal length, gets infinitely closer to the 0th order focal point position as the aperture diameter of the lens is increased infinitely, but in case of lens aperture of finite diameter for practical use, the asymptotic value varies depending on the value of $\Delta r$. When $\Delta r$ is large enough, the focal position gets asymptotically closer to the 0th order focal point in an area closer to the 0th order focal point, whereas when $\Delta r$ is smaller, the focal position gets asymptotically closer to the same in an area farther away therefrom. Assuming that the pupil of human eye has a diameter of about 3.6 mm under the standard brightness in designing a diffraction-type lens containing an equal-pitch region at $\Delta r$=0.2 mm for example, the addition power $P_{add}$ varies within an approximate range from 1.5 to 3.5 Diopter so that it can be estimated that the intensity distribution in the near to intermediate regions is also formed in such a range. The diffraction-type multifocal lens with such intensity distribution in the near to intermediate regions is best fit for use by those with advanced presbyopia or patients who have their crystalline lens removed by cataract surgery. Also, the intensity distribution designed at $\Delta r$=0.4 mm accompanies the addition power $P_{add}$ varying in an approximate range from 0.7 to 1.5 Diopter so that the resulting intensity distribution can be estimated to be somewhere in that range. Therefore, the diffraction-type multifocal lens with such intensity distribution in the near to intermediate regions is best fit for patients with early-stage presbyopia.

It should be noted that the displacement of focal point positions and intensity distribution on the optical axis of the first-order diffracted light from these equal-pitch zones are not something that can be determined in a clear and uniform manner but are rather based on statistical distribution involving the effect of mutual interference between an infinite number of light waves coming from different apertures. Therefore, the displacement and distribution of focal point positions in the near to intermediate regions differ depending on the value of Δr that forms the diffraction structure and the combination of regions thereof, and the intensity distribution on the optical axis sometimes appears as a distribution formed with steep peaks such as those of Fresnel-pitch type, or a distribution with a single peak having wide skirts, or the one with multiple peaks or a range of peaks. In either form, since the extent of intensity distribution on the optical axis results in a large depth of focus, the focal points are formed not only at the far and near focal points but also all across the area called 'intermediate region.'

Thus, in case of the conventional Fresnel-pitch type, creating a focal point in a different position from others requires a new design due to the characteristics that allow the first-order diffracted light to form its peaks always at a certain position despite the varying aperture diameter, whereas the diffraction-type lens containing an equal-pitch region is capable of forming multiple focal points with a simple design of just setting an equal-pitch region in the diffraction structure.

Figure 15:
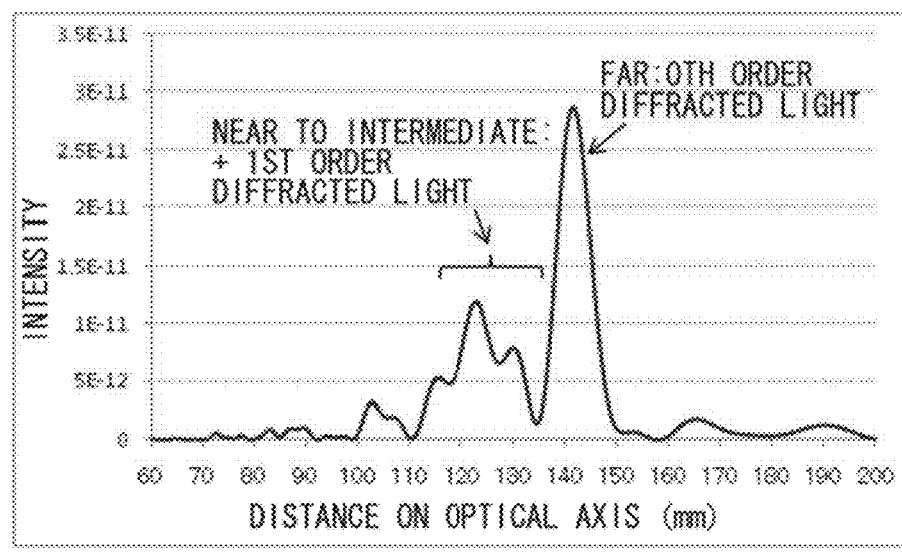
FIG. 15 is a graph showing results of simulation of intensity distribution on the optical axis in the phase profile of the first embodiment of the present invention.

The actual examples of these lenses will be described below in reference to FIGS. 15 and 16. FIG. 15 shows a result of computer simulation of intensity distribution on the optical axis obtained from the phase profile according to the present embodiment shown in FIG. 7. These results are derived from the calculation of the 1st to 4th zones of Table 1. The reason why not all the zones are used in the calculation is that a bright interior where the standard illumination is ensured is assumed in the calculation and further assumptions were made that the average pupil diameter of human eyes under such environment is 3.2 mm to 3.6 mm, and it is reasonable to consider in the calculation that the effective lens aperture of incidence of an ophthalmic lens such as a contact lens or an intraocular lens used near the pupil is equal to said pupil diameter. In other words, because it is important for a multifocal ophthalmic lens to realize the visual balance between near and far distances under the environment of the standard brightness, the intensity distribution on the optical axis is examined for diffraction zones within the range of such lens aperture sizes. In other embodiments described below, the diffraction zones used in the calculation of intensity distribution on the optical axis are considered to be within the same range of aperture sizes. As evident from FIG. 15, the distribution is composed of the far vision focal point by the 0th order diffracted light at the optical part front surface 14 and the optical part back surface 16 as refraction interfaces and the multi-peak portion formed by the first-order diffracted light extending from the near to intermediate regions of the phase profile 26 (diffraction structure 20), and therefore, it is understood that the distribution gives a certain vision in the intermediate region, not to mention the near region.

Figure 16:
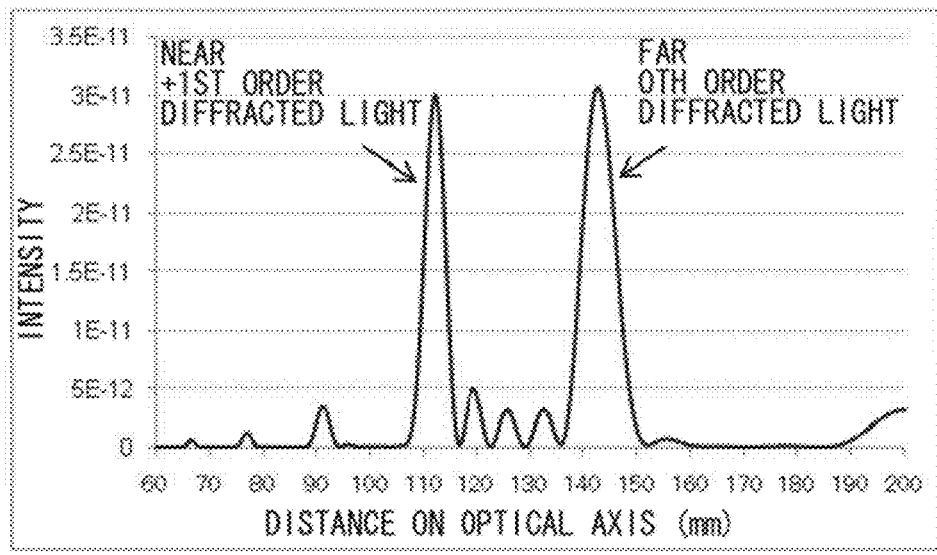
FIG. 16 is a graph showing results of simulation of intensity distribution on the optical axis in the phase profile of Comparative Example 1.

FIG. 16 shows results of computer simulation of intensity distribution on the optical axis obtained from the phase profile shown in FIG. 8 as Comparative Example 1. These results are derived from the calculation of the 1st to 5th zones of Table 2. As evident from the figure, the far and near vision focal points are clearly discernible but no peak was identified that can be an intermediate vision focal point, unlike the present embodiment described in reference to FIG. 15. The intensity distribution on the optical axis of the Fresnel pitch type, which is Comparative Example 1, is found to have deteriorated visibility in the intermediate region for a certain period of time in case of a Fresnel-pitch type bifocal lens, which indicates the actual optical behavior described above.

Considering the relation between said Δr and the focal length (Equations 19, 20) and the like, if Δr is less than 0.1 mm, the pitch Δr in the diffractive zones forming the equal-pitch region suitable for generating such intermediate region causes the first-order diffracted light to focus at a position substantially far from the 0th order focal point position, too far from the practically required focal point position to make it unsuitable as a multifocal lens. Meanwhile, if Δr is larger than 0.5 mm, the diffracted light gets substantially close to the 0th order focal point position, and the addition power for forming the practically required focal point position is insufficient, which is not suitable as a multifocal lens, either. Therefore, in the diffraction structure 20 according to the present invention, it is desirable to let the pitch Δr of the diffraction zones in the equal-pitch region meet the following formula:

$$0.1 \text{ mm} \leq \Delta r \leq 0.5 \text{ mm}$$

The example here is given under a condition that the grating pitch (Δr) of equal widths is 0.4 mm as shown in Table 1. The pitch is not limited to this value as a matter of course, but the grating pitch (Δr) of equal widths is preferably within a range of 0.1 mm to 0.5 mm as mentioned above. More preferably, the grating pitch (Δr) of equal widths is within a range of 0.2 mm to 0.4 mm.

The impact of the phase constant h on the formation of a focal point in the near to intermediate regions of the first-order diffracted light in the diffraction-type multifocal ophthalmic lens containing an equal-pitch region described above is given primarily by determining the allocation of energy of light between the 0th order and first-order diffracted light. For example, in designing a lens that prioritizes visions in the near to intermediate regions, the share of energy of the first-order diffracted light for forming a focal point in the near to intermediate regions needs to be increased, which can be achieved by increasing the phase constant h. On the contrary, if visibility in the far region is given priority, the phase constant h should be decreased. The phase constant h can be changed arbitrarily to meet the requirement for visibility of the near, intermediate and far regions, and there is no restriction for the phase constant h. However, if the value of h exceeds 1.5 (although it does not hold true for some phase profiles), there is a risk of getting too many multiple-order light beams, and therefore, it is desirable to keep the constant in the range of 0≤h≤1.5. Since the phase constant gives an impact on the formation behavior of side-band peaks in the image plane intensity distribution as described above, it is desirable to set the constant by taking such behavior into account.

An embodiment of the present invention has been described in detail above, but it is just an example and the present invention should not be interpreted in a way limited by such specific description. Other aspects that can favorably be used in the present invention are described below, but it should be noted that the present invention is not limited to those aspects. In the following paragraphs, detailed descriptions of substantially the same members and parts as those of the above-described embodiment are omitted by assigning the same numerals to the equivalent components.

Figure 17:
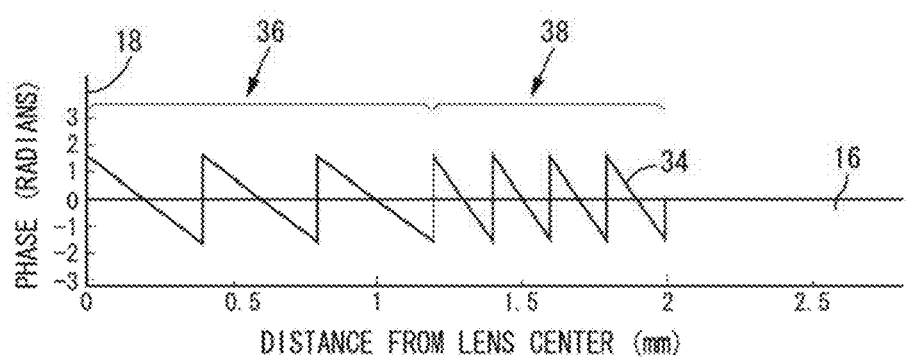
FIG. 17 is a phase profile as a second embodiment of the present invention.

FIG. 17 shows a magnified cross section of a phase profile 34 as a second embodiment of the present invention. In the present embodiment, unlike the previous one, the 1st to 3rd zones are assumed to be a first equal-pitch region 36 composed of a periodic structure with equal pitches of grating pitch Δr=0.4 mm, and the 4th to 7th zones are assumed to be a second equal-pitch region 38 composed of a periodic structure with equal pitches of grating pitch Δr=0.2 mm as shown in Table 5. The phase constant h is set at 0.5 in all zones.

TABLE 5

| Zone No. | Zone radius | | Phase | | Phase constant h | Pitch |
|---|---|---|---|---|---|---|
| | $r_n$ (mm) | $r_{n-1}$ (mm) | $\phi_n$ (radian) | $\phi_{n-1}$ (radian) | | |
| 1st zone | 0.4 | 0 | −1.5708 | 1.5708 | 0.5 | Δr = 0.4 mm |
| 2nd zone | 0.8 | 0.4 | −1.5708 | 1.5708 | 0.5 | |
| 3rd zone | 1.2 | 0.8 | −1.5708 | 1.5708 | 0.5 | |
| 4th zone | 1.4 | 1.2 | −1.5708 | 1.5708 | 0.5 | Δr = 0.2 mm |
| 5th zone | 1.6 | 1.4 | −1.5708 | 1.5708 | 0.5 | |
| 6th zone | 1.8 | 1.6 | −1.5708 | 1.5708 | 0.5 | |
| 7th zone | 2 | 1.8 | −1.5708 | 1.5708 | 0.5 | |

Figure 18:
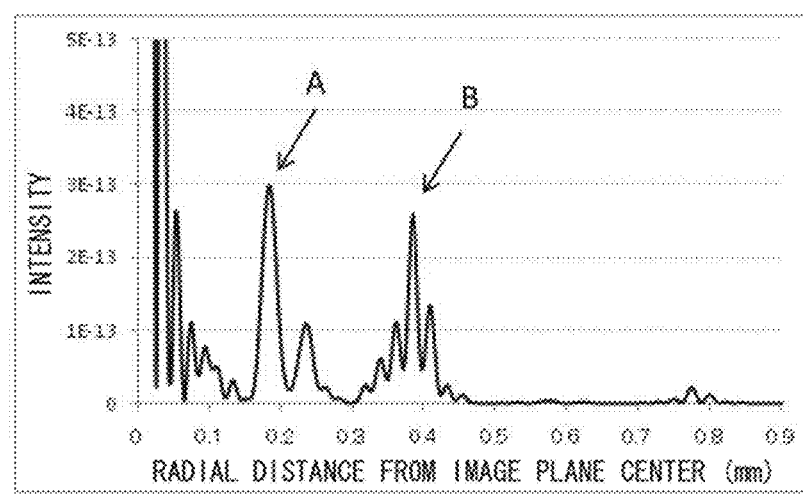
FIG. 18 is a graph showing results of simulation of the image plane intensity distribution at the focal point position of 0th order diffracted light in the phase profile of FIG. 17.

FIG. 18 shows results of computer simulation of the image plane intensity distribution at the focal point position of 0th order diffracted light of the present embodiment. These results correspond to the calculated results of the 1st to 7th zones of Table 5 above. In the present embodiment, like in the previous one, steep peaks exist near the center of the image plane and the intensity drops down rapidly in the periphery to eventually display almost no noise. Therefore, it is found that the diffraction-type lens of the present embodiment has the halos reduced at night. Since the lens of the present embodiment is composed of two equal-pitch regions with different grating pitches Δr, contribution of such different pitches are reflected in the intensity distribution. For example, the peak at ρ=0.195 mm near the center of the image plane (arrow A in FIG. 18) is identified as the one at q=1 from the region of grating pitch Δr=0.4 mm and the adjacent peak at ρ=0.38 mm (arrow B in FIG. 18) is identified as the one at q=1 from the region of grating pitch Δr=0.2 mm. Also, as to the peak of Δr=0.4 mm, the number of constituent zones is less than that of the first embodiment so that such peak intensity is smaller than that of the first embodiment at q=1. Meanwhile, according to Equation 14, the intensity of the peak of Δr=0.2 mm should be about 60% of the intensity of the peak of Δr=0.4 mm but it turns out to be about the same. This is because of the synergistic effect of superposed regions resulted in such intensity since the appearance position of the peak of grating pitch Δr=0.2 mm at q=1 coincides with the appearance position of the peak at q=2 from the region of grating pitch Δr=0.4 mm.

Figure 19:
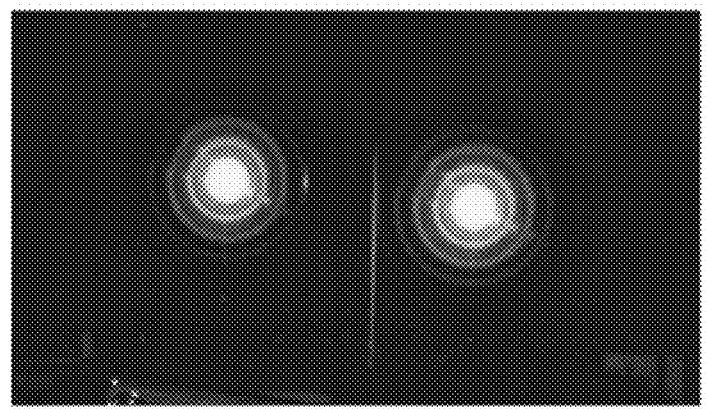
FIG. 19 is an actual photo of halos in the phase profile of FIG. 17.

Next, FIG. 19 shows an actual photo of light sources at far distance. Judging from the measurement results, it was confirmed, as was the case in the previous embodiment, that the halos had been clearly reduced in the present embodiment shown in FIG. 19 as compared to the comparative example shown in FIG. 10B. Like the previous embodiment, the halos are not extensively planar like those of the Fresnel pitch lens of the comparative example but are showing more excellent characteristics of fine halo rings.

Figure 20:
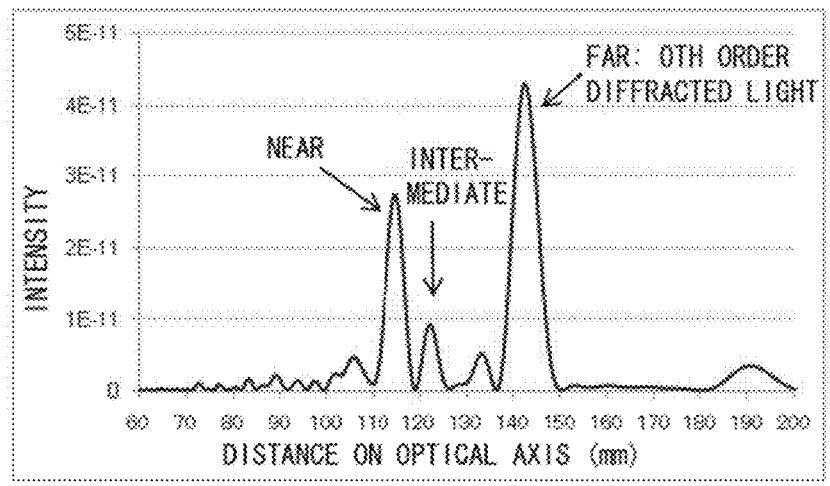
FIG. 20 is a graph showing results of simulation of intensity distribution on the optical axis in the phase profile of FIG. 17.

Furthermore, FIG. 20 shows results of computer simulation and confirmation of intensity distribution on the optical axis obtained in the present embodiment. These results are derived from the calculation of the 1st to 6th zones of Table 5. As evident from FIG. 20, it was confirmed that, in addition to the far vision focal point of the 0th order diffracted light through the optical part 12 of the ophthalmic lens 10, the near vision focal point of the first-order diffracted light of the phase profile 34 as well as a peak of the intermediate vision focal point had been formed.

As described above, it was found that a multifocal ophthalmic lens can be offered with reduced halos at night even in case of having multiple equal-pitch regions with different grating pitches Δr providing a good balance among far, intermediate and near visions. In the present embodiment, an example was shown of the phase profile composed of two kinds of equal-pitch regions, but it can be composed of three or more equal-pitch regions as described later.

Figure 21:
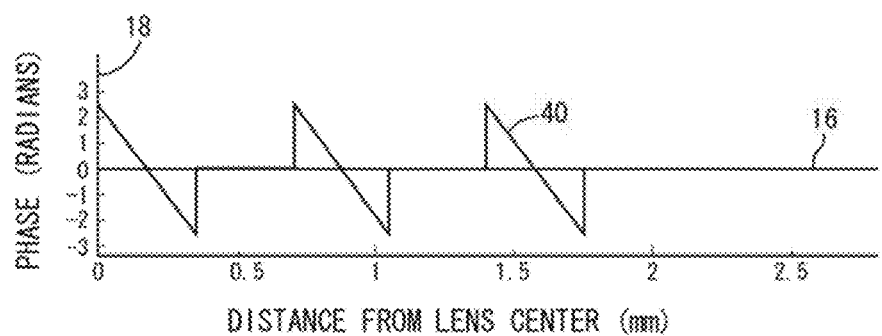
FIG. 21 is a phase profile as a third embodiment of the present invention.

FIG. 21 shows a magnified cross section of a phase profile 40 as a third embodiment of the present invention. In the present embodiment, the regions with and without a blaze form alternately appear three times each at grating pitch Δr=0.35 mm in both cases as shown in Table 6 below. Here, the phase constant h is fixed at 0.8 for the zone with the blaze form and 0 for the zone without it.

TABLE 6

| Zone No. | Zone radius | | Phase | | Phase constant h | Pitch |
|---|---|---|---|---|---|---|
| | $r_n$ (mm) | $r_{n-1}$ (mm) | $\phi_n$ (radian) | $\phi_{n-1}$ (radian) | | |
| 1st zone | 0.35 | 0 | −2.5133 | 2.5133 | 0.8 | Blaze portion Δr = 0.35 mm |
| 2nd zone | 0.7 | 0.35 | 0 | 0 | 0 | |
| 3rd zone | 1.05 | 0.7 | −2.5133 | 2.5133 | 0.8 | |
| 4th zone | 1.4 | 1.05 | 0 | 0 | 0 | Non-blaze portion Δr = 0.35 mm |
| 5th zone | 1.75 | 1.4 | −2.5133 | 2.5133 | 0.8 | |
| 6th zone | 2.1 | 1.75 | 0 | 0 | 0 | |

Figure 22:
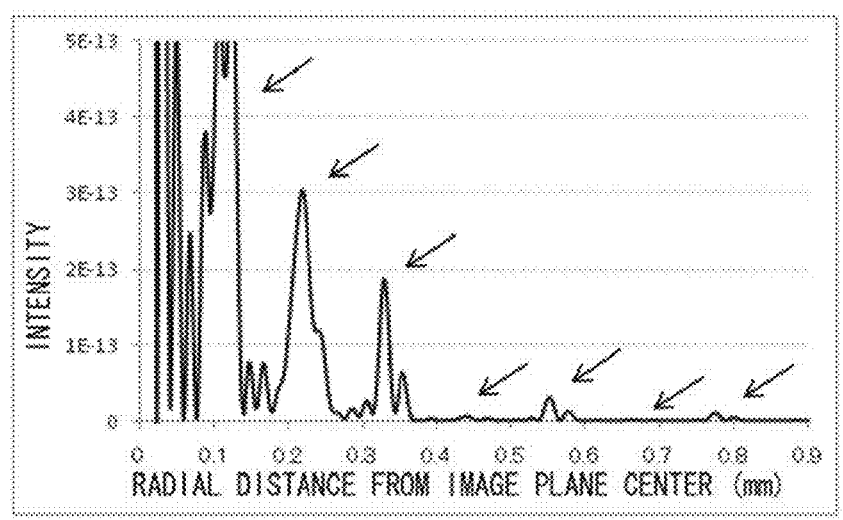
FIG. 22 is a graph showing results of simulation of the image plane intensity distribution at the focal point position of 0th order diffracted light in the phase profile of FIG. 21.

FIG. 22 shows results of computer simulation of the image plane intensity distribution at the focal point position of the 0th order diffracted light of the present embodiment. These results are derived from the calculation of the 1st to 6th zones of Table 6. Peaks appear at constant intervals even in the present embodiment, but the behavior of appearance is observed that their intensity rapidly drops down toward the periphery of the image plane reflecting the equal-pitch characteristics, making almost no noise in other regions. Therefore, it is found that the lens of the present embodiment can be a diffraction-type lens with reduced halos at night. The appearance positions of the peaks also include those different from the positions calculated by Equation 12 in the present embodiment. This is because the diffraction zones are not continuous, and the peaks appear not only at the positions determined by Equation 3 (ρ=0.222, 0.444, 0.668 mm . . . ) but also at the multiples of half the intervals (ρ=0.111, 0.334, 0.557 . . . , except duplicates). Since the intensity is displayed for the blaze portion and non-blaze portion adjacent to each other, the intensity of the peaks on the image plane corresponding to such positional relation gets lower, whereas the peaks at the multiples of half the intervals are combined together to get larger.

Figure 23:
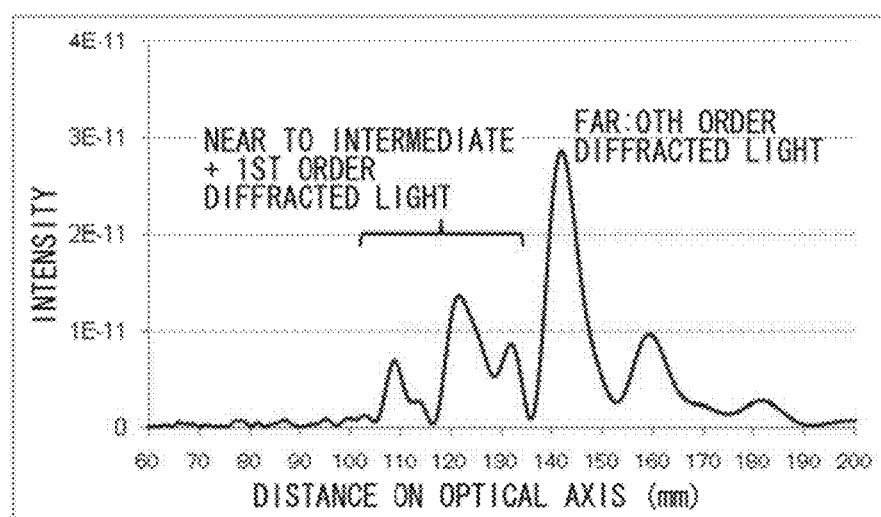
FIG. 23 is a graph showing results of simulation of intensity distribution on the optical axis in the phase profile of FIG. 21.

Next, FIG. 23 shows results of computer simulation of the image plane intensity distribution obtained in the present invention. These results are derived from the calculation of the 1st to 5th zones of Table 6. Since distinct peaks are formed in the near and intermediate regions even in the present embodiment as evident from FIG. 23, it is found that the lens of such example can be a multifocal ophthalmic lens that provides a well-balanced vision in each of far, intermediate and near regions.

Figure 24:
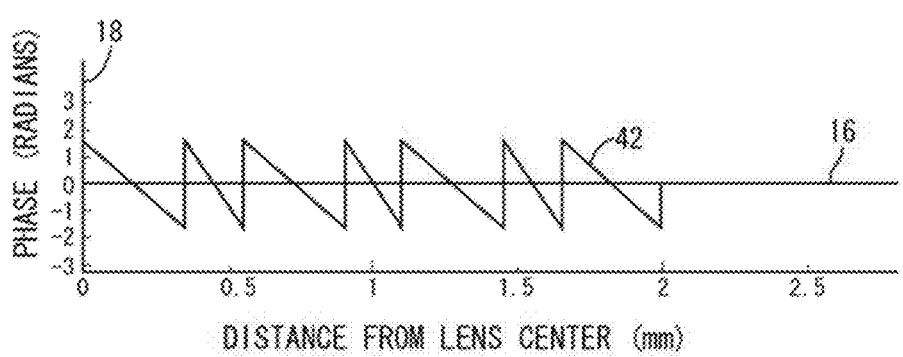
FIG. 24 is a phase profile as a fourth embodiment of the present invention.

FIG. 24 shows a magnified cross section of a phase profile 42 as a fourth embodiment of the present invention. In the present embodiment, the regions composed of a periodic structure are displayed where zones with the grating pitch Δr=0.35 mm and Δr=0.2 mm are alternately arranged as shown in Table 7. Here, the phase constant h is set at 0.5.

TABLE 7

| Zone No. | Zone radius | | Phase | | | |
|---|---|---|---|---|---|---|
| | $r_n$ (mm) | $r_{n-1}$ (mm) | $\phi_n$ (radian) | $\phi_{n-1}$ (radian) | Phase constant h | Pitch |
| $1^{st}$ zone | 0.35 | 0 | −1.5708 | 1.5708 | 0.5 | Δr = 0.35 mm |
| $2^{nd}$ zone | 0.55 | 0.35 | −1.5708 | 1.5708 | 0.5 | Δr = 0.2 mm |
| $3^{rd}$ zone | 0.9 | 0.55 | −1.5708 | 1.5708 | 0.5 | Δr = 0.35 mm |
| $4^{th}$ zone | 1.1 | 0.9 | −1.5708 | 1.5708 | 0.5 | Δr = 0.2 mm |
| $5^{th}$ zone | 1.45 | 1.1 | −1.5708 | 1.5708 | 0.5 | Δr = 0.35 mm |
| $6^{th}$ zone | 1.65 | 1.45 | −1.5708 | 1.5708 | 0.5 | Δr = 0.2 mm |
| $7^{th}$ zone | 2 | 1.65 | −1.5708 | 1.5708 | 0.5 | Δr = 0.35 mm |

Figure 25:
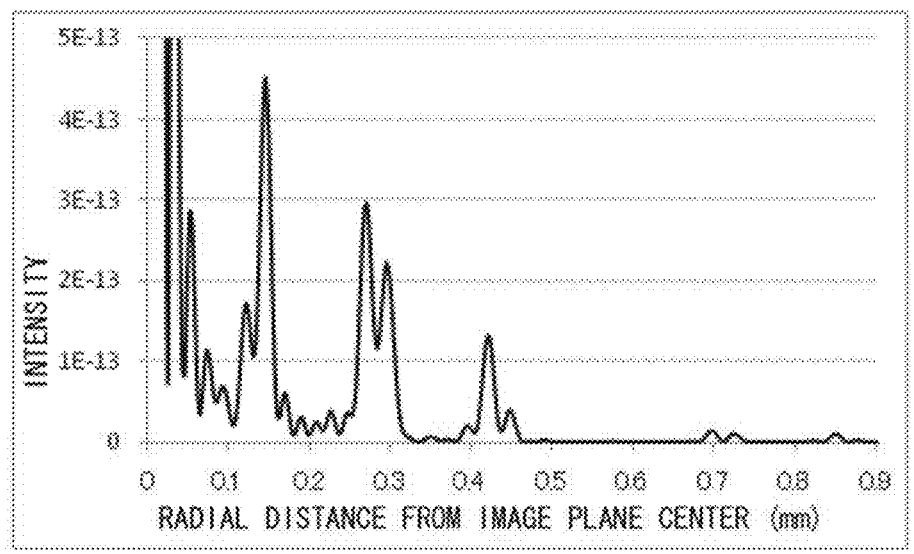
FIG. 25 is a graph showing results of simulation of the image plane intensity distribution at the focal point position of 0th order diffracted light in the phase profile of FIG. 24.

FIG. 25 shows results of computer simulation of the image plane intensity distribution at the focal point position of the 0th order diffracted light of the present embodiment. These results are derived from the calculation of the 1st to 7th zones of Table 7. Peaks appear at constant intervals even in the present embodiment, but the behavior of appearance is observed that their intensity rapidly drops down in the periphery of the image plane reflecting the equal-pitch characteristics, making almost no noise in other regions. Therefore, it is found that the halos are reduced at night in the present embodiment, too.

Figure 26:
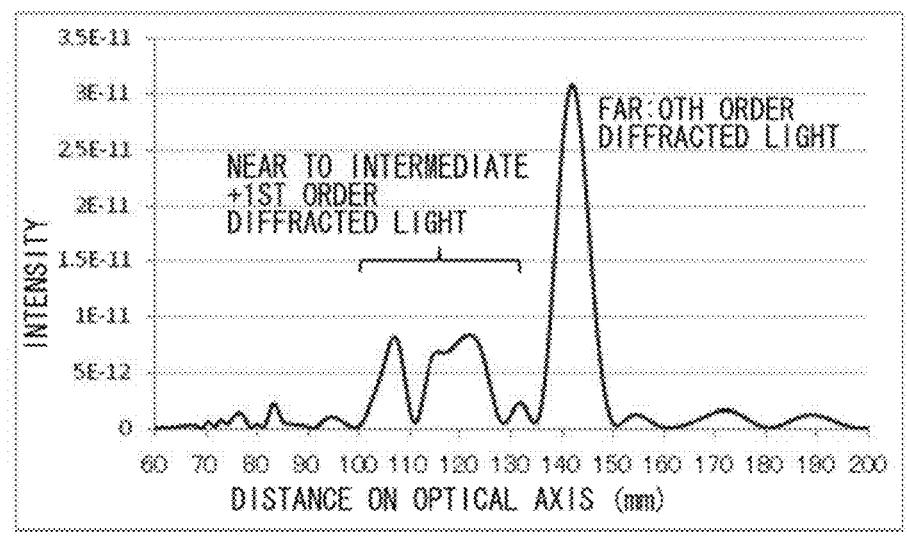
FIG. 26 is a graph showing results of simulation of intensity distribution on the optical axis in the phase profile of FIG. 24.

Next, FIG. 26 shows results of computer simulation of intensity distribution on the optical axis obtained in the present embodiment. These results are derived from the calculation of the 1st to 6th zones of Table 7. Since distinct peaks are formed in the near and intermediate regions even in the present embodiment as evident from FIG. 26, it is found that the lens of such example can be a multifocal ophthalmic lens that provides a well-balanced vision in each of far, intermediate and near regions.

Figure 27:
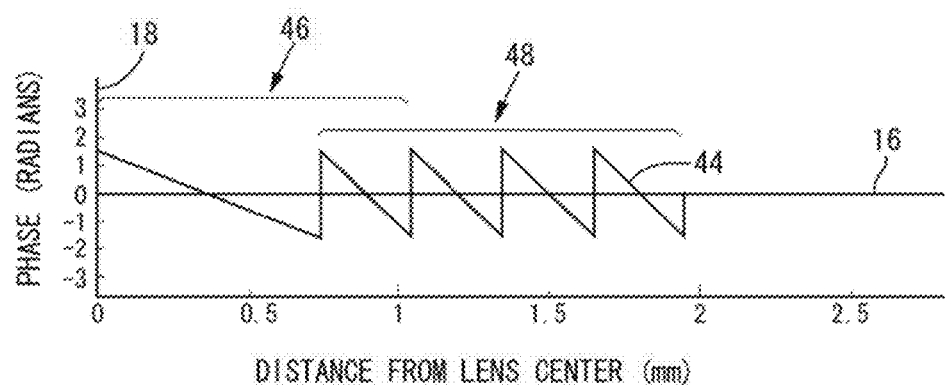
FIG. 27 is a phase profile as a fifth embodiment of the present invention.

FIG. 27 shows a magnified cross section of a phase profile 44 as a fifth embodiment of the present invention. In the present embodiment, the 1st and 2nd zones are made to be a Fresnel region 46 designed to make the addition power $P_{add}$ equal to 2 Diopter as shown in Table 8. Also the 3rd to 5th zones are made to be an equal-pitch region 48 composed of a periodic structure with the same pitch as the 2nd zone at the grating pitch Δr=0.306. The phase constant h is set at 0.5 in all zones.

TABLE 8

| Zone No. | Zone radius | | Phase | | | |
|---|---|---|---|---|---|---|
| | $r_n$ (mm) | $r_{n-1}$ (mm) | $\phi_n$ (radian) | $\phi_{n-1}$ (radian) | Phase constant h | Pitch |
| $1^{st}$ zone | 0.738918 | 0 | −1.5708 | 1.5708 | 0.5 | Fresnel pitch |
| $2^{nd}$ zone | 1.044988 | 0.738918 | −1.5708 | 1.5708 | 0.5 | |
| $3^{rd}$ zone | 1.351057 | 1.044988 | −1.5708 | 1.5708 | 0.5 | Equal pitch |
| $4^{th}$ zone | 1.657127 | 1.351057 | −1.5708 | 1.5708 | 0.5 | |
| $5^{th}$ zone | 1.963197 | 1.657127 | −1.5708 | 1.5708 | 0.5 | Δr = 0.306 mm |

Figure 28:
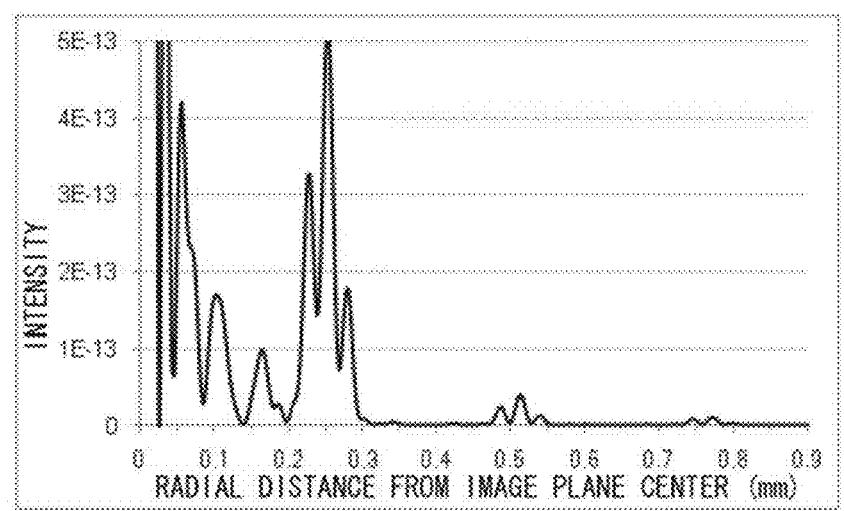
FIG. 28 is a graph showing results of simulation of the image plane intensity distribution at the focal point position of 0th order diffracted light in the phase profile of FIG. 27.

FIG. 28 shows results of computer simulation of the image plane intensity distribution at the focal point position of the 0th order diffracted light of the present embodiment. These results are derived from the calculation of the 1st to 5th zones of Table 8. It is found that this distribution mainly reflects the characteristics of the equal-pitch region although it partially includes the Fresnel pitch region, wherein a comparatively high intensity peak appears around ρ=0.25 mm but the intensity rapidly drops down in the periphery to eventually display almost no noise in other regions.

Figure 29:
FIG. 29 is an actual photo of halos in the phase profile of FIG. 27.

Next, FIG. 29 shows an actual photo of light sources of the present embodiment at far distance. That is, judging from the measurement results, the lens is found to be useful enough at night since the halos do not have planar expanse as shown in the comparative example (FIG. 10B), although the brightness of the ring corresponding to the peak at ρ=0.25 mm described above is on the high side.

Figure 30:
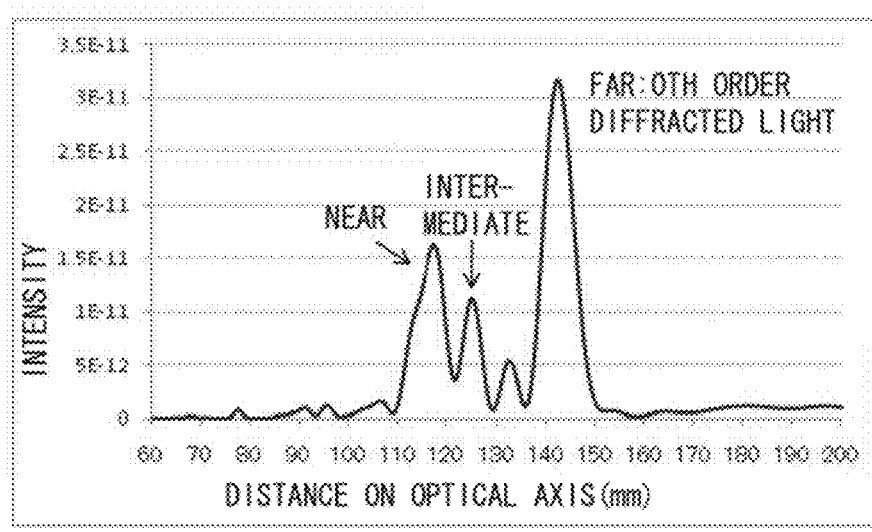
FIG. 30 is a graph showing results of simulation of intensity distribution on the optical axis in the phase profile of FIG. 27.

Furthermore, FIG. 30 shows results of computer simulation of intensity distribution on the optical axis obtained in the present embodiment. These results are derived from the calculation of the 1st to 4th zones of Table 8. As clearly observed in FIG. 30, a distinctively intensive peak is formed in the near region while a little smaller peak is formed in the intermediate region around the skirts on the far region side. It is seen that a well-balanced vision is provided in the near to intermediate regions due to the formation of such peaks. Since the Fresnel pitch of the present embodiment is designed to make the addition power equal to 2 Diopter, the peak formed in the near region at around 110-120 mm on the optical axis is mainly determined by the contribution of the first-order diffracted light in such Fresnel region. Meanwhile, the peak formed in the intermediate region at around 123 mm on the optical axis is mainly determined by the contribution of the first-order diffracted light in the equal-pitch region. Also the peak intensity in the near region is higher than when the diffraction structure is composed solely of equal-pitch regions, which is caused by the synergy with the contribution of Fresnel pitches. In such an intensity distribution, the embodiment is made to ensure the intermediate and far visions without lowering the quality of the near vision. In other words, the present embodiment indicates that the balance among the near, intermediate and far visions can be controlled freely by having at least one of the multiple focal lengths of the first-order diffracted light in the equal-pitch region made larger than the focal length of the first-order diffracted light in the Fresnel region.

Figure 31:
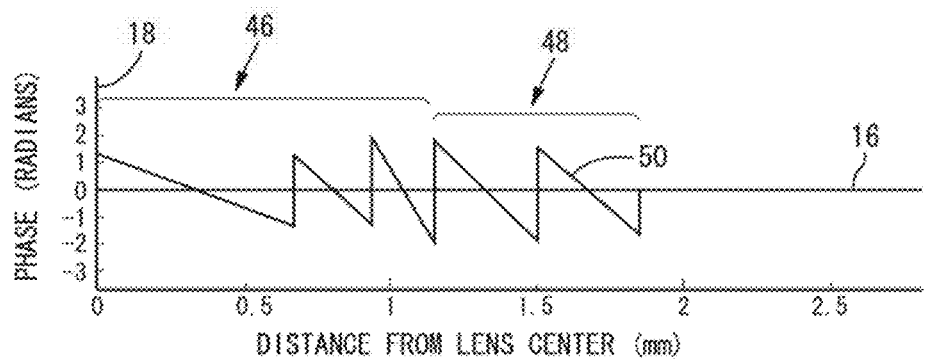
FIG. 31 is a phase profile as a sixth embodiment of the present invention.

FIG. 31 shows a magnified cross section of a phase profile 50 as a sixth embodiment of the present invention. In the present embodiment, the 1st to 3rd zones are made to be the Fresnel region 46 designed to make the addition power $P_{add}$ equal to 2.5 Diopter as shown in Table 9. Also the 4th and 5th zones are made to be an equal-pitch region 48 composed of a periodic structure with equal pitches at the grating pitch Δr=0.35 mm. The phase constant is set as shown in Table 9.

TABLE 9

| Zone No. | Zone radius | | Phase | | | |
|---|---|---|---|---|---|---|
| | $r_n$ (mm) | $r_{n-1}$ (mm) | $\phi_n$ (radian) | $\phi_{n-1}$ (radian) | Phase constant h | Pitch |
| $1^{st}$ zone | 0.660908 | 0 | −1.2566 | 1.2566 | 0.4 | Fresnel pitch |
| $2^{nd}$ zone | 0.934665 | 0.660908 | −1.2566 | 1.2566 | 0.4 | |
| $3^{rd}$ zone | 1.144727 | 0.934665 | −1.8849 | 1.8849 | 0.6 | |
| $4^{th}$ zone | 1.494727 | 1.144727 | −1.8849 | 1.8849 | 0.6 | Δr = 0.35 mm |
| $5^{th}$ zone | 1.844727 | 1.494727 | −1.5708 | 1.5708 | 0.5 | |

Figure 32:
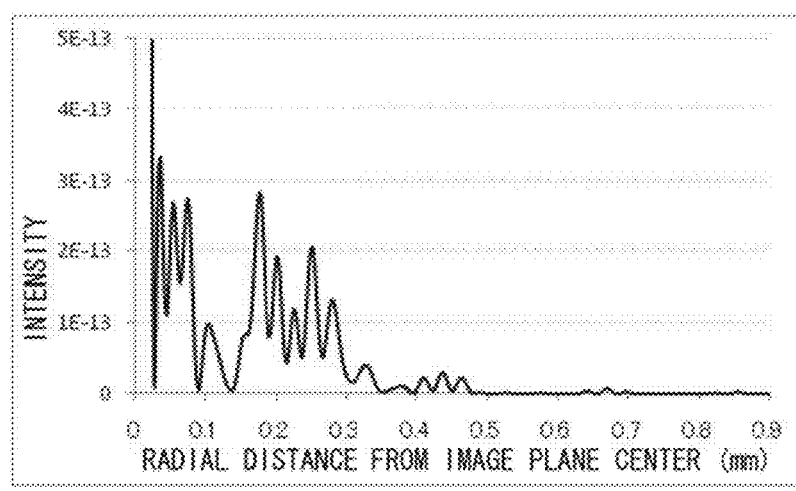
FIG. 32 is a graph showing results of simulation of the image plane intensity distribution at the focal point position of 0th order diffracted light in the phase profile of FIG. 31.

FIG. 32 shows results of computer simulation of the image plane intensity distribution at the focal point position of 0th order diffracted light of the present embodiment. These results are derived from the calculation of the 1st to 5th zones of Table 9. The graph reflects characteristics of both the Fresnel pitch and the equal pitch showing peaks with equal intervals as if they were split from an peak in the range of ρ=0.15 to 0.28 mm, but it is inferred that they don't have much impact on the halo because of their concentration toward the center of the image plane.

Figure 33:
FIG. 33 is an actual photo of halos in the phase profile of FIG. 31.

Next, FIG. 33 shows an actual photo of light sources of the present embodiment at far distance. That is, it was confirmed from the measurement results that the halos had been reduced to an almost unnoticeable level.

Figure 34:
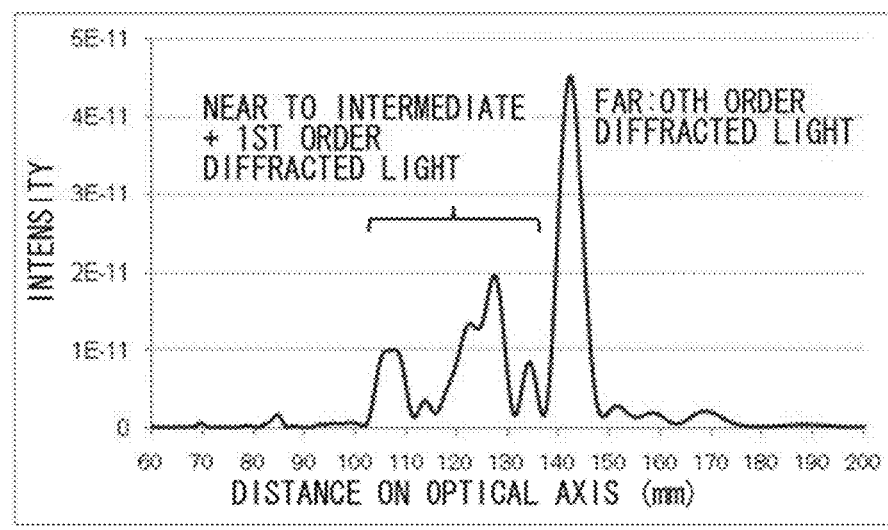
FIG. 34 is a graph showing results of simulation of intensity distribution on the optical axis in the phase profile of FIG. 31.

This working example represents a lens wherein Fresnel pitches are set to make the addition power $P_{add}$ equal to 2.5 Diopter and the near focal point position is moved closer to the lens, which was designed with patients of further advanced presbyopia. In addition, it is designed such that the non-focal-point region generated between the near and far focal points due to the near focal point position moved closer to the lens is compensated by supplementing a focal point in the intermediate region by means of adding the equal-pitch region. FIG. 34 shows results of computer simulation and confirmation of the image plane intensity distribution obtained in the present embodiment. These results are derived from the calculation of the 1st to 5th zones of Table 9. As evident from FIG. 34, according to the present embodiment, it was confirmed that a peak had been formed around the near focal point based on Fresnel pitches and equal pitches, and at the same time, the intermediate region had been formed with equal pitches.

Figure 35:
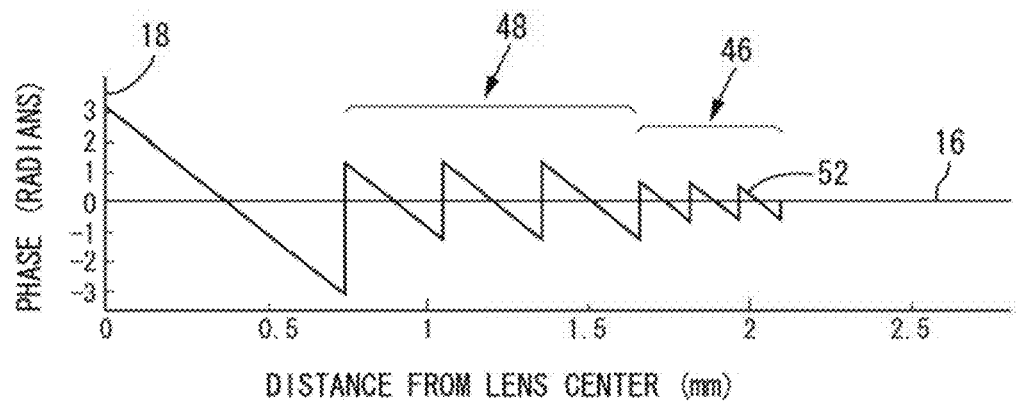
FIG. 35 is a phase profile as a seventh embodiment of the present invention.

FIG. 35 shows a magnified cross section of a phase profile 52 as a seventh embodiment of the present invention. In the present embodiment, as shown in Table 10, the central 1st zone radius is made of Fresnel pitches to make the addition power $P_{add}$ equal to 2 Diopter, while the adjacent 2nd to 4th zones are made to be the equal-pitch region 48 composed of a periodic structure with equal pitches of grating pitch Δr=0.306 mm and the further outer 5th to 7th zones are composed of the Fresnel region 46 that makes the addition power $P_{add}$ equal to 2 Diopter. In other words, the inner side of the lens is the equal-pitch region 48, and the Fresnel region 46 is configured further outside, which is one of the aspects of the fifth and sixth embodiments with the order of the Fresnel region and equal-pitch region reversed. The phase constant h is set as shown in Table 10.

TABLE 10

| Zone No. | Zone radius | | Phase | | | |
| | $r_n$ (mm) | $r_{n-1}$ (mm) | $\phi_n$ (radian) | $\phi_{n-1}$ (radian) | constant h | Pitch |
|---|---|---|---|---|---|---|
| $1^{st}$ zone | 0.738918 | 0 | −3.1416 | 3.1416 | 1 | |
| $2^{nd}$ zone | 1.044988 | 0.738918 | −1.3013 | 1.3013 | 0.4142 | Δr = 0.306 mm |
| $3^{rd}$ zone | 1.351057 | 1.044988 | −1.3013 | 1.3013 | 0.4142 | |
| $4^{th}$ zone | 1.657127 | 1.351057 | −1.3013 | 1.3013 | 0.4142 | |
| $5^{th}$ zone | 1.814406 | 1.657127 | −0.6687 | 0.6687 | 0.2128 | Fresnel pitch |
| $6^{th}$ zone | 1.959099 | 1.814406 | −0.6152 | 0.6152 | 0.1958 | |
| $7^{th}$ zone | 2.093817 | 1.959099 | −0.5728 | 0.5728 | 0.1823 | |

Figure 36:
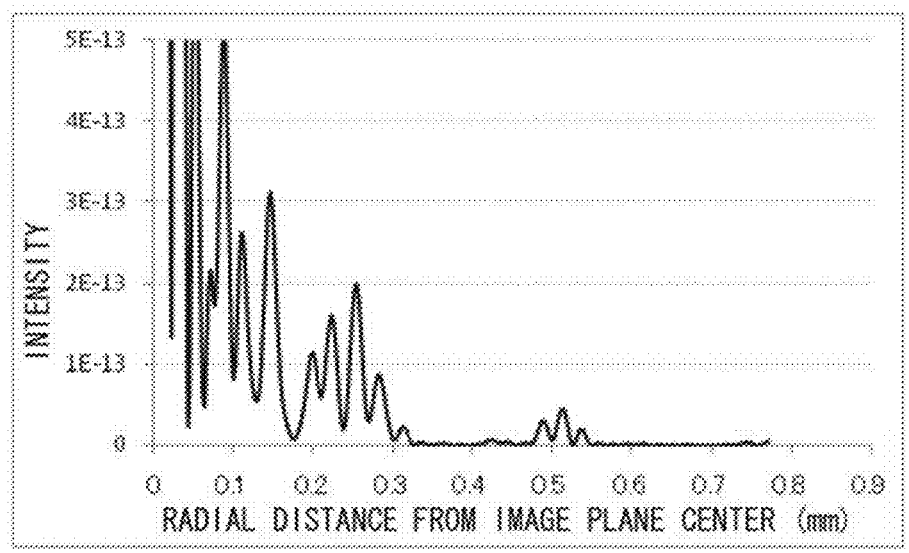
FIG. 36 is a graph showing results of simulation of the image plane intensity distribution at the focal point position of 0th order diffracted light in the phase profile of FIG. 35.

FIG. 36 shows results of computer simulation of the image plane intensity distribution at the focal point position of the 0th order diffracted light of the present embodiment. These results are derived from the calculation of the 1st to 7th zones. Although the Fresnel region 46 is arranged in the periphery of the lens, the image plane intensity distribution is mainly reflecting the characteristics of the equal-pitch region 48 with a group of split peaks appearing at around ρ=0.2 to 0.3 mm, but it is inferred that they don't have much impact on the halo because of their formation around the center of the image plane. Besides, in the periphery of the image plane, the intensity of the peaks rapidly drops down to eventually display almost no noise in other regions.

Figure 37:
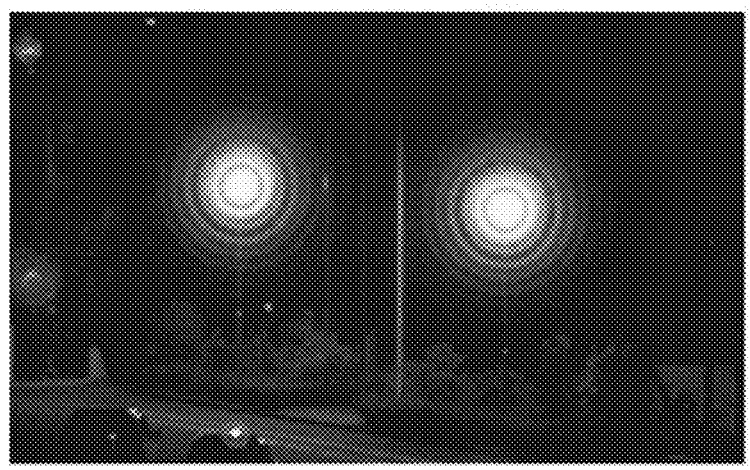
FIG. 37 is an actual photo of halos in the phase profile of FIG. 35.

Next, FIG. 37 shows an actual photo of light sources of the present embodiment. Although the brightness near the center of the light source is on the high side, the lens is found to be fully usable even at night since it does not produce extensively planar halos as shown in the comparative example (FIG. 10B).

Figure 38:
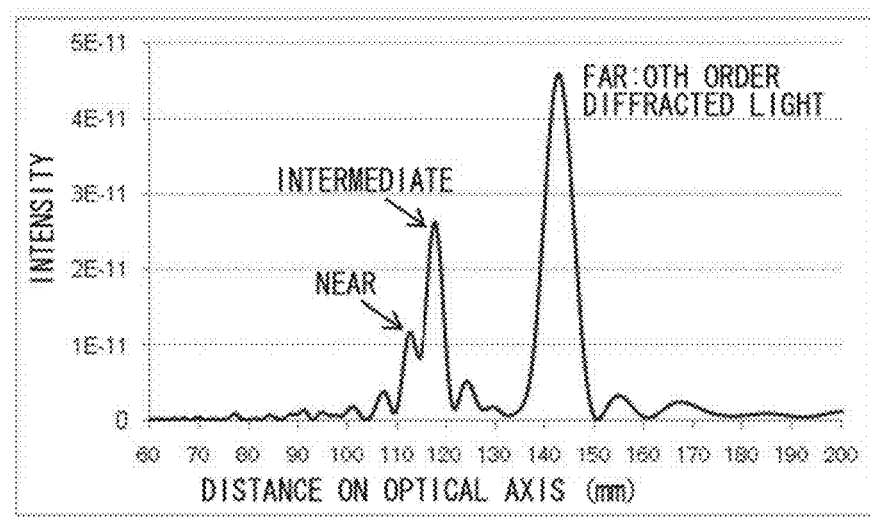
FIG. 38 is a graph showing results of simulation of intensity distribution on the optical axis in the phase profile of FIG. 35.

FIG. 38 shows results of computer simulation of intensity distribution on the optical axis obtained in the present embodiment. These results are derived from the calculation of the 1st to 5th zones of Table 10. According to the present embodiment, it is observed that a peak in the intermediate region is formed close to the peak in the near region. Such an example where the focal peak in the intermediate region is formed close to that in the near region would be suitable for the usage such as looking back and forth between a computer monitor and a nearby document during work.

As described in the fifth, sixth and seventh embodiments, by means of combining the regions of Fresnel pitches and equal pitches, it becomes possible to prevent the formation of extensively planar halos that appear in case of having a region with Fresnel pitches only, to determine a focal point in near distance fixed by the Fresnel region that has been partially introduced, and to enhance the degree of design freedom that allows a focal point to be formed in the intermediate region with equal pitches.

Figure 39:
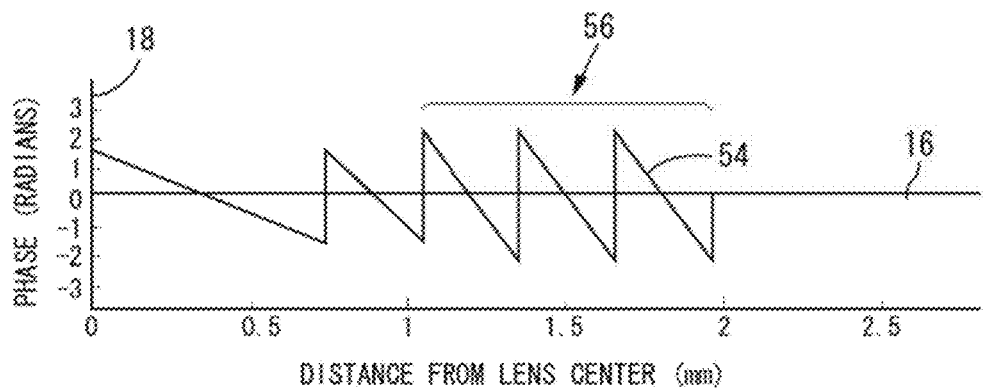
FIG. 39 is a phase profile as an eighth embodiment of the present invention.

FIG. 39 shows a magnified cross section of a phase profile 54 as an eighth embodiment of the present invention. As shown in Table 11 below, the present embodiment takes over the fifth embodiment with is phase constant of an equal-pitch region 56 changed to 0.7. This embodiment is presented as an example to show the variation of side-band intensity caused by the change in the value of the phase constant h.

TABLE 11

| Zone No. | Zone radius | | Phase | | | |
| | $r_n$ (mm) | $r_{n-1}$ (mm) | $\phi_n$ (radian) | $\phi_{n-1}$ (radian) | constant h | Pitch |
|---|---|---|---|---|---|---|
| $1^{st}$ zone | 0.738918 | 0 | −1.5708 | 1.5708 | 0.5 | Fresnel pitch |
| $2^{nd}$ zone | 1.044988 | 0.738918 | −1.5708 | 1.5708 | 0.5 | |
| $3^{rd}$ zone | 1.351057 | 1.044988 | −2.1991 | 2.1991 | 0.7 | Equal pitch |
| $4^{th}$ zone | 1.657127 | 1.351057 | −2.1991 | 2.1991 | 0.7 | |
| $5^{th}$ zone | 1.963197 | 1.657127 | −2.1991 | 2.1991 | 0.7 | Δr = 0.306 mm |

Figure 40A:
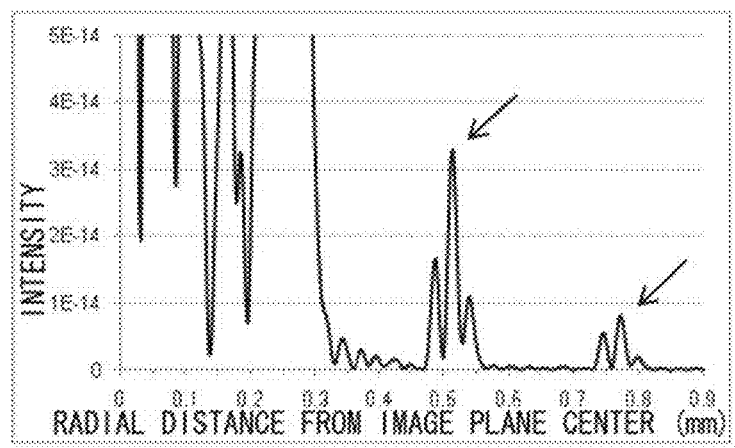
FIGS. 40A and 40B are graphs for comparing a result of simulation of intensity distribution with that of the comparative example at the focal point position of 0th order diffracted light in the phase profile of FIG. 39.
Figure 40B:
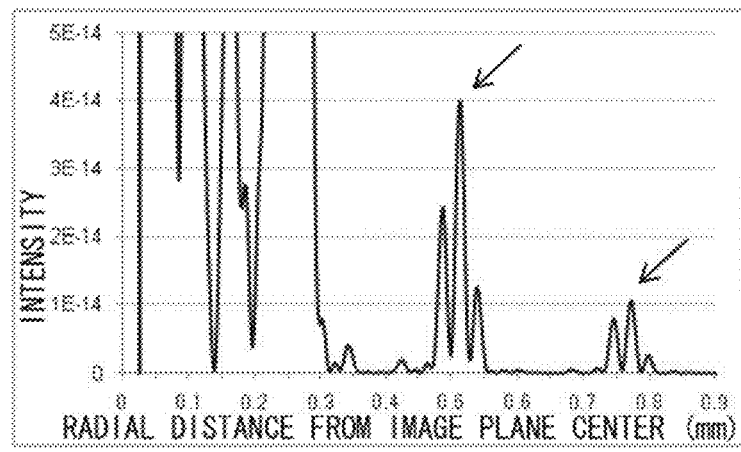

FIGS. 40A and 40B show results of computer simulation of the image plane intensity distribution at the focal point position of the 0th order diffracted light of the present invention (FIG. 40A) as compared to those of the fifth embodiment (FIG. 40B). These results are derived from the calculation of the 1st to 5th zones of Table 11 (FIG. 40A) and the 1st to 5th zones of Table 8 (FIG. 40B). It is observed that no peaks other than those at q=1 increase their intensity, or they are rather decreasing, even if the phase constant is increased (marked by arrows in both figures). These variations of side-band intensity subsequent to changes in the phase constant h are based on Equation 15 and FIGS. 11B and 11C above. The scale of the vertical axis of these intensity distribution graphs is multiplied by 10 times of the graphs of the previous embodiments for easier viewing.

Figure 41A:
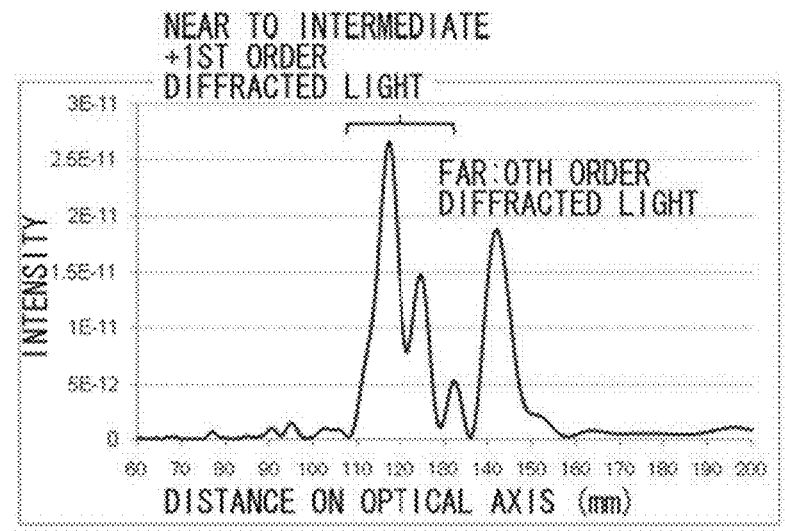
FIGS. 41A and 41B are graphs for comparing a result of simulation of intensity distribution with that of the comparative example on the optical axis in the phase profile of FIG. 39.
Figure 41B:
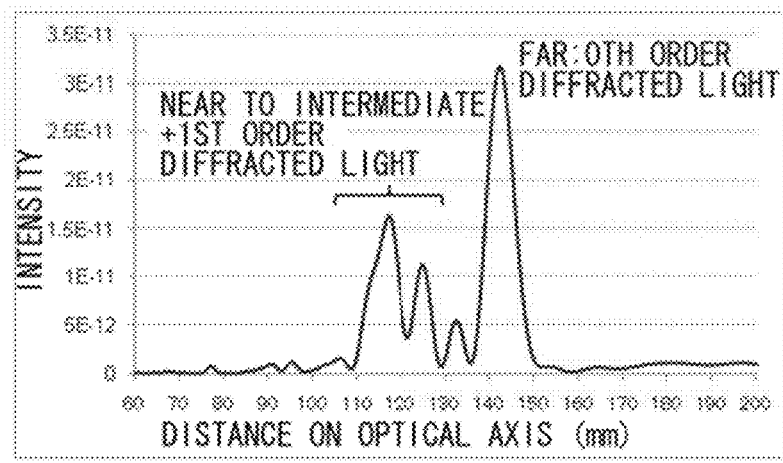

FIGS. 41A and 41B show results of computer simulation and confirmation of intensity distribution on the optical axis obtained in the present embodiment (FIG. 41A) as compared to those of the fifth embodiment (FIG. 41B). These results are derived from the calculation of the 1st to 4th zones of Table 11 (FIG. 41A) and the 1st to 4th zones of Table 8 (FIG. 41B). According to the present embodiment, it is observed that the intensity has risen in the near to intermediate regions due to the increased energy allocation to the first-order diffracted light in response to the increased phase constant h.

Figure 42:
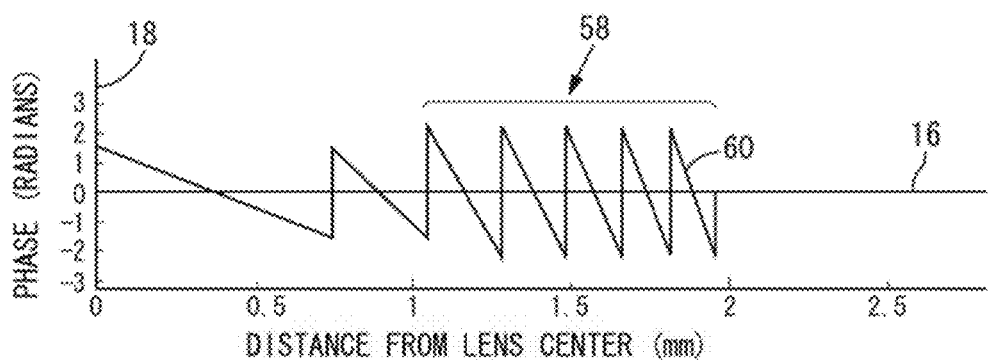
FIG. 42 is a phase profile as Comparative Example 2 of the present invention.

Next, in order to compare the simulation results to the case where the phase constant h for the Fresnel pitch is changed, the optical behavior was examined of the diffracted lens of Comparative Example 1 of the first embodiment (Table 2) only with Fresnel pitches wherein the phase constant h of a region 58 (3rd to 7th zones) equivalent to the region where the value of the phase constant h of the eighth embodiment is changed is raised from 0.5 to 0.7 (Table 12). FIG. 42 shows a magnified cross section of a phase profile 60 of such Comparative Example 2.

TABLE 12

| Zone No. | Zone radius | | Phase | | | |
| | $r_n$ (mm) | $r_{n-1}$ (mm) | $\phi_n$ (radian) | $\phi_{n-1}$ (radian) | Phase constant h | Pitch |
| --- | --- | --- | --- | --- | --- | --- |
| $1^{st}$ zone | 0.738918 | 0 | −1.5708 | 1.5708 | 0.5 | Fresnel pitch |
| $2^{nd}$ zone | 1.044988 | 0.738918 | −1.5708 | 1.5708 | 0.5 | |
| $3^{rd}$ zone | 1.279844 | 1.044988 | −2.1991 | 2.1991 | 0.7 | |
| $4^{th}$ zone | 1.477836 | 1.279844 | −2.1991 | 2.1991 | 0.7 | |
| $5^{th}$ zone | 1.652271 | 1.477836 | −2.1991 | 2.1991 | 0.7 | |
| $6^{th}$ zone | 1.809972 | 1.652271 | −2.1991 | 2.1991 | 0.7 | |
| $7^{th}$ zone | 1.954994 | 1.809972 | −2.1991 | 2.1991 | 0.7 | |

Figure 43A:
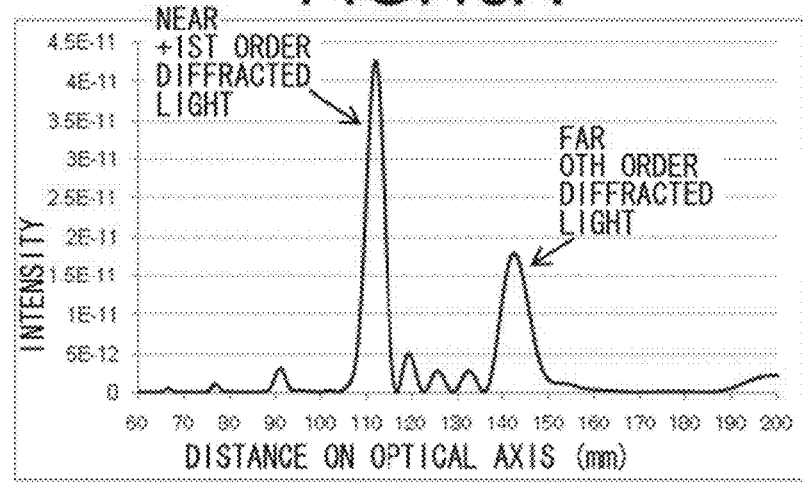
FIGS. 43A and 43B are graphs for comparing a result of simulation of intensity distribution with that of Comparative Example 1 on the optical axis in the phase profile of FIG. 42.
Figure 43B:
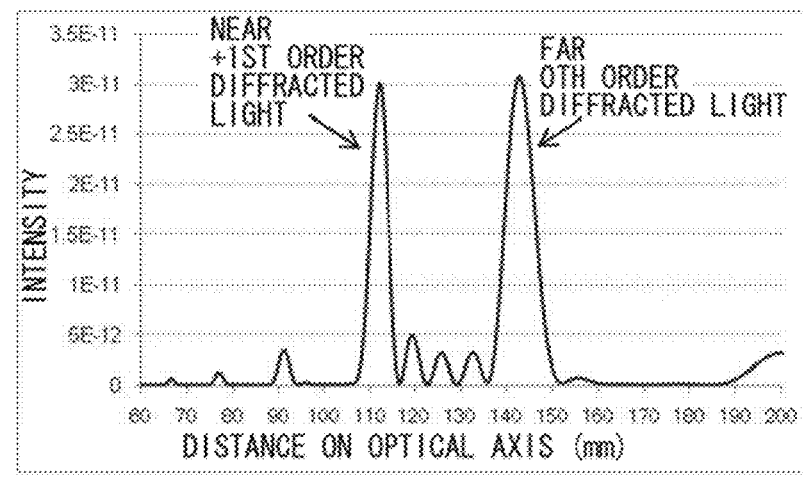

FIGS. 43A and 43B show results of computer simulation and confirmation of intensity distribution on the optical axis obtained in these comparative examples (FIG. 43A) as compared to Comparative Example 1 shown in Table 2 (FIG. 43B). These results are derived from the calculation of the 1st to 5th zones of Table 12 (FIG. 43A) and the 1st to 5th zones of Table 12 (FIG. 43B). It is observed that the ratio of peak intensity has risen even in Comparative Example 2 as a result of the increase in the constant h to 0.7.

Figure 44A:
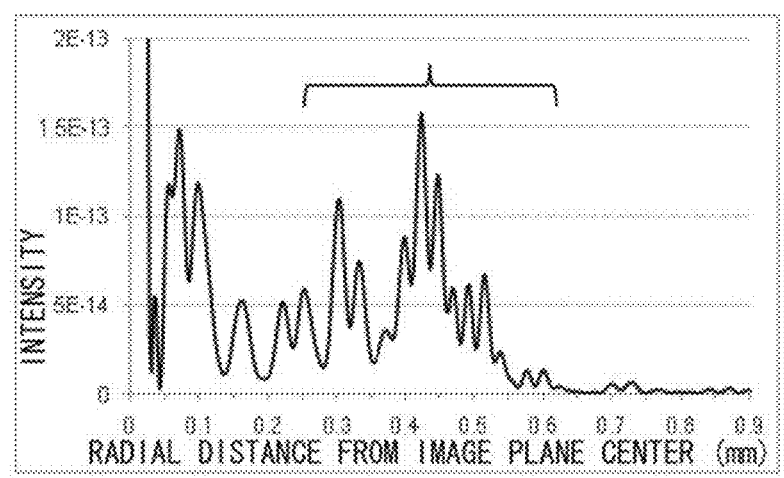
FIGS. 44A and 44B are graphs for comparing a result of simulation of intensity distribution with that of Comparative Example 1 on the image plane at the focal point position of 0th order diffracted light in the phase profile of FIG. 42.
Figure 44B:
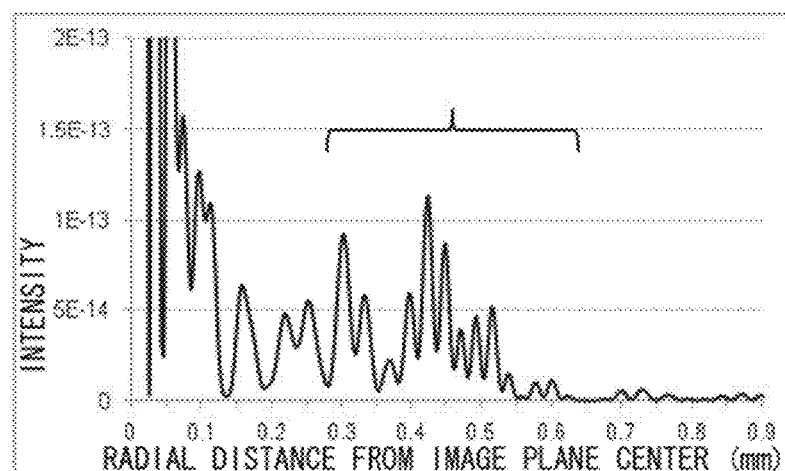

FIGS. 44A and 44B show results of computer simulation of the image plane intensity distribution at the focal point position of the 0th order diffracted light of Comparative Example 2 shown in FIG. 42 (FIG. 44A) as compared to Comparative Example 1 (FIG. 44B) shown in FIG. 8. These results are derived from the calculation of the 1st to 7th zones of Table 12 (FIG. 44A) and the 1st to 7th zones of Table 2 (FIG. 44B). As is the case for the equal-pitch system, the peak intensity of the first-order diffracted light in the intensity distribution on the optical axis increases as the phase constant h is increased, and it is also found that the side-band peaks grow up distinctively in the image plane intensity distribution. This is because the side-band of a diffraction-type lens with Fresnel pitches is mainly composed of side-band peaks at the order q=1 so that the side-band intensity goes up when the phase constant h gets larger based on Equation 15 and FIG. 11A described above. The scale of the vertical axis of these intensity distribution graphs is multiplied by 4 times from the graphs of the previous embodiments for easier viewing.

Thus, the main difference in side-band peak intensity on the image plane at a phase constant of h between a diffraction-type lens containing an equal-pitch region and a diffraction-type lens composed of Fresnel pitches is the difference in the order of peaks constituting the side-bands. The larger the phase constant h is, the larger the peak intensity is at the order q=1 as described above, but since the side-band peaks of the equal-pitch system at q=1 are formed near the center of the image plane, they don't directly affect the expansion of halos even if the intensity of these peaks gets higher. What directly affect the expansion of halos in the equal-pitch system are mainly side-band peaks at the order other than q=1 and these peaks maximize their intensity when h is about 0.5 to 0.56, but even the maximum intensity is much smaller than those at q=1, which means there is almost no impact on halos despite arbitrary changes of phase constant h. Meanwhile, since the side-band peaks formed in a multi-peak manner in the Fresnel pitch system are mainly consisting of a group of peaks at q=1, increasing the value of h leads to an increase in the intensity of the side-band peaks, resulting in the increase in halos.

Judging from such embodiment and Comparative Examples 1 and 2, it can be assumed that, in trying to increase the phase constant h in order to increase the energy allocation to the near and intermediate regions to further improve the vision therein, the Fresnel pitch system works adversely in terms of halos, but when an equal-pitch region is included in the lens, that can be a method of reducing the side-bands, thus further enhancing the design freedom.

Figure 45:
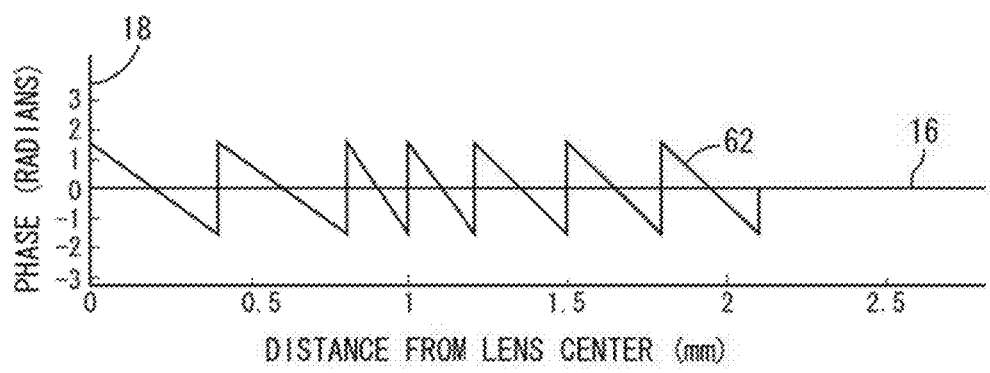
FIG. 45 is a phase profile as a ninth embodiment of the present invention.

FIG. 45 shows a magnified cross section of a phase profile 62 as a ninth embodiment of the present invention. As shown in Table 13, the present embodiment has three equal-pitch regions of different grating pitches at $\Delta r=0.4$ mm for the 1st and 2nd zones, $\Delta r=0.2$ mm for the 3rd to 4th zones, and $\Delta r=0.3$ mm for the 5th, 6th and 7th zones.

TABLE 13

| Zone No. | Zone radius | | Phase | | | |
| | $r_n$ (mm) | $r_{n-1}$ (mm) | $\phi_n$ (radian) | $\phi_{n-1}$ (radian) | Phase constant h | Pitch |
| --- | --- | --- | --- | --- | --- | --- |
| $1^{st}$ zone | 0.4 | 0 | −1.5708 | 1.5708 | 0.5 | $\Delta r = 0.4$ mm |
| $2^{nd}$ zone | 0.8 | 0.4 | −1.5708 | 1.5708 | 0.5 | |
| $3^{rd}$ zone | 1 | 0.8 | −1.5708 | 1.5708 | 0.5 | $\Delta r = 0.2$ mm |
| $4^{th}$ zone | 1.2 | 1 | −1.5708 | 1.5708 | 0.5 | |
| $5^{th}$ zone | 1.5 | 1.2 | −1.5708 | 1.5708 | 0.5 | $\Delta r = 0.3$ mm |
| $6^{th}$ zone | 1.8 | 1.5 | −1.5708 | 1.5708 | 0.5 | |
| $7^{th}$ zone | 2.1 | 1.8 | −1.5708 | 1.5708 | 0.5 | |

Figure 46A:
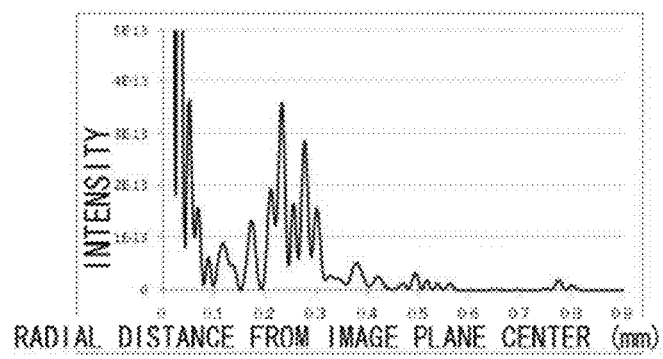
FIGS. 46A-46C are graphs suitable for explaining the Δr-dependability of the result of simulation of the image plane intensity distribution at the focal point position of 0th order diffracted light in the phase profile of FIG. 45.
Figure 46B:
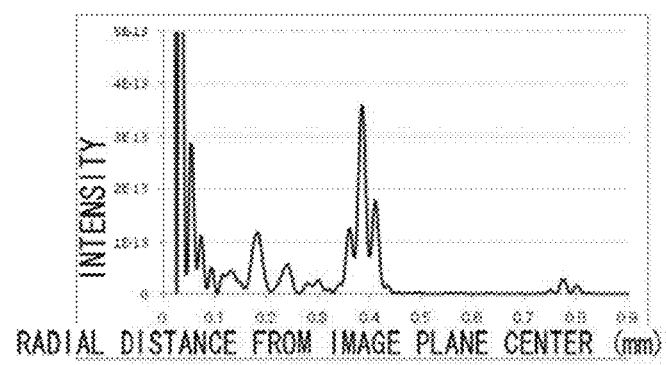
Figure 46C:
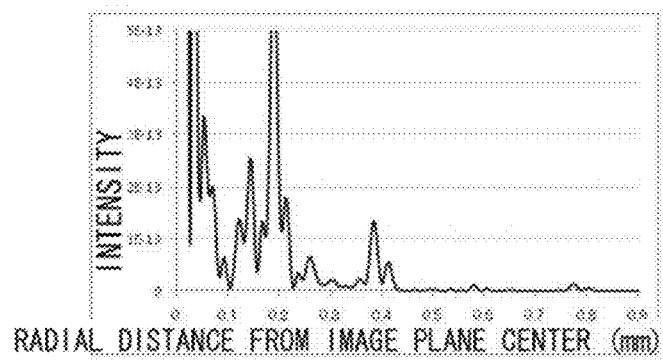

FIGS. 46A-46C show results of computer simulation of the image plane intensity distribution at the focal point position of the 0th order diffracted light of the present embodiment (FIG. 46A) as compared to the case where each grating pitch $\Delta r$ of the 5th, 6th and 7th zones is changed (FIG. 46B at $\Delta r=0.2$ mm (replaced with four zones of $\Delta r=0.2$ mm so as to get approximately the same outer diameter of the diffraction zone; Table 14) and FIG. 46C at $\Delta r=0.4$ mm (replaced with two zones of $\Delta r=0.4$ mm for the same purpose; Table 15). These results are derived from the calculation of the 1st to 7th zones of Table 13 (FIG. 46A), the 1st to 8th zones of Table 14 (FIG. 46B), and the 1st to 6th zones of Table 15 (FIG. 46C). In case of the present embodiment shown in FIG. 46A, intricately split steep side-band peaks appear with relatively high intensity near the center of the image plane at $\rho=0.2$ to 0.3 mm, but almost no peak exists in the periphery of the distribution. The reason for the intricately split peaks is considered to be the diversity of mutual wave interference caused by the three zones with different grating pitches $\Delta r$. In this case, the halo at night is assumed to have high ring brightness with little expansion, which leads us to expect a diffraction-type lens with reduced halos. In the same token, other variations (FIGS. 46B and 46C) are expected to make a diffraction-type lens with reduced halos.

TABLE 14

| Zone No. | Zone radius | | Phase | | | |
|---|---|---|---|---|---|---|
| | $r_n$ (mm) | $r_{n-1}$ (mm) | $\phi_n$ (radian) | $\phi_{n-1}$ (radian) | Phase constant h | Pitch |
| $1^{st}$ zone | 0.4 | 0 | −1.5708 | 1.5708 | 0.5 | $\Delta r = 0.4$ mm |
| $2^{nd}$ zone | 0.8 | 0.4 | −1.5708 | 1.5708 | 0.5 | |
| $3^{rd}$ zone | 1 | 0.8 | −1.5708 | 1.5708 | 0.5 | $\Delta r = 0.2$ mm |
| $4^{th}$ zone | 1.2 | 1 | −1.5708 | 1.5708 | 0.5 | |
| $5^{th}$ zone | 1.4 | 1.2 | −1.5708 | 1.5708 | 0.5 | |
| $6^{th}$ zone | 1.6 | 1.4 | −1.5708 | 1.5708 | 0.5 | |
| $7^{th}$ zone | 1.8 | 1.6 | −1.5708 | 1.5708 | 0.5 | |
| $8^{th}$ zone | 2 | 1.8 | −1.5708 | 1.5708 | 0.5 | |

TABLE 15

| Zone No. | Zone radius | | Phase | | | |
|---|---|---|---|---|---|---|
| | $r_n$ (mm) | $r_{n-1}$ (mm) | $\phi_n$ (radian) | $\phi_{n-1}$ (radian) | Phase constant h | Pitch |
| $1^{st}$ zone | 0.4 | 0 | −1.5708 | 1.5708 | 0.5 | $\Delta r = 0.4$ mm |
| $2^{nd}$ zone | 0.8 | 0.4 | −1.5708 | 1.5708 | 0.5 | |
| $3^{rd}$ zone | 1 | 0.8 | −1.5708 | 1.5708 | 0.5 | $\Delta r = 0.2$ mm |
| $4^{th}$ zone | 1.2 | 1 | −1.5708 | 1.5708 | 0.5 | |
| $5^{th}$ zone | 1.6 | 1.2 | −1.5708 | 1.5708 | 0.5 | $\Delta r = 0.4$ mm |
| $6^{th}$ zone | 2 | 1.6 | −1.5708 | 1.5708 | 0.5 | |

Figure 47A:
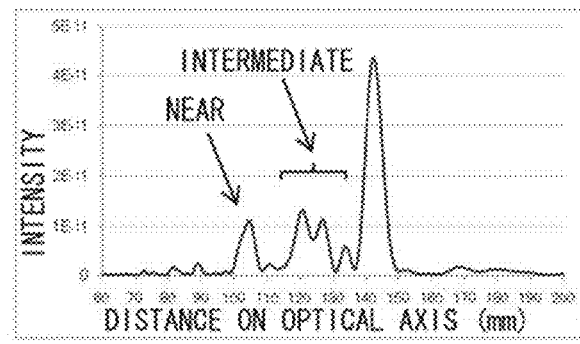
FIGS. 47A-47C are graphs suitable for explaining the Δr-dependability of the result of simulation of intensity distribution on the optical axis in the phase profile of FIG. 45.
Figure 47B:
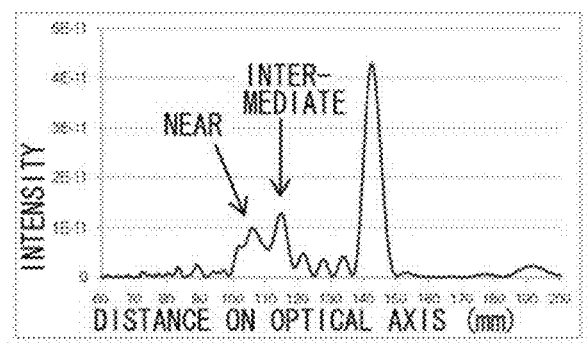
Figure 47C:
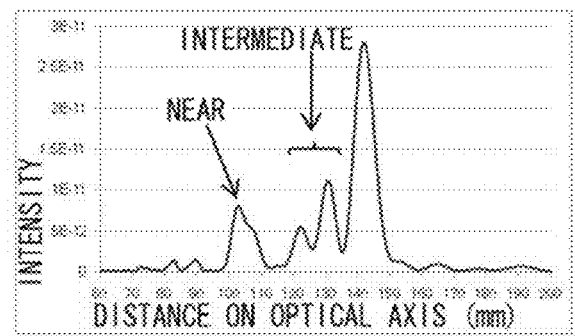
Figure 48A:
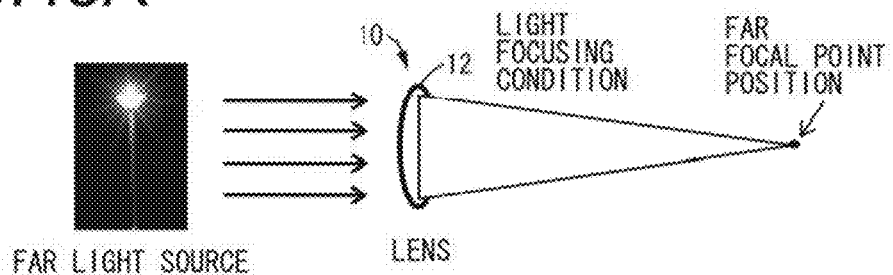
FIGS. 48A-48D are diagrams and graphs suitable for explaining imaging characteristics of a monofocal lens.
Figure 48B:
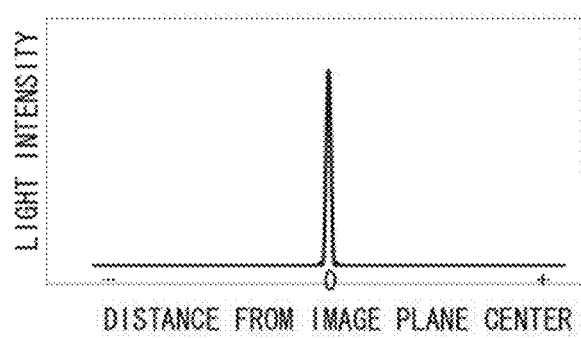
Figure 48C:
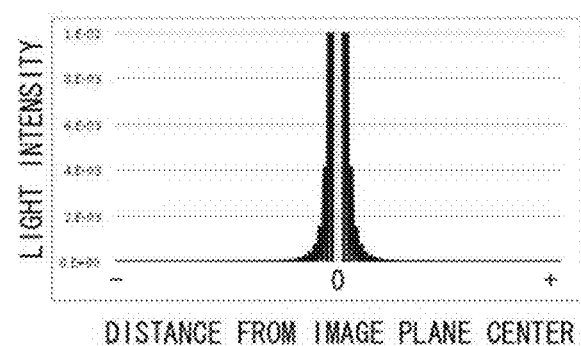
Figure 48D:
Figure 49A:
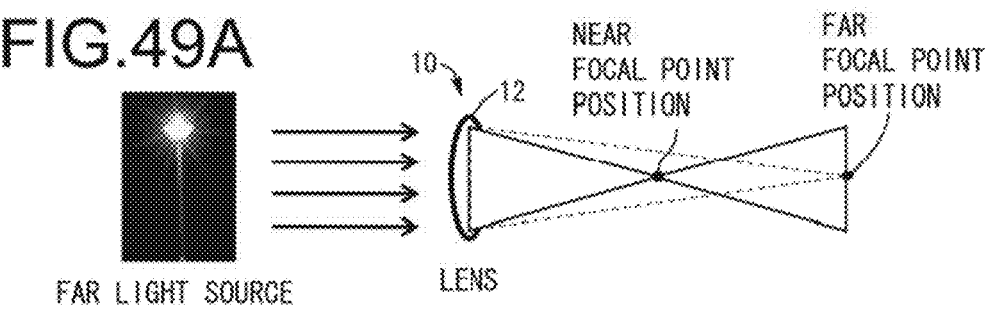
FIGS. 49A-49D are diagrams and graphs suitable for explaining formation of halos in a diffraction-type multifocal lens.
Figure 49B:
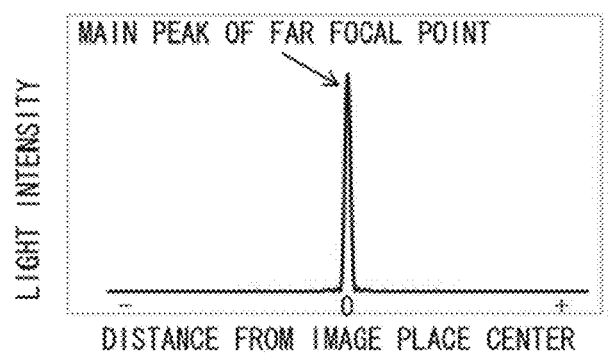
Figure 49C:
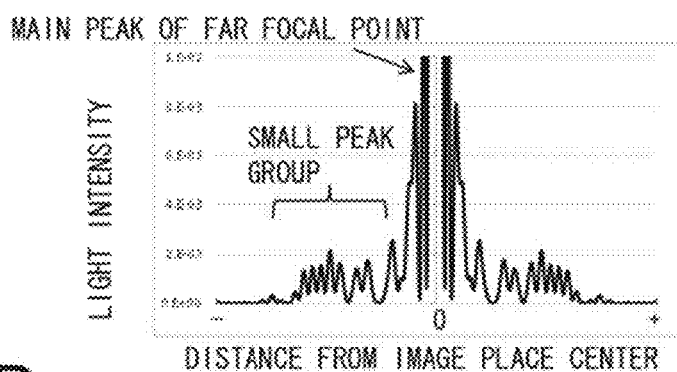
Figure 49D:
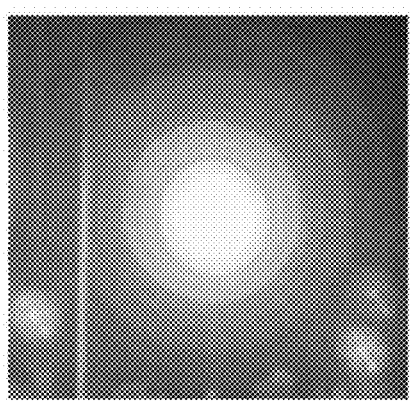

FIGS. 47A-47C show results of computer simulation and confirmation of intensity distribution on the optical axis obtained in the present embodiment (FIG. 47A) as compared to the case where the grating pitches Δr of the 5th, 6th and 7th zones are changed to 0.2 mm (FIG. 47B) and 0.4 mm (FIG. 47C). These results are derived from the calculation of the 1st to 6th zones of Table 13 (FIG. 47A), the 1st to 7th zones of Table 14 (FIG. 47B), and the 1st to 5th zones of Table 15 (FIG. 47C). Recognizing a peak in the near region and twin peaks in the intermediate region in the present embodiment shown in FIG. 47A, they are expected to provide a well-balanced vision among the far, intermediate and near regions. Since the present embodiment is a good example for explaining a method of making fine adjustments to the formation of focal points in the near to intermediate regions by combining different grating pitches, such a method of fine adjustment will be described later.

When the region of Δr=0.3 mm is replaced with that of Δr=0.2 mm, the near and intermediate peaks appear to be overlapping with each other as shown in FIG. 47B. In such an example, the near and intermediate regions get too close to each other, which can thwart the purpose if they need to be separated apart. When the region of Δr=0.3 mm is replaced with that of Δr=0.4 mm as shown in FIG. 47C, a peak appears in the near region, but the peaks seemingly belonging to the intermediate region are too close to the peak of the 0th order diffracted light, and as a result, it does not necessarily serve the purpose of setting the intermediate region closer to the near region. However, as shown in the present embodiment, it is seen that a focal point position can be set in a proper intermediate region between the near and far regions by including the equal-pitch region at Δr=0.3 mm, which is a median between Δr=0.2 mm and Δr=0.4 mm, as one of the components of the diffraction structure. When the pitch is set large at Δr=0.4 mm, intensity distribution on the optical axis of the first-order diffracted light asymptotically gets closer to the 0th order focal point position as can be seen in Equation 19 or 20 and FIG. 14 so that the first-order diffracted light at Δr=0.4 mm gets too close to the peak of the 0th order diffracted light as shown in the figure. Meanwhile, if the pitch is set too small at Δr=0.2 mm, intensity distribution of the first-order diffracted light would be overlapping with the peaks in the near region by extending over to the position far away from the 0th order diffracted light as can be seen in Equation 19 or 20 and FIG. 14. Therefore, such two extreme behaviors can be adjusted to have a focal point at the most appropriate position by means of adding a proper grating pitch Δr. In the present embodiment, the pitch Δr=0.3 mm plays a role as such adjustor. Further addition of such a different grating pitch Δr can reduce the halo and achieve a diffraction-type multifocal lens with an adjusted balance among the visions in the far, intermediate and near regions. The present embodiment is quoted as an example of the adjustment method in the intermediate region, and the present invention is not limited by such embodiment.

The diffraction structure referred to in each of the above embodiments and others can be installed on either the front or back surface of the intended ophthalmic lens or on the same plane thereof, or can even be installed within the lens.

The ophthalmic lens of the present invention specifically includes a contact lens and an intraocular lens. In addition, a corneal inlay lens that is planted into the corneal stroma to correct the vision or an artificial cornea can also be adopted. For contact lenses, the present invention can be favorably applied to an oxygen-permeable hard contact lens, an aqueous or non-aqueous soft contact lens, or even an aqueous or non-aqueous oxygen-permeable soft contact lens containing silicone ingredients. As to intraocular lenses, it can also be used favorably for any of them including a hard-type intraocular lens or a soft-type intraocular lens that can be inserted into the eye in folding.

As described above in reference to each of the embodiments, the structural configurations of the equal-pitch region in designing the diffraction structure containing the equal-pitch regions include the one where the entire diffraction structure is constructed of equal-pitch regions composed of a single grating pitch (Δr), the one with multiple equal-pitch regions made of different grating pitches (Δr), the one composed of a repeated periodic structure where a zone of a single grating pitch (Δr) is arranged at equal intervals, or the one composed of a repeated periodic structure where zones of different grating pitches (Δr) are alternately arranged, and further the one with multiple zones of a single grating pitch (Δr) arranged at unequal intervals and so forth. Also, the one composed of a combination between equal-pitch regions and regions with pitches in accordance with other rules is included in the aspects of the present invention, and an equal-pitch region combined with a Fresnel-pitch region, for example, is one of the favorable aspects of the present invention. In other words, between zones constituting an equal-pitch region, other zones (that do not constitute the equal-pitch region) can be interposed, and the number and size of other zones interposed between the zones constituting the equal-pitch region can either be constant or different from each other between each zone that constitutes the equal-pitch region depending on the requirements of optical characteristics. Thus, since there can be more permutations and combinations for the configuration of the diffraction structure containing equal-pitch regions other than those described above, the configuration is not limited to those examples. By means of properly selecting and combining the grating pitches (Δr), phase constant h, and structural configuration of equal-pitch regions, the halo can be reduced, while allowing the design of a diffraction-type multifocal lens that can achieve focal point formation in response to the physiological needs of users at appropriate positions in the far and near regions, or far, intermediate and near regions.

| KEYS TO SYMBOLS | | |
|---|---|---|
| 10: Ophthalmic lens; | 16: Optical part back surface; | 18: Lens central axis; |
| 20: Diffraction structure; | 26: Phase profile; | |
| 28, 48: Equal-pitch region; | 46: Fresnel region | |

The invention claimed is:

1. A diffraction-type multifocal ophthalmic lens having a diffraction structure where a plurality of diffraction zones are formed concentrically on the lens, comprising at least one equal-pitch region where pitches of at least two zones among the diffraction zones are made equal,
wherein the diffraction structure has a Fresnel region composed of a periodic structure with a Fresnel pitch and the equal-pitch region, and
the pitch of the Fresnel region is determined by the following equation:

$$r_n = \sqrt{\frac{\{2(n-1)+g\} \times \lambda}{P_{add}}}$$ [Equation 1]

$n$: Diffraction zone number of the Fresnel region $$g = \frac{P_{add} \times r_1^2}{\lambda}$$

$\lambda$: Wave length $P_{add}$: Addition power in setting a focal
point of a first-order diffracted light in the
Fresnel region using a focal point position
of a 0th order diffracted light as a reference $r_n$: Outer radius of an $n^{th}$ diffraction
zone of the Fresnel region $r_1$: Outer radius of a $1^{st}$ diffraction
zone of the Fresnel region.

2. The diffraction-type multifocal ophthalmic lens according to claim 1, wherein the equal-pitch region is configured by the diffraction zones which are adjacent to each other.

3. The diffraction-type multifocal ophthalmic lens according to claim 1, wherein the equal-pitch region is configured by the diffraction zones which are not adjacent to each other.

4. The diffraction-type multifocal ophthalmic lens according to claim 1, wherein the at least one equal-pitch region comprises a plurality of equal-pitch regions in which the pitches of the diffraction zones are made different among the equal-pitch regions.

5. The diffraction-type multifocal ophthalmic lens according to claim 4, wherein at least two equal-pitch regions are adjacent to each other in the diffraction structure where the equal-pitch regions are provided in which the pitches of the diffraction zones are made different among the equal-pitch regions.

6. The diffraction-type multifocal ophthalmic lens according to claim 4, wherein at least two equal-pitch regions are provided without being adjacent to each other in the diffraction structure where the equal-pitch regions are provided in which the pitches of the diffraction zones are made different among the equal-pitch regions.

7. The diffraction-type multifocal ophthalmic lens according to claim 1, wherein the Fresnel region is arranged in an inner peripheral portion of the diffraction structure and the equal-pitch region is arranged in an outer peripheral portion thereof.

8. The diffraction-type multifocal ophthalmic lens according to claim 1, wherein the Fresnel region is arranged in an outer peripheral portion of the diffraction structure and the equal-pitch region is arranged in an inner peripheral portion thereof.

9. The diffraction-type multifocal ophthalmic lens according to claim 1, wherein the diffraction structure is composed of diffraction zones expressed by a phase function that determines light phases.

10. The diffraction-type multifocal ophthalmic lens according to claim 9, wherein the phase function of the diffraction zone is composed of a blaze-like function.

11. The diffraction-type multifocal ophthalmic lens according to claim 10, wherein the blaze-like phase function of the diffraction zone is expressed by the following equation:

$$\phi_n(r) = \left(\frac{\phi_n - \phi_{n-1}}{r_n - r_{n-1}}\right) \times r + \left(\frac{\phi_{n-1} \times r_n - \phi_n \times r_{n-1}}{r_n - r_{n-1}}\right)$$ [Equation 2]

$\phi_n(r)$: Phase function $\phi_n$: Phase at a position of
an outer radius of the diffraction zone $\phi_{n-1}$: Phase at a position of an inner
radius of the diffraction zone $r_n$: Outer radius of the diffraction zone $r_{n-1}$: Inner radius of the diffraction zone.

12. The diffraction-type multifocal ophthalmic lens according to claim 1, wherein, in the equal-pitch region provided with the diffraction zones adjacent to each other, the pitch $\Delta r$ of the diffraction zones of the equal-pitch region is determined to fall within a range of $\rho_q$ (mm)<|0.006×f (mm)×q| corresponding to a position $\rho_q$ of a q-th order diffracted light (q is an integer except zero) on the focal point image plane of a 0th order diffracted light in the diffraction structure determined by the following equation:

$$\rho_q = \frac{2qf\pi}{k\Delta r}$$ [Equation 3]

$\Delta r$: Pitch of the diffraction
zones in the equal-pitch region $\rho_q$: Position of the $q$-th order side-band peak in a
radial direction from a center of the focal point
image plane of the 0th order diffracted light $q$: Integer except zero $f$: Focal length of the 0th order diffracted light $k$: Wavenumber, $k = 2\pi/\lambda$ (wavelength of light).

13. The diffraction-type multifocal ophthalmic lens according to claim 1, wherein the pitch of the diffraction zones of the equal-pitch region is from 0.1 mm to 0.5 mm.

14. The diffraction-type multifocal ophthalmic lens according to claim 1, wherein a first-order diffracted light of the equal-pitch region forms multiple focal points.

15. The diffraction-type multifocal ophthalmic lens according to claim 14, wherein the multiple focal points by the first-order diffracted light in the diffraction structure of the equal-pitch region are generated in response to enlargement of an aperture diameter that determines a range of substantial incidence or emission of light in the lens having the diffraction structure.

16. The diffraction-type multifocal ophthalmic lens according to claim 15, wherein the multiple focal points by the first-order diffracted light in the diffraction structure of the equal-pitch region are generated when the aperture diameter that determines the range of substantial incidence or emission of light in the lens having the diffraction structure is enlarged to 1.5 mm or more.

17. The diffraction-type multifocal ophthalmic lens according to claim 1, wherein a focal length of a first-order diffracted light in the diffraction structure is set smaller than that of a 0th order diffracted light in the diffraction structure.

18. The diffraction-type multifocal ophthalmic lens according to claim 1, wherein the diffraction structure has the Fresnel region composed of the periodic structure with the Fresnel pitch and the equal-pitch region, while at least one of multiple focal lengths by a first-order diffracted light of the equal-pitch region is made larger than a focal length by a first-order diffracted light of the Fresnel region.

19. The diffraction-type multifocal ophthalmic lens according to claim 18, wherein a focal point of the first-order diffracted light of the equal-pitch region which forms a focal length larger than that of the first-order diffracted light of the Fresnel region is generated when an aperture diameter that determines a range of substantial incidence or emission of light in the lens having the diffraction structure is enlarged to 1.5 mm or more.

20. A manufacturing method of a diffraction-type multifocal ophthalmic lens having a diffraction structure where a plurality of diffraction zones are formed concentrically on the lens, comprising forming the diffraction structure composed of an equal-pitch region where pitches of at least two zones among the diffraction zones are made equal, wherein the diffraction structure has a Fresnel region composed of a periodic structure with a Fresnel pitch and the equal-pitch region, and the pitch of the Fresnel region is determined by the following equation:

$$r_n = \sqrt{\frac{\{2(n-1)+g\} \times \lambda}{P_{add}}} \quad \text{[Equation 1]}$$

$n$: Diffraction zone number of the Fresnel region $$g = \frac{P_{add} \times r_1^2}{\lambda}$$

$\lambda$: Wave length $P_{add}$: Addition power in setting a focal point of a first-order diffracted light in the Fresnel region using a focal point position of a 0th order diffracted light as a reference $r_n$: Outer radius of an $n^{th}$ diffraction zone of the Fresnel region $r_1$: Outer radius of a $1^{st}$ diffraction zone of the Fresnel region.

* * * * *